United States Patent
Finch

(10) Patent No.: US 11,077,273 B2
(45) Date of Patent: Aug. 3, 2021

(54) PATIENT INTERFACE WITH VOLUME REDUCING MEMBER

(71) Applicant: ResMed Pty Ltd, Bella Vista (AU)

(72) Inventor: Charles Harry Finch, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 351 days.

(21) Appl. No.: 15/743,693

(22) PCT Filed: Jul. 18, 2016

(86) PCT No.: PCT/AU2016/050634
§ 371 (c)(1),
(2) Date: Jan. 11, 2018

(87) PCT Pub. No.: WO2017/011864
PCT Pub. Date: Jan. 26, 2017

(65) Prior Publication Data
US 2018/0200467 A1 Jul. 19, 2018

Related U.S. Application Data

(60) Provisional application No. 62/194,451, filed on Jul. 20, 2015.

(51) Int. Cl.
*A61M 16/06* (2006.01)
*A61M 16/10* (2006.01)
*A61M 16/22* (2006.01)

(52) U.S. Cl.
CPC ........ *A61M 16/0611* (2014.02); *A61M 16/06* (2013.01); *A61M 16/0616* (2014.02);
(Continued)

(58) Field of Classification Search
CPC .......... A61M 16/0611; A61M 16/0616; A61M 16/0622; A61M 16/06; A61M 16/0605;
(Continued)

(56) References Cited

U.S. PATENT DOCUMENTS

| 680,419 A | * | 8/1901 | Schaeffer | A62B 17/04 128/201.23 |
| 938,247 A | * | 10/1909 | Kuhn | A61M 16/06 128/206.26 |

(Continued)

FOREIGN PATENT DOCUMENTS

| CN | 103140254 A | 6/2013 |
| CN | 204017056 U | 12/2014 |

(Continued)

OTHER PUBLICATIONS

Extended European Search Report dated Mar. 20, 2019 in European Application No. 16826925.6, 12 pages.

(Continued)

*Primary Examiner* — Jan Christopher L Merene
*Assistant Examiner* — Brian T Khong
(74) *Attorney, Agent, or Firm* — Nixon & Vanderhye P.C.

(57) ABSTRACT

A patient interface includes a cushion assembly adapted to form a seal around the patient's nose and/or mouth and a gas washout vent configured to allow a flow of patient exhaled $CO_2$ to an exterior of the patient interface to minimise rebreathing of exhaled $CO_2$ by the patient. The cushion assembly defines a plenum chamber pressurised at a pressure above ambient pressure in use. At least one volume reducing member is provided within the plenum chamber to reduce an effective internal volume of the plenum chamber. The at least one volume reducing member is arranged to separate a main volume of the plenum chamber for delivery of the therapy pressure from deadspace volume provided at least superior the entrance to the patient's nasal passages. The main volume is adapted to be in direct fluid communication with the patient's nose and/or mouth and the vent.

27 Claims, 42 Drawing Sheets

(52) U.S. Cl.
CPC ........ *A61M 16/1045* (2013.01); *A61M 16/22* (2013.01); *A61M 16/0683* (2013.01); *A61M 2202/0225* (2013.01); *A61M 2205/0216* (2013.01); *A61M 2205/42* (2013.01)

(58) Field of Classification Search
CPC .............. A61M 16/1045; A61M 16/22; A61M 16/0683; A62B 17/04; A62B 18/02; A62B 18/025; A62B 18/06
See application file for complete search history.

(56) References Cited

U.S. PATENT DOCUMENTS

| | | | |
|---|---|---|---|
| 2,248,477 A * | 7/1941 | Lombard | A61M 16/0683 128/205.25 |
| 3,602,219 A * | 8/1971 | Warncke | A61M 16/06 128/201.15 |
| 4,782,832 A | 11/1988 | Trimble et al. | |
| 4,794,921 A * | 1/1989 | Lindkvist | A61M 16/0816 128/203.29 |
| 4,905,683 A | 3/1990 | Cronjaeger | |
| 4,907,584 A * | 3/1990 | McGinnis | A61M 16/06 128/206.24 |
| 4,944,310 A | 7/1990 | Sullivan | |
| 5,265,595 A | 11/1993 | Rudolph | |
| 5,560,354 A * | 10/1996 | Berthon-Jones | A61M 16/06 128/204.18 |
| 5,909,732 A * | 6/1999 | Diesel | A62B 18/08 128/205.25 |
| 6,374,826 B1 | 4/2002 | Gunaratnam et al. | |
| 6,532,959 B1 | 3/2003 | Berthon-Jones | |
| 6,581,594 B1 | 6/2003 | Drew et al. | |
| 7,004,162 B1 * | 2/2006 | Foley | A61M 15/00 128/200.14 |
| 7,243,650 B2 * | 7/2007 | Thornton | A61M 16/06 128/205.25 |
| 7,866,944 B2 | 1/2011 | Kenyon et al. | |
| 7,938,445 B2 * | 5/2011 | Smith | B60R 21/2338 280/743.2 |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 2002/0029780 A1 * | 3/2002 | Frater | A61M 16/06 128/206.24 |
| 2002/0053347 A1 | 5/2002 | Ziaee | |
| 2002/0096178 A1 * | 7/2002 | Ziaee | A61M 16/06 128/207.18 |
| 2003/0135915 A1 * | 7/2003 | Luppi | A61M 16/06 2/424 |
| 2004/0112385 A1 * | 6/2004 | Drew | A61M 16/06 128/206.21 |
| 2005/0115567 A1 * | 6/2005 | Bridges | A62B 18/04 128/206.21 |
| 2006/0289004 A1 * | 12/2006 | Saez | A62B 17/04 128/201.24 |
| 2007/0006879 A1 * | 1/2007 | Thornton | A61M 16/06 128/203.29 |
| 2007/0089749 A1 | 4/2007 | Ho et al. | |
| 2007/0215161 A1 * | 9/2007 | Frater | A61M 16/0638 128/206.24 |
| 2008/0142014 A1 * | 6/2008 | Jiang | A61M 16/06 128/206.24 |
| 2008/0295846 A1 * | 12/2008 | Han | A61M 16/06 128/207.13 |
| 2009/0014007 A1 | 1/2009 | Brambilla et al. | |
| 2009/0044808 A1 | 2/2009 | Guney et al. | |
| 2009/0050156 A1 | 2/2009 | Ng et al. | |
| 2009/0107515 A1 * | 4/2009 | Gavriely | A62B 9/02 128/863 |
| 2009/0114229 A1 * | 5/2009 | Frater | A61M 16/06 128/206.24 |
| 2009/0120442 A1 * | 5/2009 | Ho | A61M 16/0666 128/206.24 |
| 2009/0159084 A1 * | 6/2009 | Sher | A61M 16/06 128/205.24 |
| 2010/0000534 A1 | 1/2010 | Kooij et al. | |
| 2010/0024811 A1 * | 2/2010 | Henry | A61H 9/0078 128/202.16 |
| 2010/0059058 A1 | 3/2010 | Kuo | |
| 2010/0108067 A1 * | 5/2010 | Walker | A62B 17/04 128/205.24 |
| 2010/0122705 A1 * | 5/2010 | Moenning, Jr. | A61M 16/009 128/206.24 |
| 2011/0011397 A1 * | 1/2011 | Ziv | A61M 16/0616 128/203.12 |
| 2011/0108036 A1 * | 5/2011 | Thomas | A61M 16/06 128/206.22 |
| 2011/0232646 A1 * | 9/2011 | Ho | A61M 16/06 128/206.24 |
| 2011/0277768 A1 * | 11/2011 | Hill | A62B 7/10 128/205.28 |
| 2012/0080034 A1 | 4/2012 | Mansour et al. | |
| 2013/0118499 A1 * | 5/2013 | Parr | A61M 16/06 128/205.24 |
| 2013/0199537 A1 * | 8/2013 | Formica | A61M 16/0825 128/205.25 |
| 2014/0190476 A1 * | 7/2014 | Stinton | A41D 13/1153 128/201.23 |
| 2014/0216474 A1 * | 8/2014 | Mittelstadt | A62B 18/10 128/863 |
| 2015/0047644 A1 * | 2/2015 | Baiko | A61M 16/06 128/206.26 |
| 2015/0174354 A1 * | 6/2015 | Matula, Jr. | A61M 16/06 128/202.27 |
| 2015/0202471 A1 * | 7/2015 | Boss | A62B 17/04 128/201.28 |
| 2015/0352308 A1 | 12/2015 | Cullen et al. | |
| 2016/0008566 A1 * | 1/2016 | Partington | A61M 16/0816 128/201.13 |
| 2016/0220781 A1 * | 8/2016 | Arrowsmith | F16K 31/1245 |

FOREIGN PATENT DOCUMENTS

| | | |
|---|---|---|
| GB | 649689 | 1/1951 |
| JP | 2006-122268 A | 5/2006 |
| JP | 2012-513229 A | 6/2012 |
| WO | WO 98/004310 | 2/1998 |
| WO | WO 98/034665 | 8/1998 |
| WO | WO 00/078381 | 12/2000 |
| WO | WO 2004/073778 | 9/2004 |
| WO | WO 2005/063328 | 7/2005 |
| WO | WO 2006/074513 | 7/2006 |
| WO | WO 2006/130903 | 12/2006 |
| WO | WO 2009/052560 | 4/2009 |
| WO | WO 2010/073138 A1 | 7/2010 |
| WO | WO 2010/135785 | 12/2010 |
| WO | WO 2012/171072 | 12/2012 |
| WO | WO 2013/144753 A1 | 10/2013 |
| WO | WO 2015/006826 | 1/2015 |
| WO | WO 2015/013761 A1 | 2/2015 |
| WO | WO 2015/161345 A1 | 10/2015 |
| WO | WO 2013/020167 | 2/2019 |

OTHER PUBLICATIONS

West, "Respiratory Physiology", Lippincott Williams & Wilkins, 9th edition published 2012, 8 pages.
International Search Report for PCT/AU2016/050634, dated Oct. 21, 2016, 5 pages.
Written Opinion for PCT/AU2016/050634, dated Oct. 21, 2016, 5 pages.
Written Opinion for PCT/AU2016/050634, dated Jul. 31, 2017, 4 pages.
International Preliminary Report on Patentability for PCT/AU2016/050634, dated Dec. 1, 2017, 15 pages.
Notification of the First Office Action dated Jan. 22, 2020 in Chinese Application No. 201680050861.8, with English translation, 20 pages.

(56) References Cited

OTHER PUBLICATIONS

Notice of Reasons for Rejection dated Jul. 6, 2020 in Japanese Application No. 2018-502697, with English translation, 15 pages.

\* cited by examiner

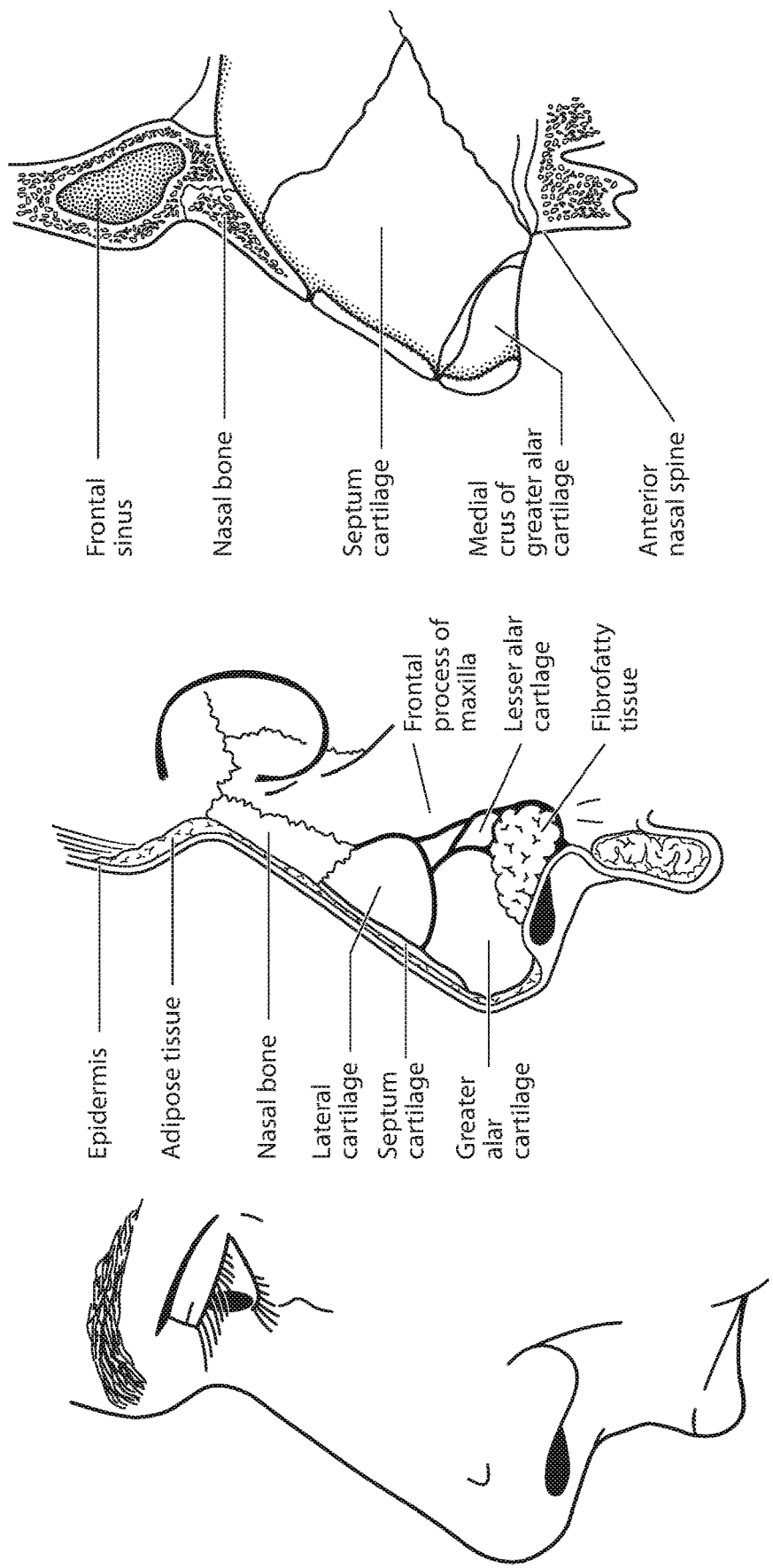

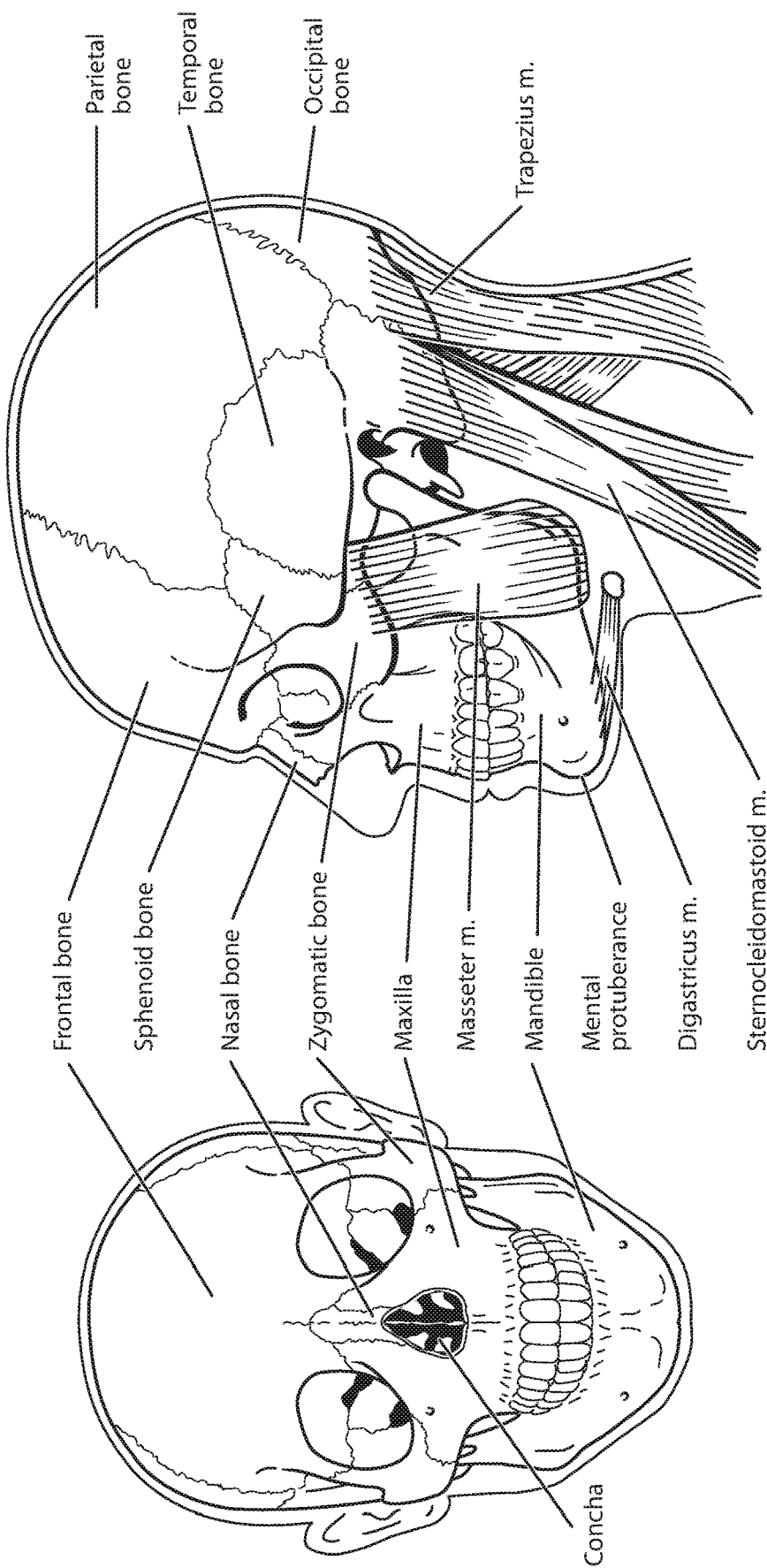

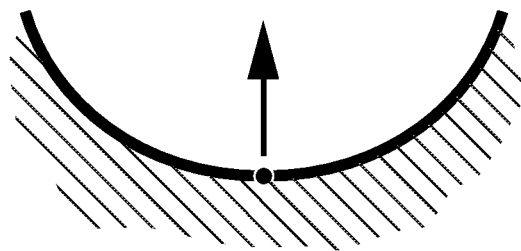
FIG. 3B — Relatively Large Positive Curvature
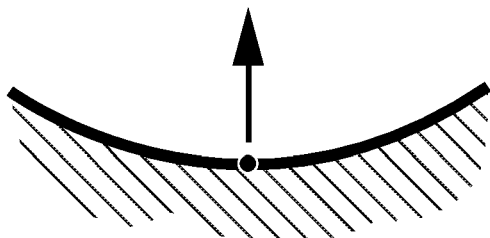
FIG. 3C — Relatively Small Positive Curvature
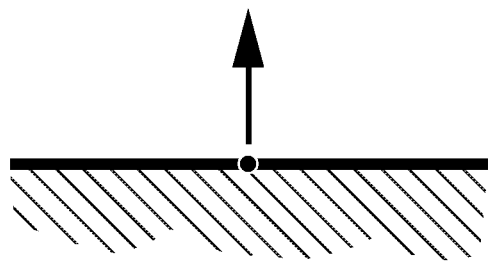
FIG. 3D — Zero Curvature
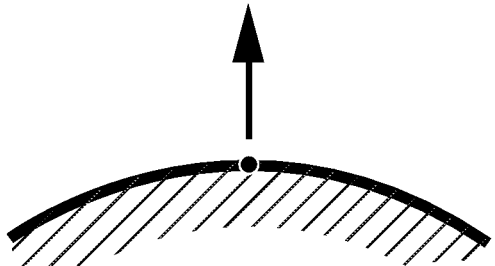
FIG. 3E — Relatively Small Negative Curvature
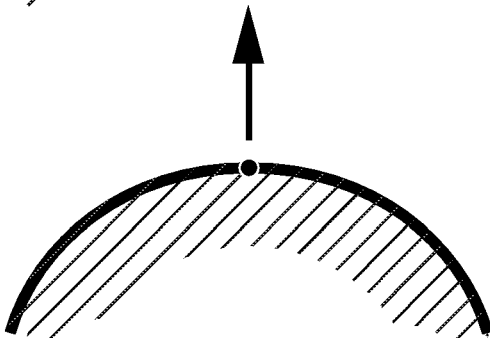
FIG. 3F — Relatively Large Negative Curvature

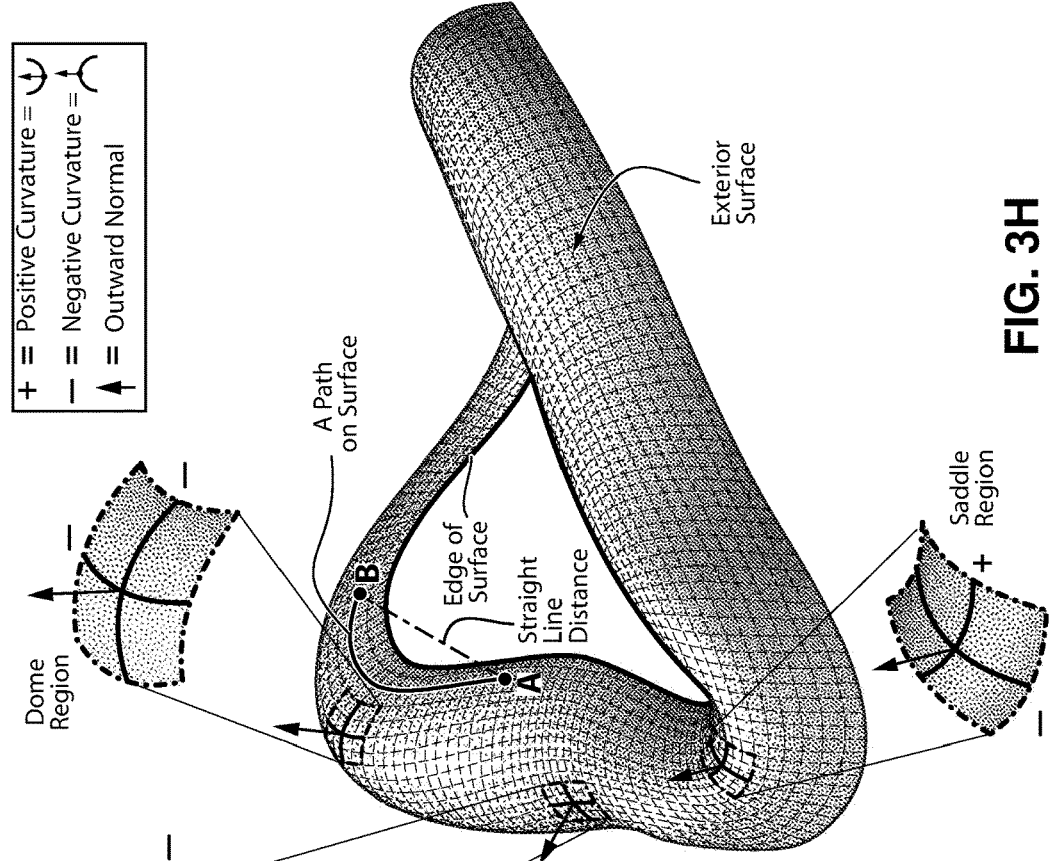
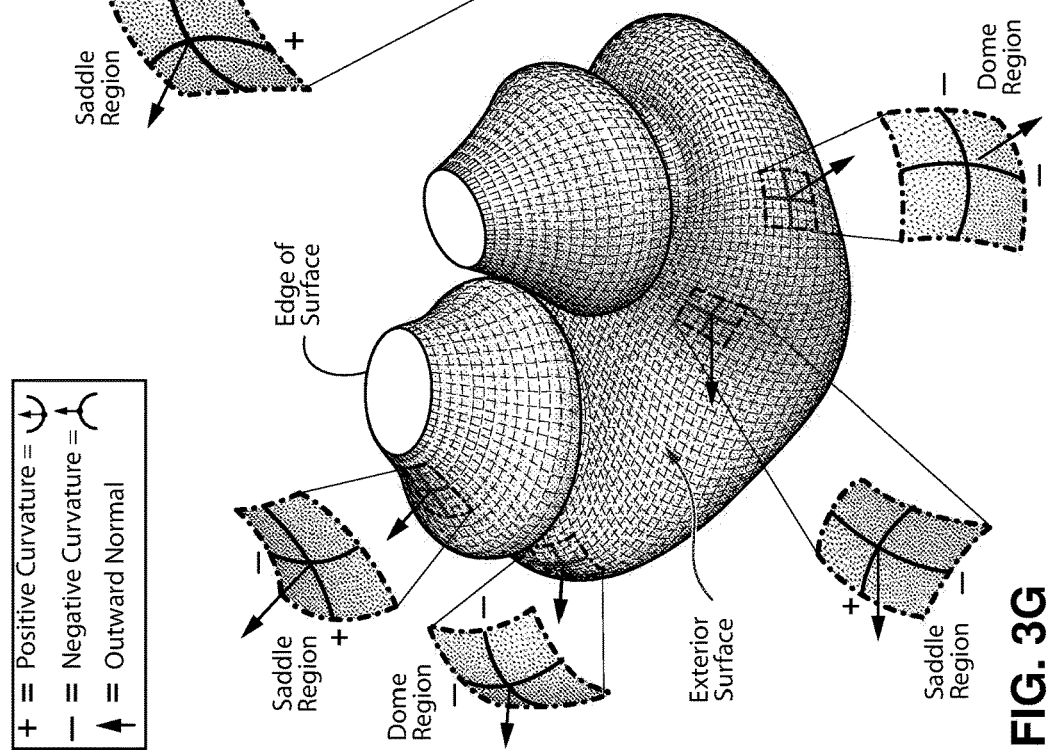
FIG. 3H
FIG. 3G

Copyright 2015 ResMed Limited

Left-hand rule
Right-hand rule
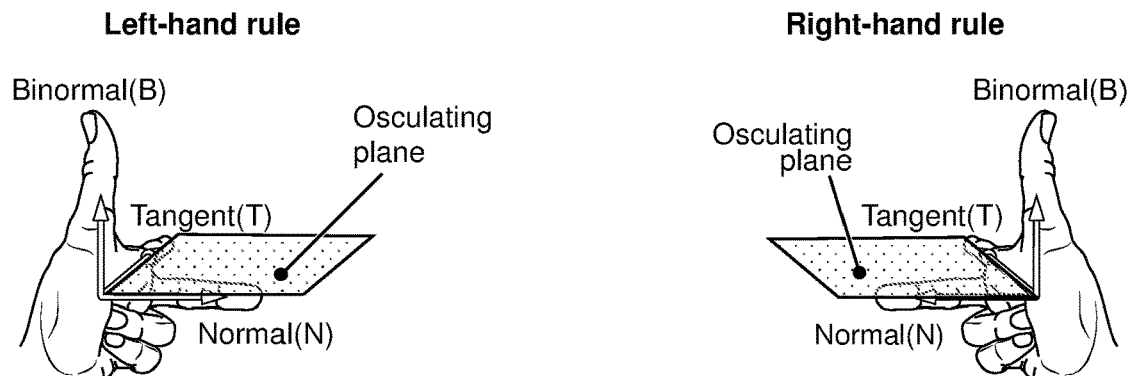
FIG. 3N
FIG. 3O
Left ear helix
Right ear helix
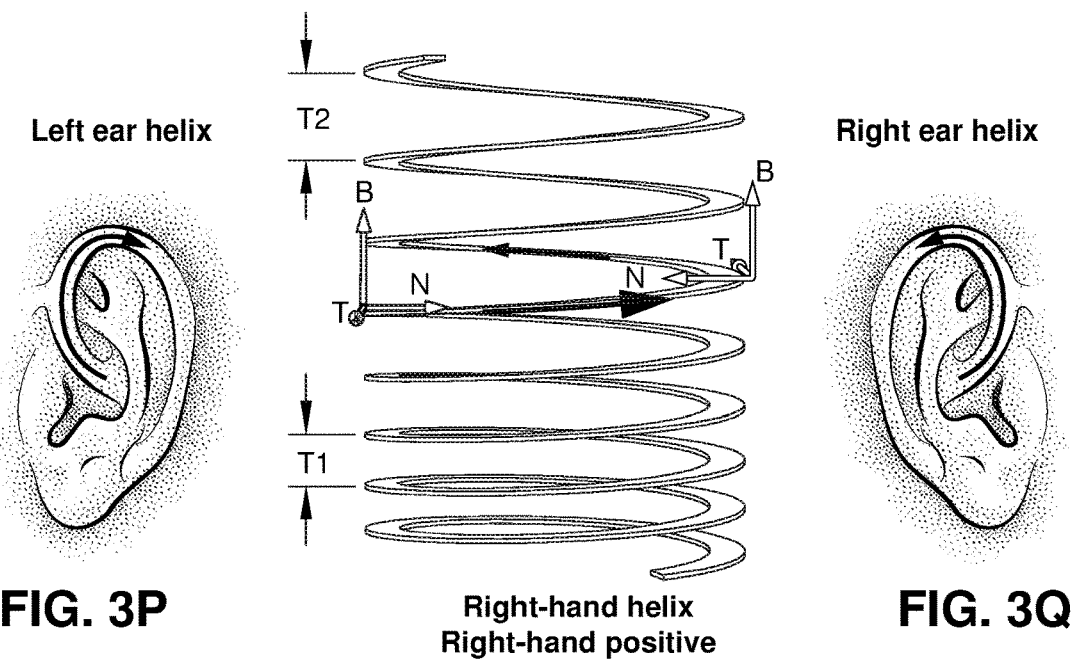
FIG. 3P
Right-hand helix
Right-hand positive
FIG. 3R
FIG. 3Q
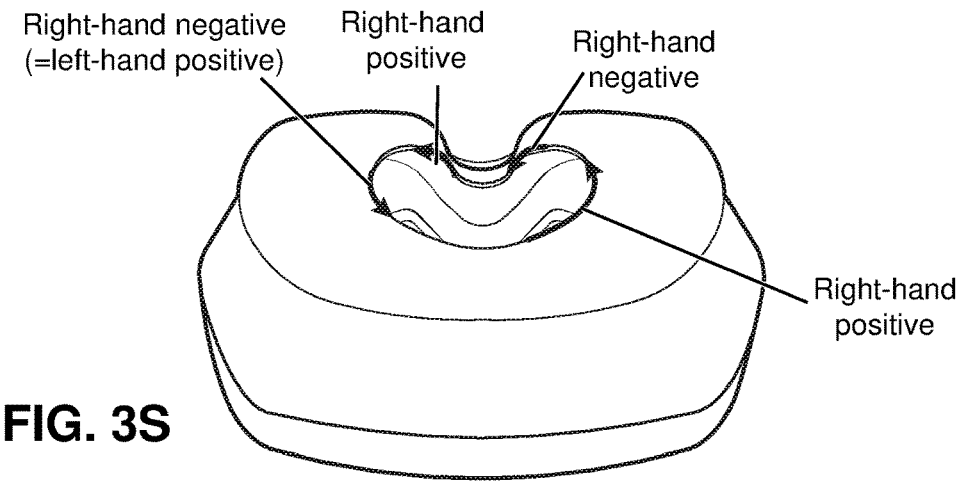
FIG. 3S
Copyright 2015 ResMed Limited

PATIENT INTERFACE WITH VOLUME REDUCING MEMBER

1. CROSS-REFERENCE TO RELATED APPLICATIONS

This application is the U.S. national phase of International Application No. PCT/AU2016/050634 filed 18 Jul. 2016, which designated the U.S. and claims the benefit of U.S. Provisional Application No. 62/194,451, filed Jul. 20, 2015, the entire contents of each of which are hereby incorporated herein by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2. BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the patient's face when force is applied to the patient interface with the seal-forming portion in confronting engagement with the patient's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material positioned about the periphery of the mask so as to provide a self-sealing action against the face of the patient when positive pressure is applied within the mask Like the previous style of seal forming portion, if the match between the face and the mask is not good, additional force may be required to achieve a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris, however some patients find these uncomfortable.

Another form of seal-forming portion may use adhesive to achieve a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063, 328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive nondependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to certain a "compliance rule". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient. The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

| Table of noise of prior masks (ISO 17510-2: 2007, 10 cmH$_2$O pressure at 1 m) | | | | |
| --- | --- | --- | --- | --- |
| Mask name | Mask type | A-weighted sound power level dB(A) (uncertainty) | A-weighted sound pressure dB(A) (uncertainty) | Year (approx.) |
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |

-continued

Table of noise of prior masks (ISO 17510-2: 2007, 10 cmH$_2$O pressure at 1 m)

| | | | | |
|---|---|---|---|---|
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit ™ P10 | nasal pillows | 21 (3) | 13 (3) | 2014 |

(*) one specimen only, measured using test method specified in ISO 3744 in CPAP mode at 10 cmH$_2$O)Sound pressure values of a variety of objects are listed below

| Object | A-weighted sound pressure dB(A) | Notes |
|---|---|---|
| Vacuum cleaner: Nilfisk ® Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Diagnosis and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a person in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home sleep testing.

Clinical experts may be able to diagnose or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

One form of the present technology comprises a patient interface including a plenum chamber and one or more volume reducing members within the plenum chamber to reduce the effective internal volume of the plenum chamber.

Another aspect of one form of the present technology comprises a patient interface including a plenum chamber and structure to reduce an effective internal volume of the plenum chamber to separate unnecessary deadspace volume from volume required to deliver respiratory pressure therapy.

Another aspect of one form of the present technology comprises a patient interface including a plenum chamber and structure to reduce an effective internal volume of the plenum chamber to reduce the volume of $CO_2$ that is rebreathed by the patient.

Another aspect of one form of the present technology comprises a patient interface including a plenum chamber and structure to reduce an effective internal volume of the plenum chamber without altering or impacting the seal forming structure.

Another aspect of one form of the present technology comprises a full-face patient interface including a plenum chamber and structure to separate a main volume of the plenum chamber for delivery of respiratory pressure therapy from unnecessary deadspace volume of the plenum chamber, e.g., unnecessary deadspace volume provided superior the entrance to the patient's nasal passages, inferior the entrance to the patient's mouth, around the sides of the patient's nose and/or mouth, and/or around each of the patient's nasal passages and/or around the patient's mouth.

Another aspect of one form of the present technology comprises a patient interface including a plenum chamber, a heat and moisture exchanger within the plenum chamber and structure to reduce an effective internal volume of the plenum chamber to reduce the volume of $CO_2$ that is rebreathed by the patient.

Another aspect of one form of the present technology relates to a patient interface for sealed delivery of a flow of air at a continuously positive pressure with respect to ambient air pressure to an entrance to the patient's airways including at least entrance of a patient's nares, wherein the patient interface is configured to maintain a therapy pressure in a range of about 4 cmH$_2$O to about 30 cmH$_2$O above ambient air pressure in use, throughout the patient's respiratory cycle, while the patient is sleeping, to ameliorate sleep disordered breathing. The patient interface includes a cushion assembly adapted to form a seal around the patient's nose and/or mouth and a gas washout vent configured to allow a flow of patient exhaled $CO_2$ to an exterior of the patient interface to minimise rebreathing of exhaled $CO_2$ by the patient. The cushion assembly defines a plenum chamber pressurised at a pressure above ambient pressure in use. At least one volume reducing member is provided within the plenum chamber to reduce an effective internal volume of the plenum chamber. The at least one volume reducing member is arranged to separate a main volume of the plenum chamber for delivery of the therapy pressure from deadspace volume provided superior the entrance to the patient's nasal passages and/or inferior the entrance to the patient's mouth. The main volume is adapted to be in direct fluid communication with the patient's nose and/or mouth and the vent.

Another form of the present technology comprises a patient interface including a plenum chamber and at least one flow directing member within the plenum chamber. The plenum chamber has an effective internal volume in fluid communication with a deadspace volume, and the effective internal volume is separated from the deadspace volume by the at least one flow directing member. The at least one flow directing member is structured to obstruct flow between the effective internal volume and the deadspace volume. The effective internal volume may be in direct fluid communication with the entrance to a patient's airways for the delivery of pressurised air thereto. The effective internal volume may comprise a vent for $CO_2$ washout directly from the effective internal volume.

Another form of the present technology comprises a patient interface including a plenum chamber having an effective internal volume in fluid communication with at least one deadspace volume. The effective internal volume is separated from the deadspace volume by at least one flow directing member. The at least one flow directing member is adapted to direct an expiratory flow towards a vent positioned within the plenum chamber. The vent may be positioned in the effective internal volume and separated from the deadspace volume by the at least one flow directing member.

Another aspect of one form of the present technology comprises a patient interface including a seal forming structure and a plenum chamber. The plenum chamber has an effective internal volume in fluid communication with a deadspace volume. The plenum chamber includes at least one flow directing member separating the plenum chamber into an effective internal volume and a deadspace volume. The at least one flow directing member is adapted to obstruct an expiratory flow and an inspiratory flow between the effective internal volume and the deadspace volume of the plenum chamber without altering or impacting the seal forming structure.

Another aspect of one form of the present technology comprises a full-face patient interface including a plenum chamber having an effective internal volume in fluid communication with a deadspace volume. The effective internal volume is separated from the deadspace volume by a flow directing member to obstruct flow between the effective internal volume and the deadspace volume. The deadspace volume of the plenum chamber is provided superior the entrance to the patient's nasal passages, inferior the entrance to the patient's mouth, around the sides of the patient's nose and/or mouth, and/or around each of the patient's nasal passages and/or around the patient's mouth.

Another aspect of one form of the present technology comprises a full-face patient interface including a plenum chamber and at least one flow directing member. The at least one flow directing member separates the plenum chamber into a main volume for delivery of respiratory pressure therapy and an unnecessary deadspace volume. The at least one flow directing member is adapted to obstruct expiratory flow flowing into the deadspace volume.

Another aspect of one form of the present technology comprises a patient interface including a plenum chamber and at least one flow directing member separating the plenum chamber into an effective internal volume and at least one deadspace volume. The effective internal volume comprises a HME and a vent for $CO_2$ washout. The at least one flow directing member is adapted to obstruct an expiratory flow flowing from the effective internal volume into the deadspace volume, and the at least one flow directing member is adapted to direct an expiratory flow through the HME prior to exiting through the vent. The flow directing member may direct the expiratory flow away from the seal forming member prior to flowing through the HME to reduce moisture loss from expiration.

Another aspect of one form of the present technology comprises a patient interface including a plenum chamber and flow directing member separating the plenum chamber into an effective internal volume and at least one deadspace volume. The at least one deadspace volume is provided adjacent a seal forming portion of the patient interface. The deadspace volume surrounds the effective internal volume, and the effective internal volume is adapted to surround the entrance of the patient's airways including the nares and/or the mouth. The effective internal volume may be in direct fluid communication with an inlet of the patient interface. The deadspace volume may be in fluid communication with a vent for $CO_2$ washout via the effective internal volume.

Another aspect of one form of the present technology comprises a patient interface including a seal forming member, a plenum chamber and at least one flow directing member dividing the plenum chamber into an effective internal volume for delivery of pressurised air to the entrance of a patient's airways and at least one deadspace volume. The effective internal volume comprises a HME and a vent for $CO_2$ washout. The flow directing member is adapted to obstruct an expiratory flow from flowing into the deadspace volume prior to flowing through the HME. The deadspace volume may comprise at least a portion of the seal forming member. The flow directing member may be adapted to direct the expiratory flow towards the HME prior to entering the deadspace volume to prevent moisture loss from leak from an incomplete seal caused by the seal forming member.

Another aspect of one form of the present technology comprises a patient interface including a seal forming member, a plenum chamber and at least one flow directing member separating the plenum chamber into an effective internal volume for the delivery pressurised air to the patient's airways and at least one deadspace volume. The effective internal volume comprises a HME and a vent for $CO_2$ washout. The flow directing member is adapted to obstruct an inspiratory flow from flowing into the deadspace volume prior to delivery to the patient's airways. The deadspace volume may comprise at least a portion of the seal forming member. The flow directing member may be adapted to direct the inspiratory flow towards the HME prior to entering the deadspace volume to prevent moisture loss from leak via an incomplete seal caused by the seal forming member.

Another aspect of one form of the present technology relates to a patient interface for sealed delivery of a flow of air at a continuously positive pressure with respect to ambient air pressure to an entrance to the patient's airways including at least entrance of a patient's nares, wherein the patient interface is configured to maintain a therapy pressure in a range of about 4 $cmH_2O$ to about 30 $cmH_2O$ above ambient air pressure in use, throughout the patient's respiratory cycle, while the patient is sleeping, to ameliorate sleep disordered breathing. The patient interface includes a cushion assembly adapted to form a seal around the patient's nose and/or mouth and a gas washout vent configured to allow a flow of patient exhaled $CO_2$ to an exterior of the patient interface to minimise rebreathing of exhaled $CO_2$ by the patient. The cushion assembly defines a plenum chamber pressurised at a pressure above ambient pressure in use. At least one flow directing member is provided within the plenum chamber to separate the plenum chamber into an effective internal volume surrounding the entrance of the patient's airways, and a deadspace volume at least partially surrounding the effective internal volume. The deadspace volume is formed partially by at least a portion of the cushion assembly. The at least one flow directing member is arranged to direct the inspiratory and expiratory flow from flowing into the deadspace volume. The deadspace volume of the plenum chamber may be provided superior the entrance to the patient's nasal passages, inferior the entrance to the patient's mouth, around the sides of the patient's nose and/or mouth, and/or around each of the patient's nasal passages and/or around the patient's mouth.

An aspect of certain forms of the present technology is a medical device that is easy to use, e.g. by a person who does not have medical training, by a person who has limited dexterity, vision or by a person with limited experience in using this type of medical device.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of a nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown.

4.2 Respiratory System and Facial Anatomy

Figure 2A:
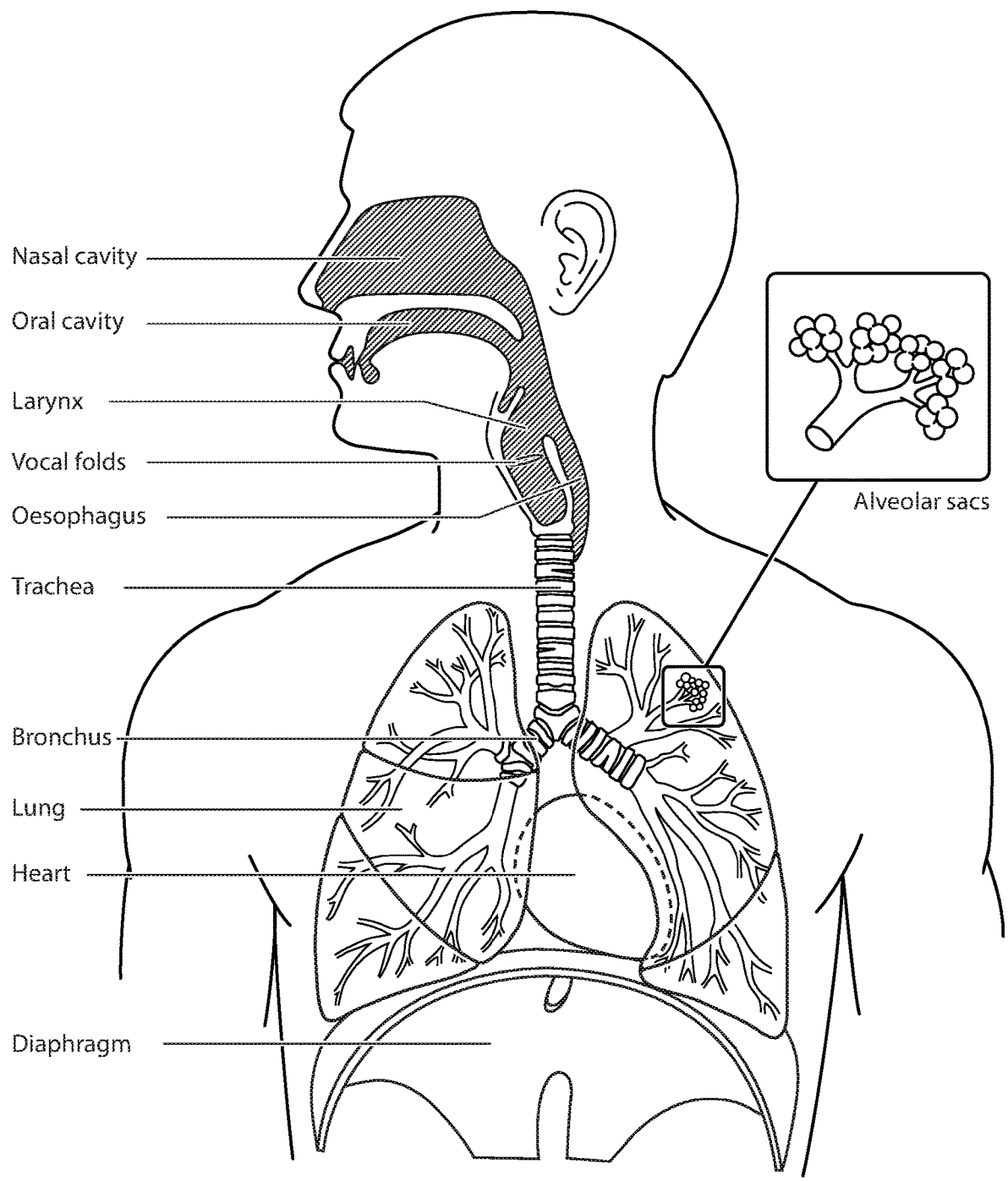

FIG. 2A shows an overview of a human respiratory system including the nasal and oral cavities, the larynx, vocal folds, oesophagus, trachea, bronchus, lung, alveolar sacs, heart and diaphragm.

Figure 2B:
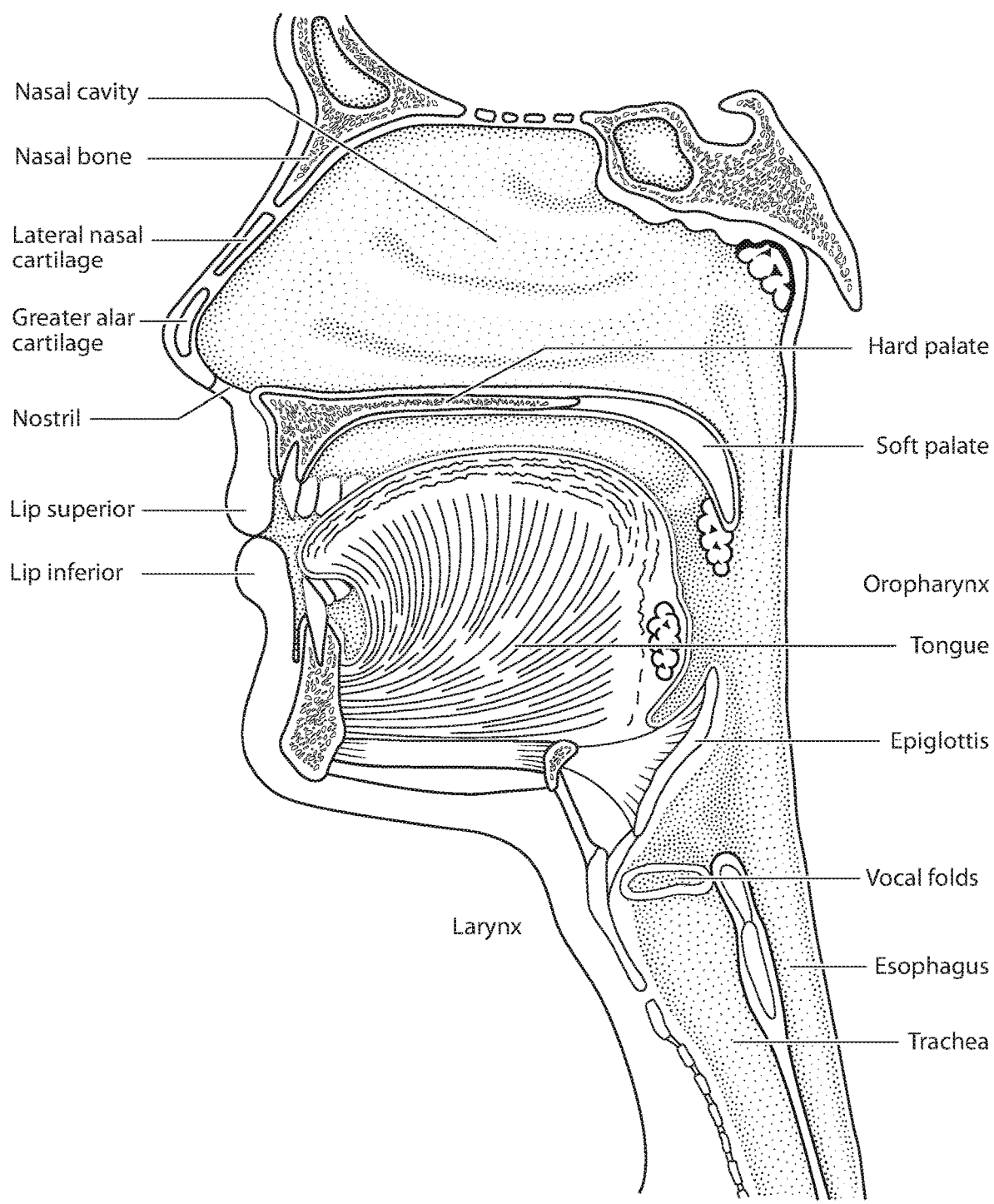

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
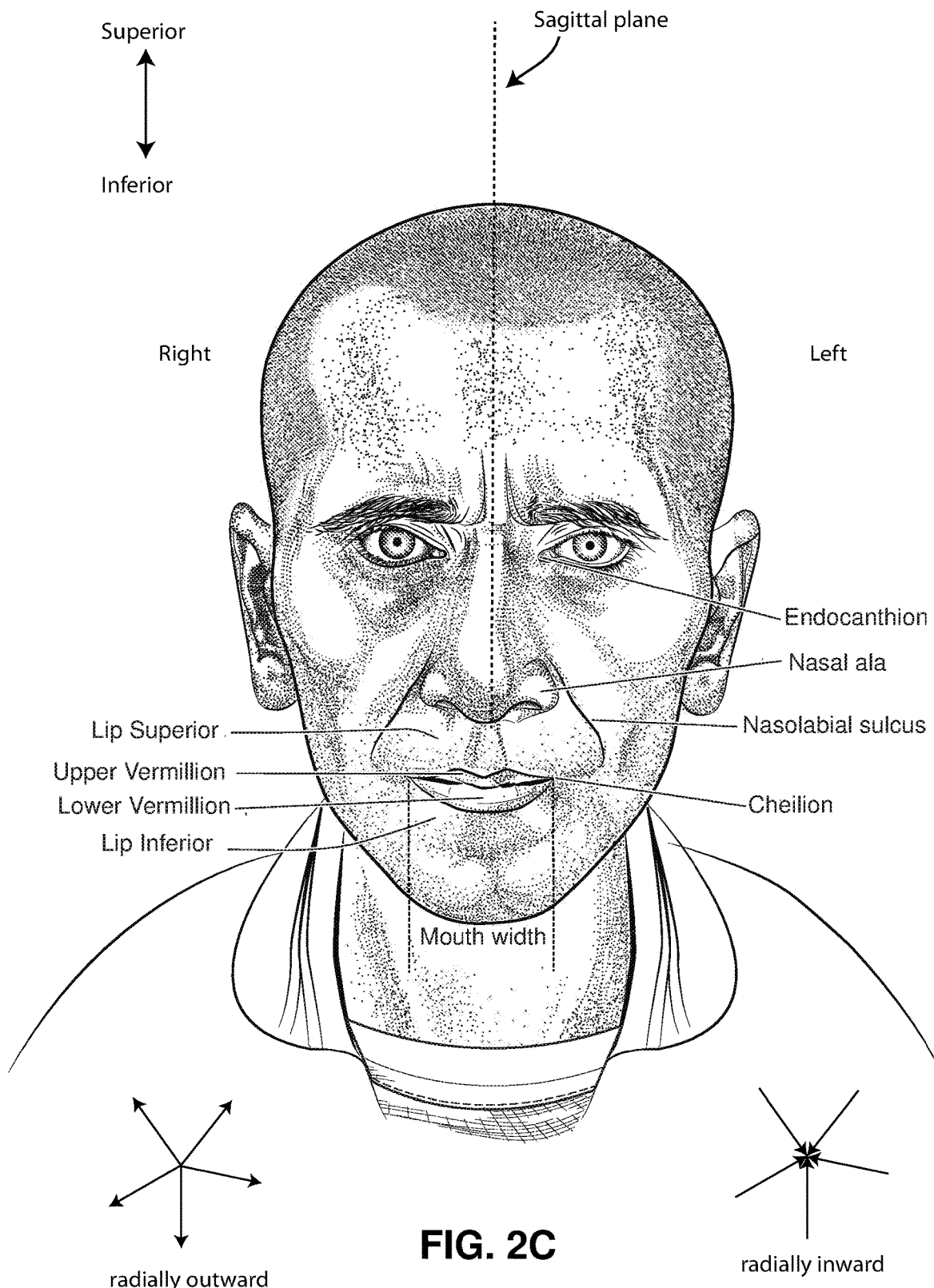

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
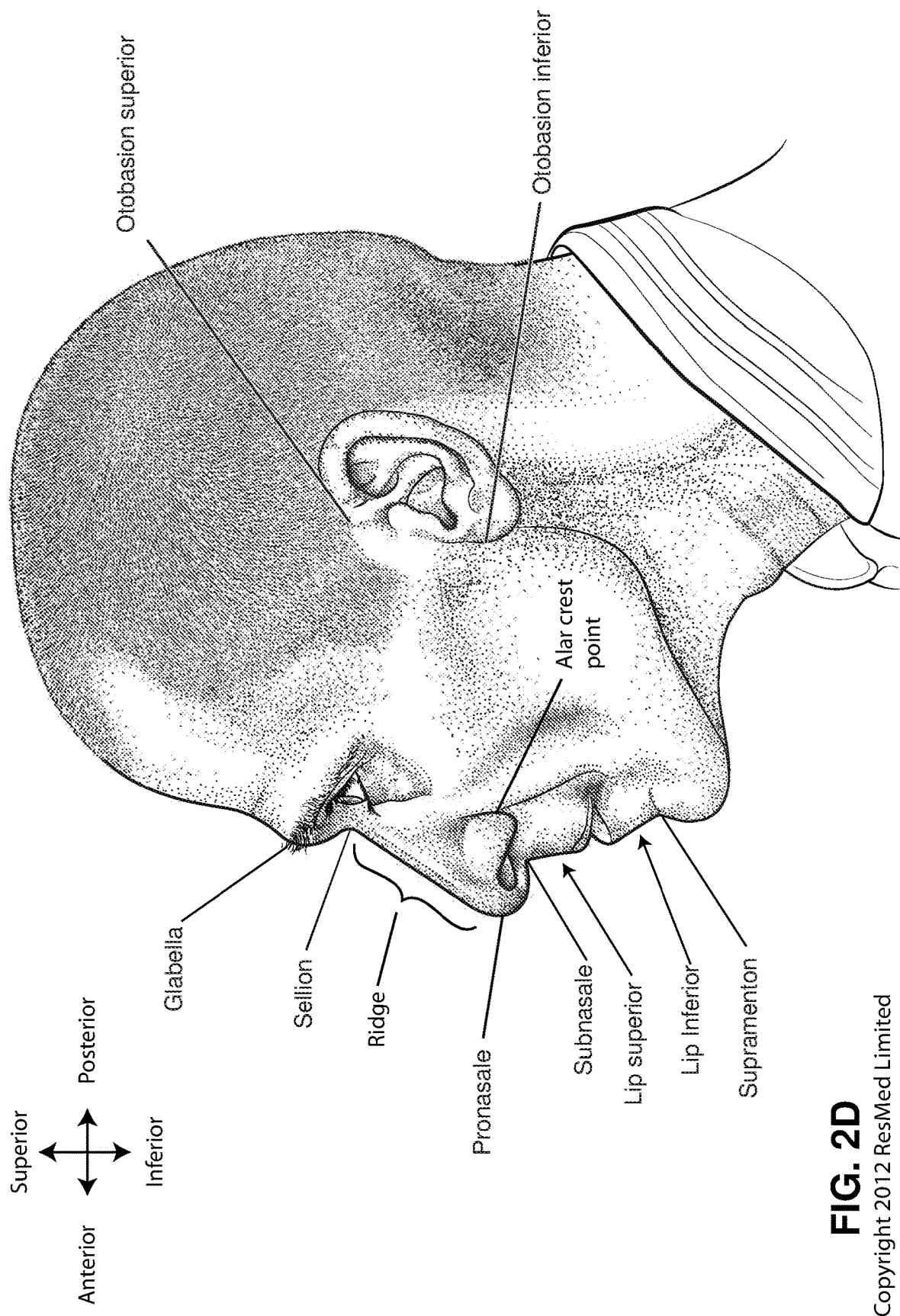

FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
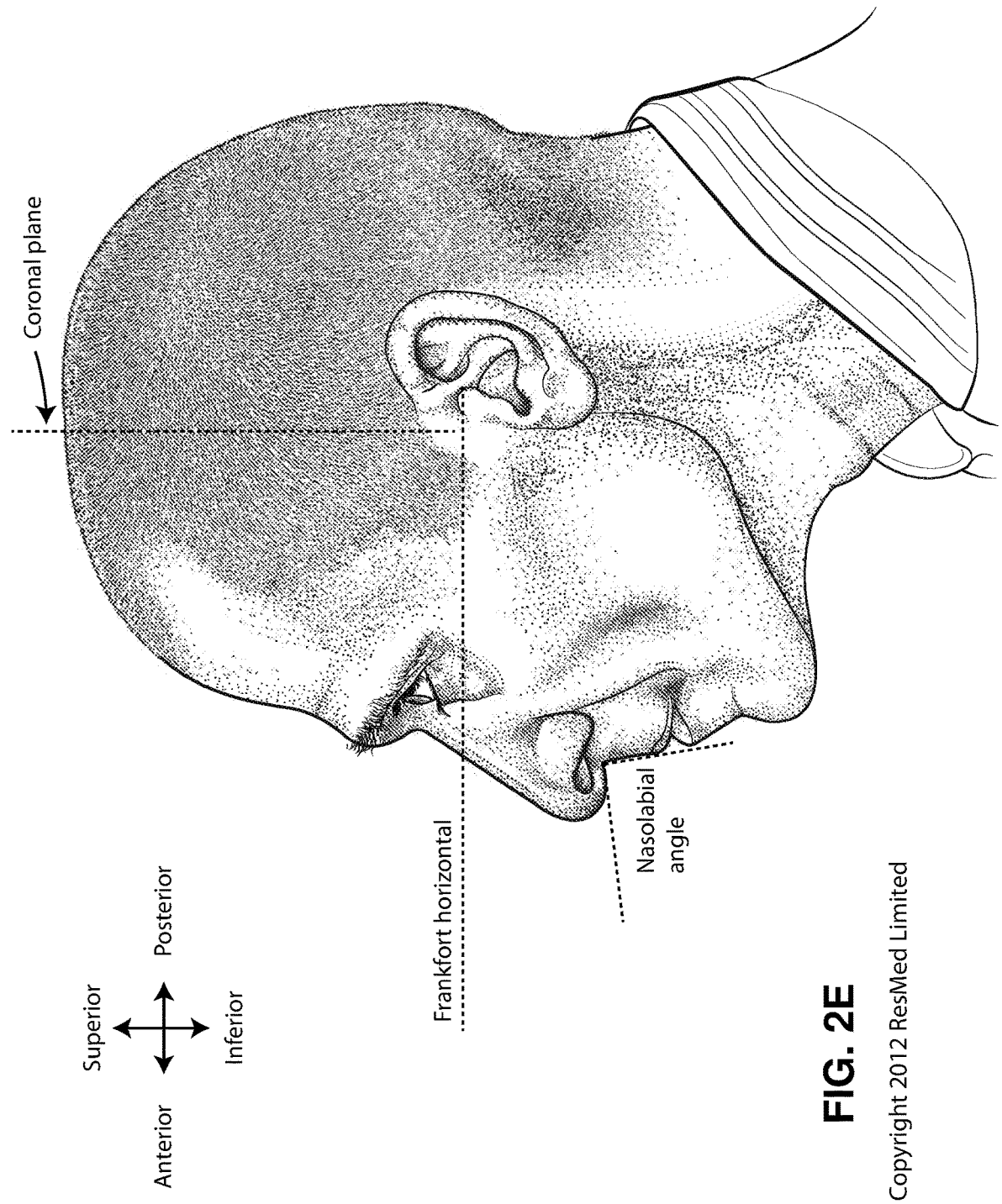

FIG. 2E is a further side view of a head. The approximate locations of the Frankfort horizontal and nasolabial angle are indicated. The coronal plane is also indicated.

Figure 2F:
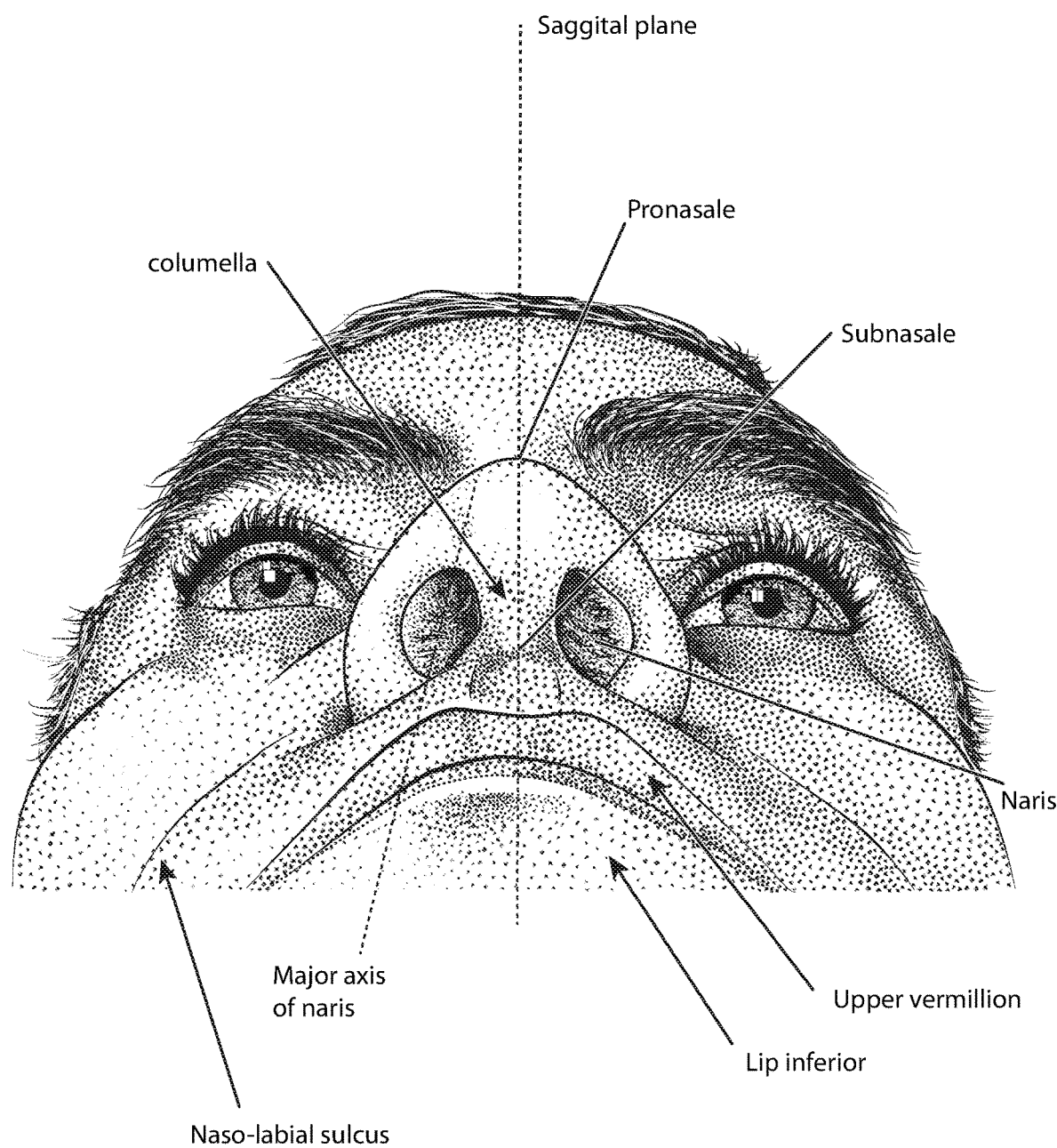

FIG. 2F shows a base view of a nose with several features identified including naso-labial sulcus, lip inferior, upper Vermilion, naris, subnasale, columella, pronasale, the major axis of a naris and the sagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from a sagittal plane, amongst other things showing the septum cartilage and medial crus of greater alar cartilage.

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
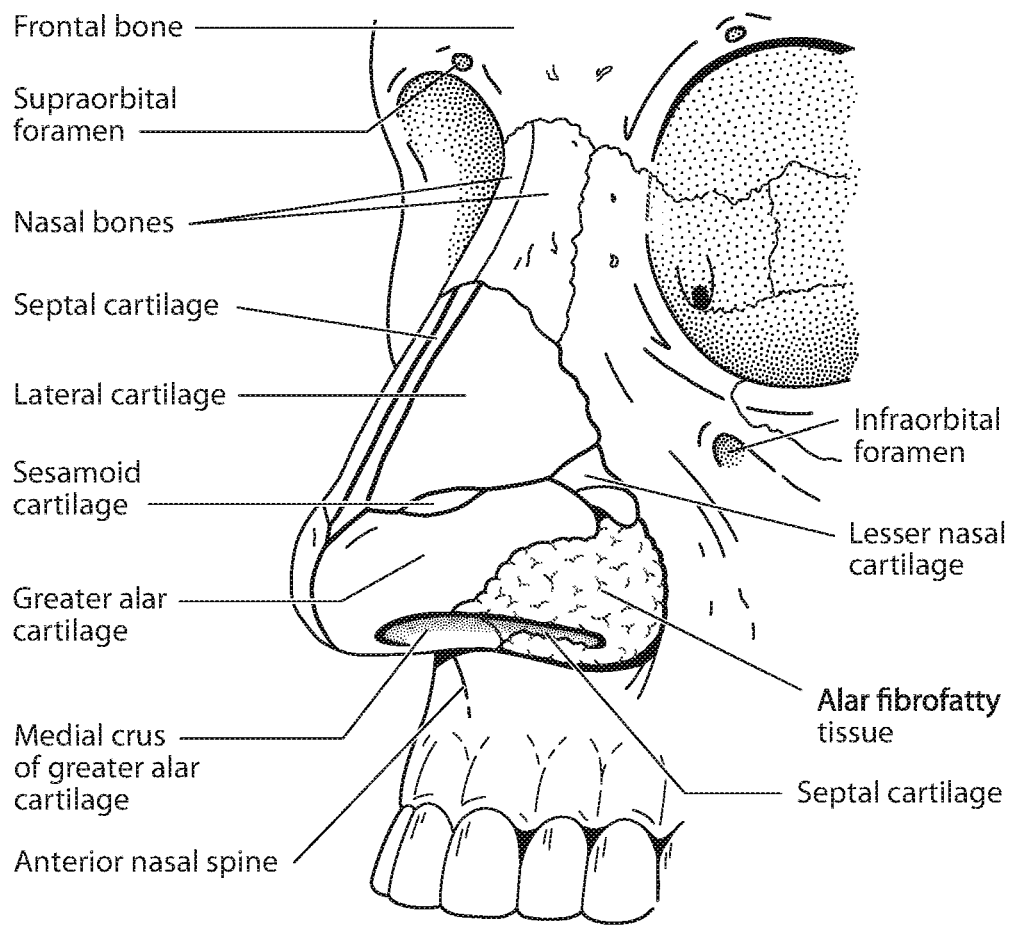

FIG. 2L shows an anterolateral view of a nose.

4.3 Patient Interface

Figure 3A:
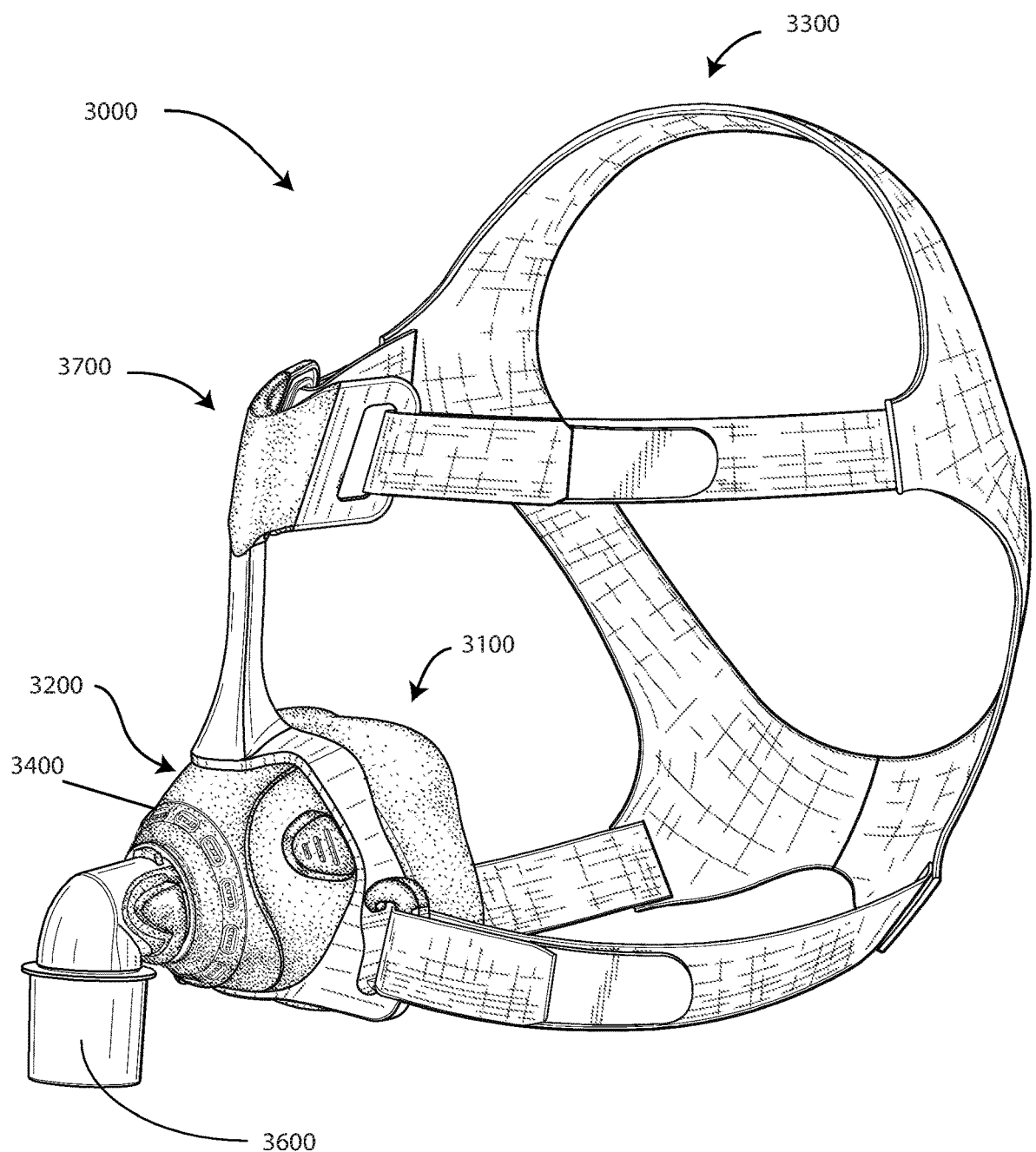

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
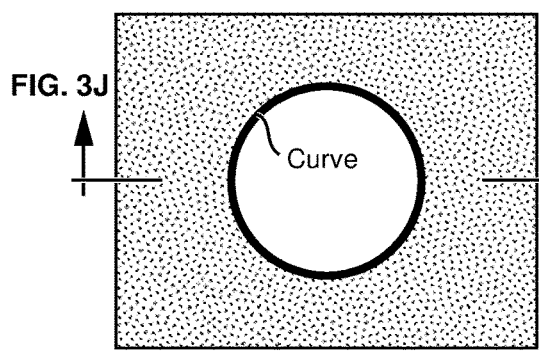

FIG. 3I shows the surface of a structure, with a one dimensional hole in the surface. Plane curve 301D forms the boundary of a one dimensional hole.

Figure 3K:
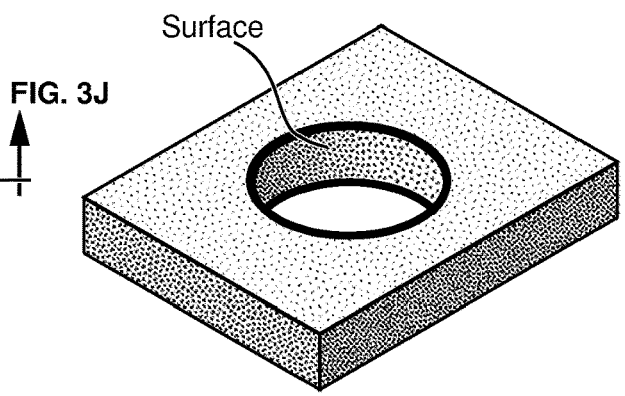
Figure 3J:
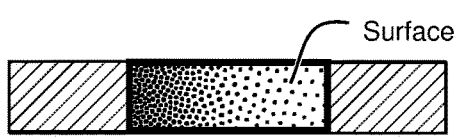

FIG. 3J shows a cross-section through the structure of FIG. 3I. Surface 302D that bounds a two dimensional hole in the structure of FIG. 3I is indicated.

FIG. 3K shows a perspective view of the structure of FIG. 3I, including the two dimensional hole and the one dimensional hole. Surface 302D that bounds a two dimensional hole in the structure of FIG. 3I is indicated.

Figure 3L:
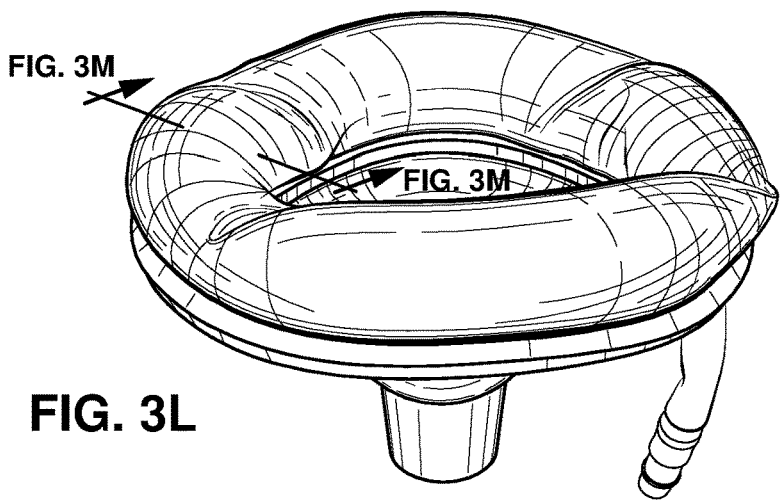

FIG. 3L shows a mask having an inflatable bladder as a cushion.

Figure 3M:
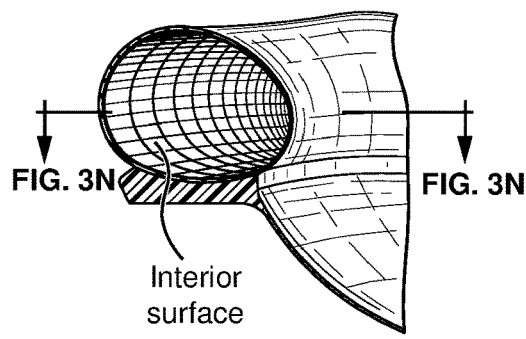

FIG. 3M shows a cross-section through the mask of FIG. 3L, and shows the inside surface of the bladder.

FIG. 3N illustrates a left-hand rule.

FIG. 3O illustrates a right-hand rule.

FIG. 3P shows a left ear, including a left ear helix.

FIG. 3Q shows a right ear, including a right ear helix.

FIG. 3R shows a right-hand helix.

FIG. 3S shows a view of a mask, including the sign of the torsion of the space curve defined by the edge of the sealing membrane in different regions of the mask.

4.4 Volume Reducing Member for Patient Interface

Figure 4:
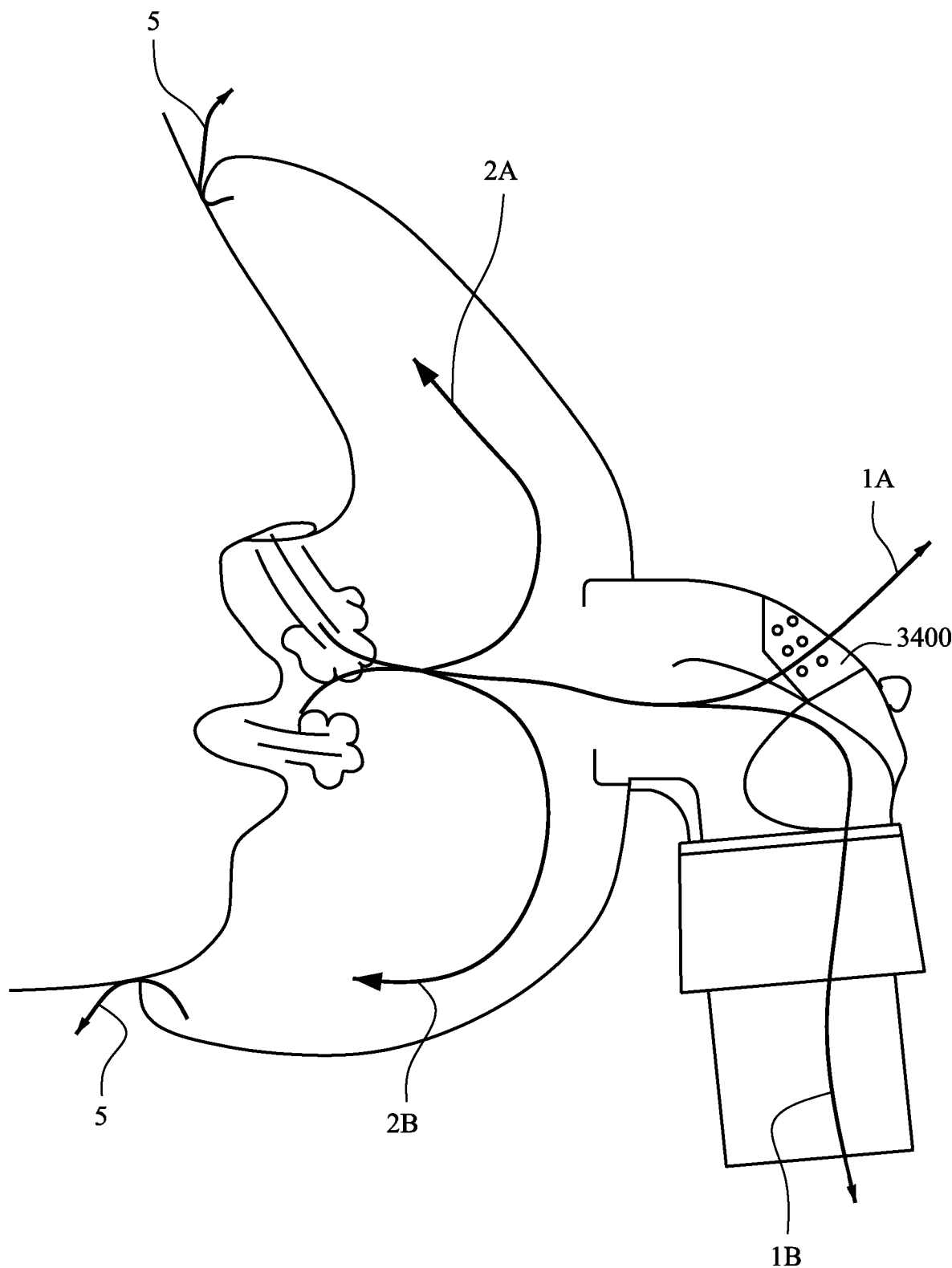

FIG. 4 is a schematic side view of a full-face mask showing exemplary air flow paths during patient expiration.

Figure 5:
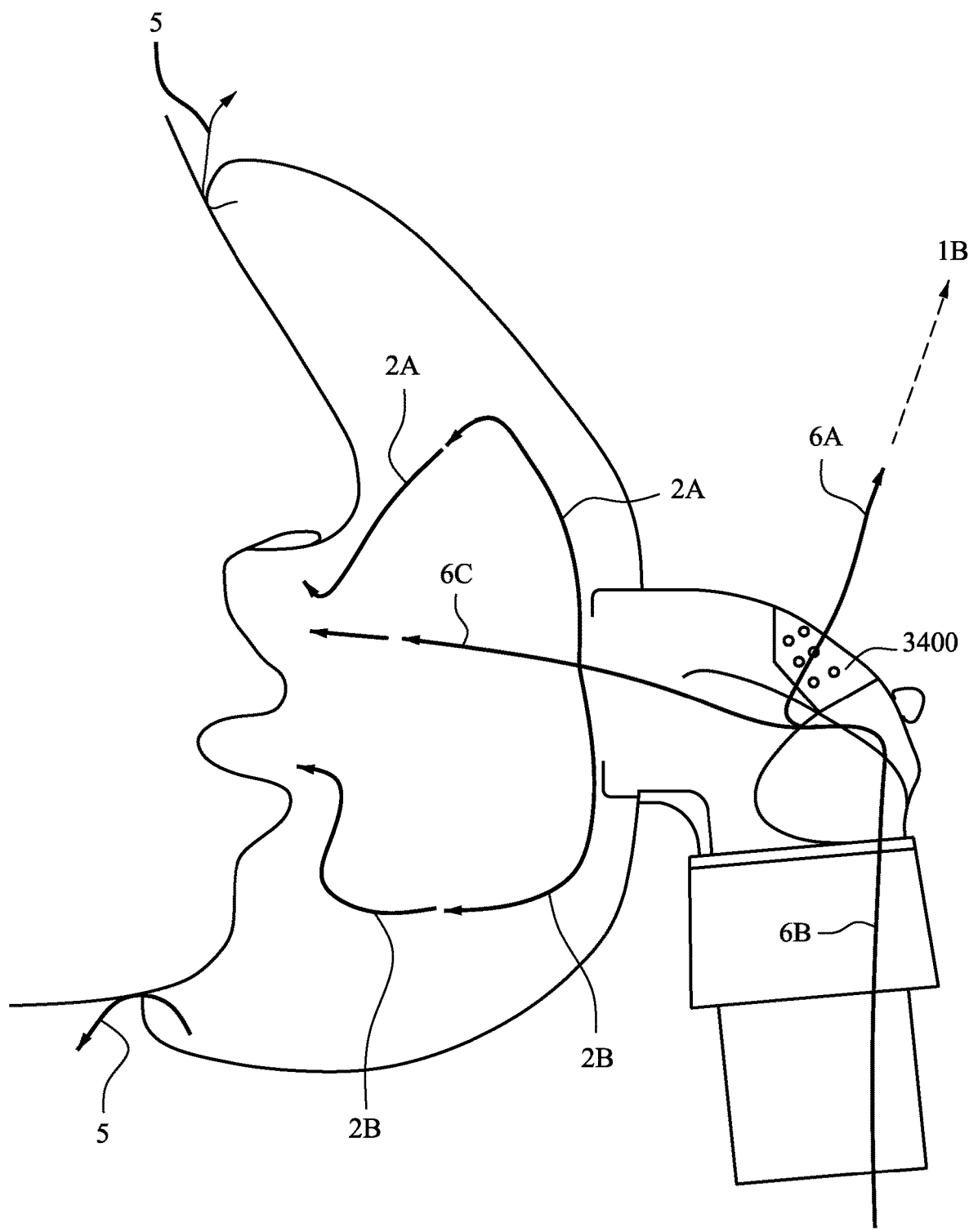

FIG. 5 is a schematic side view of a full-face mask showing exemplary air flow paths during patient inspiration.

Figure 6:
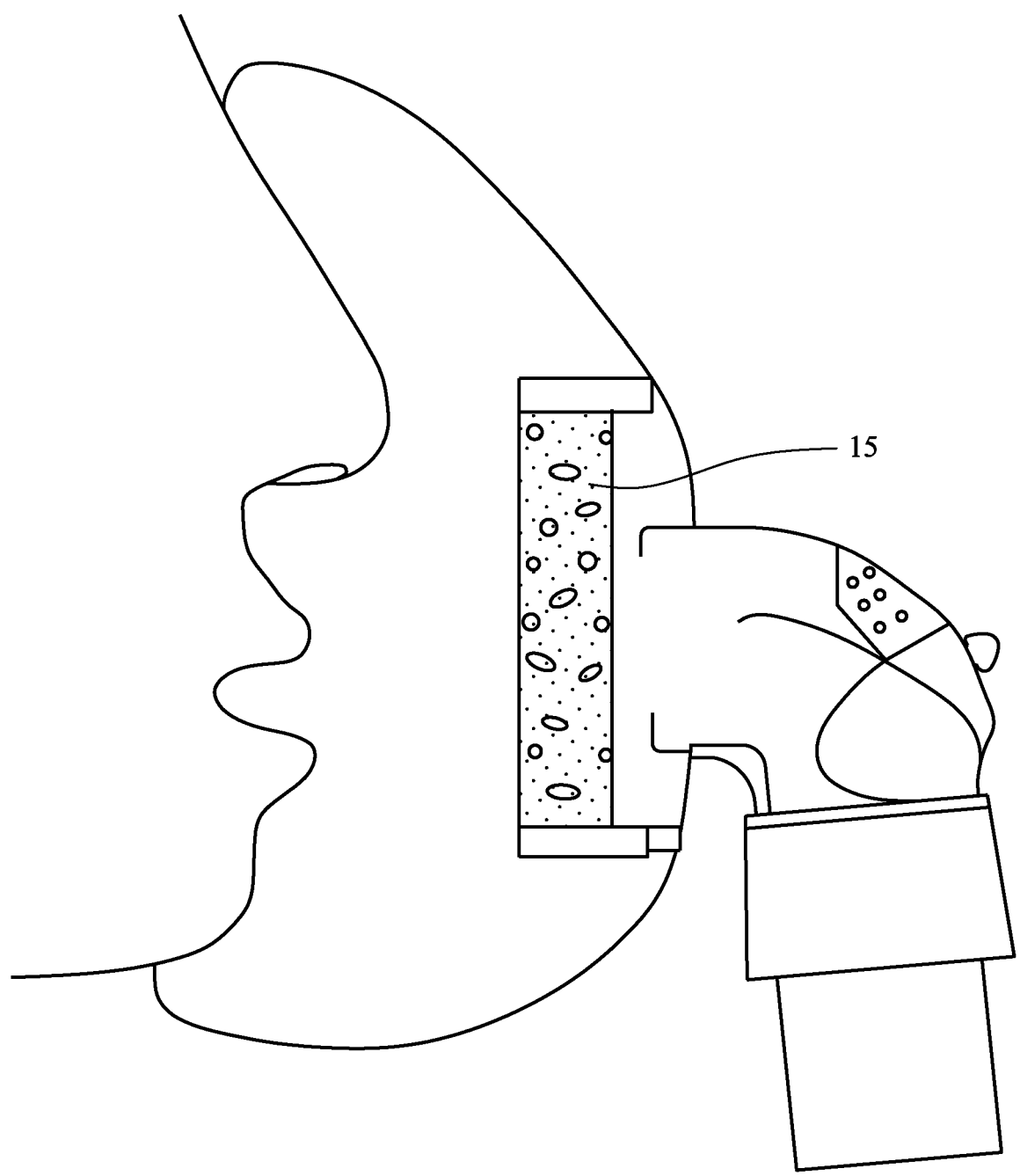

FIG. 6 is a schematic side view of a full-face mask including a HME.

Figure 7:
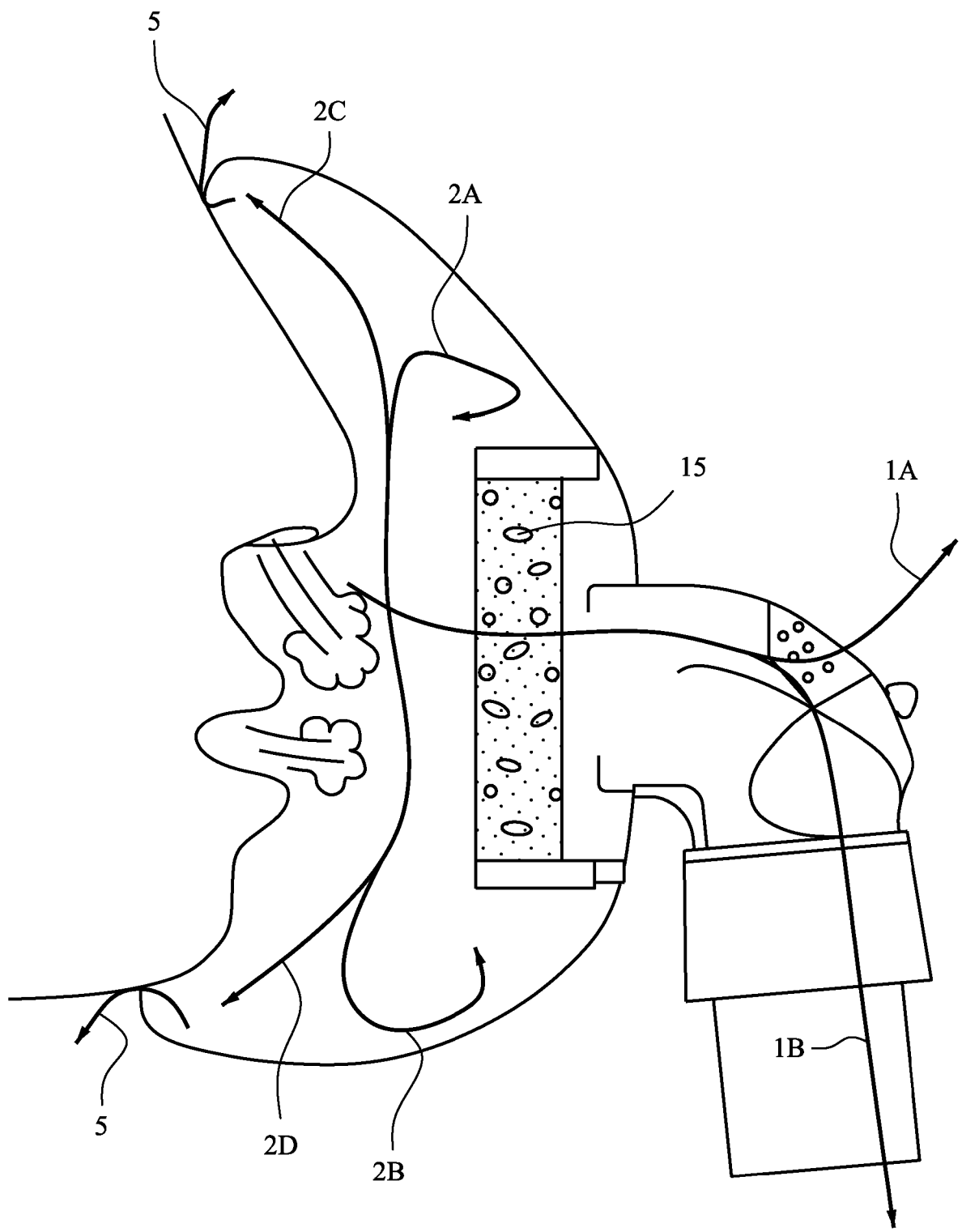

FIG. 7 is a schematic side view of a full-face mask including a HME showing exemplary air flow paths during patient expiration.

Figure 8:
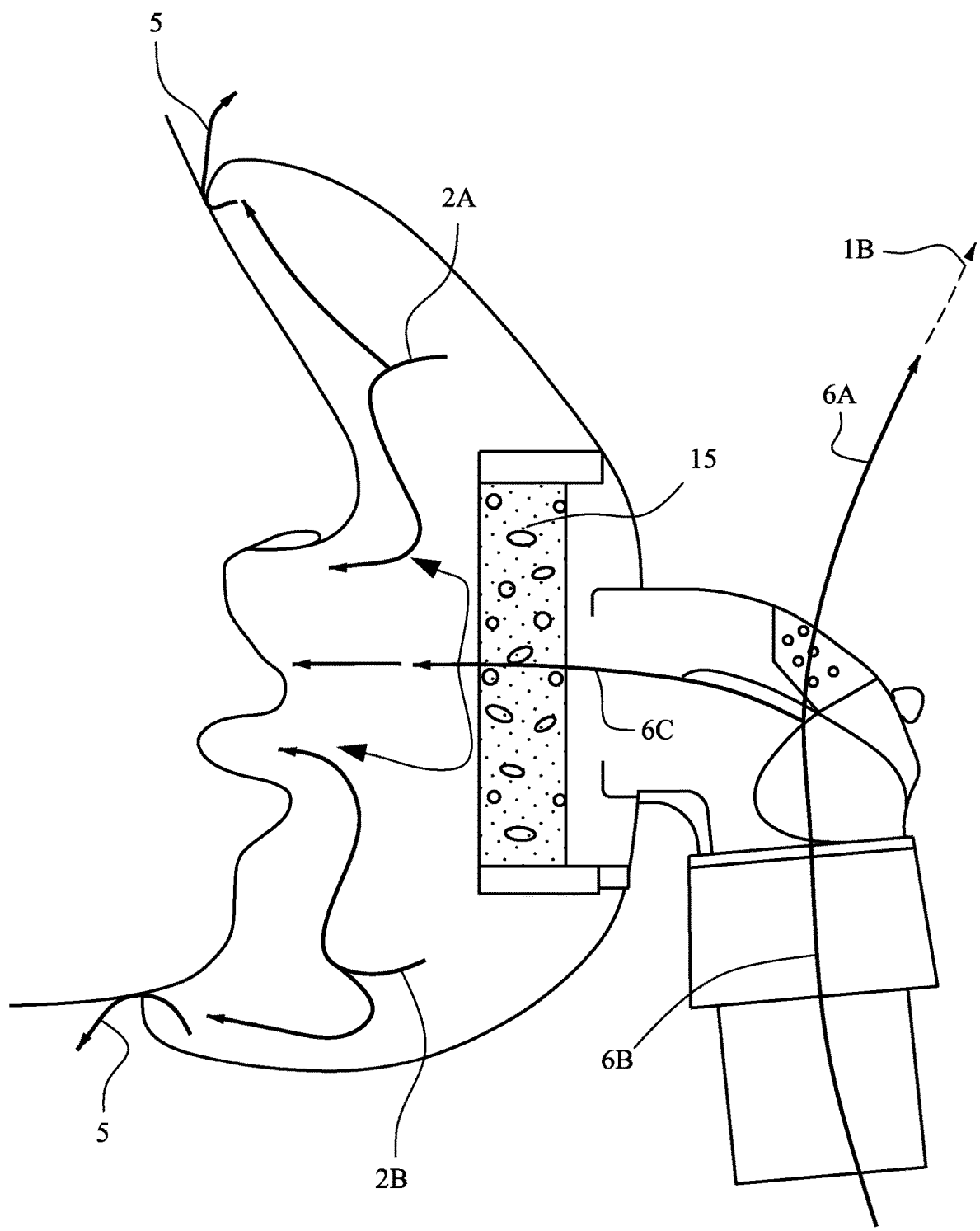

FIG. 8 is a schematic side view of a full-face mask including a HME showing exemplary air flow paths during patient inspiration.

Figure 9:
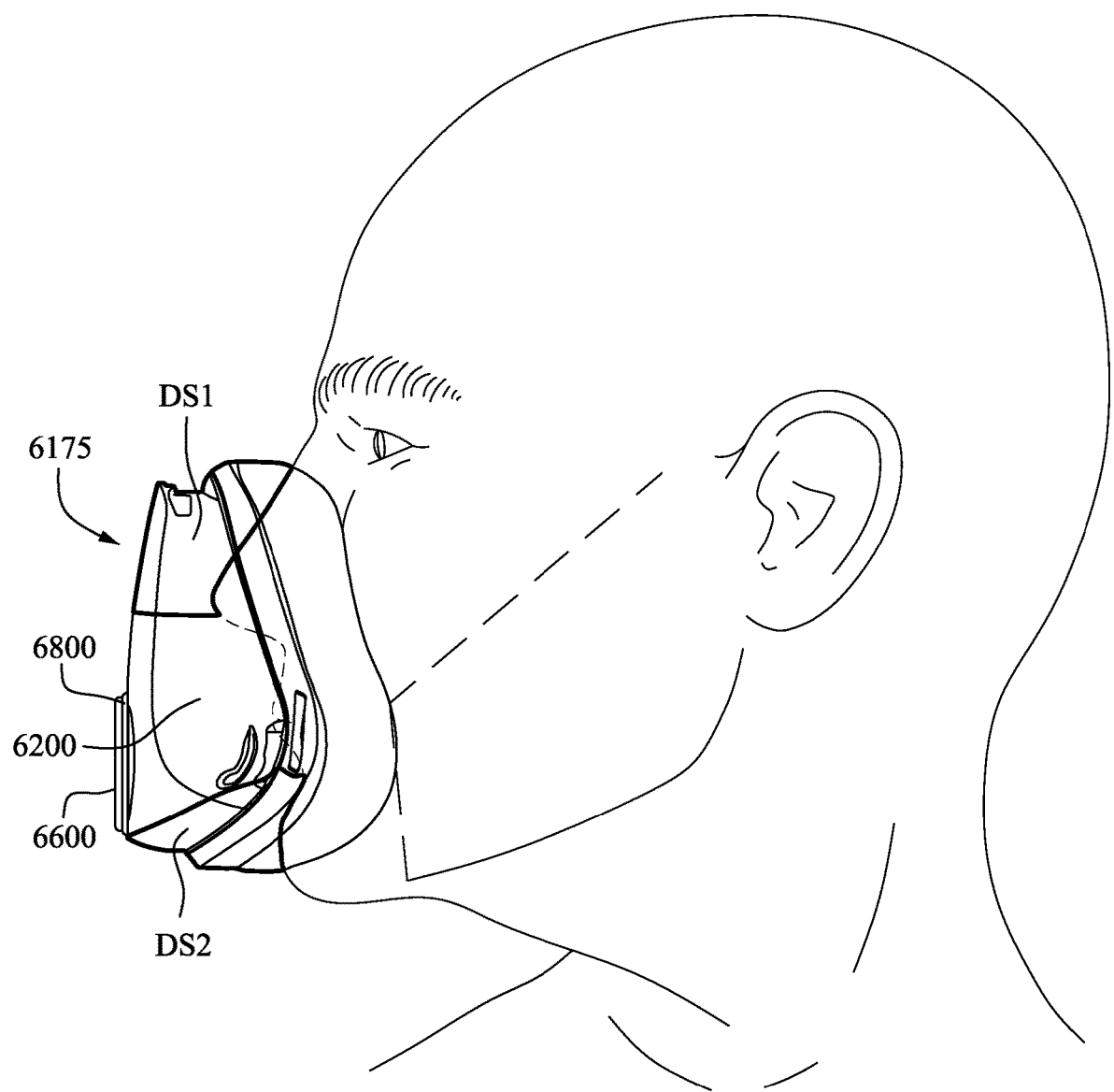

FIG. 9 is a side view showing exemplary deadspace volumes in the plenum chamber of a cushion assembly according to an example of the present technology.

Figure 10:
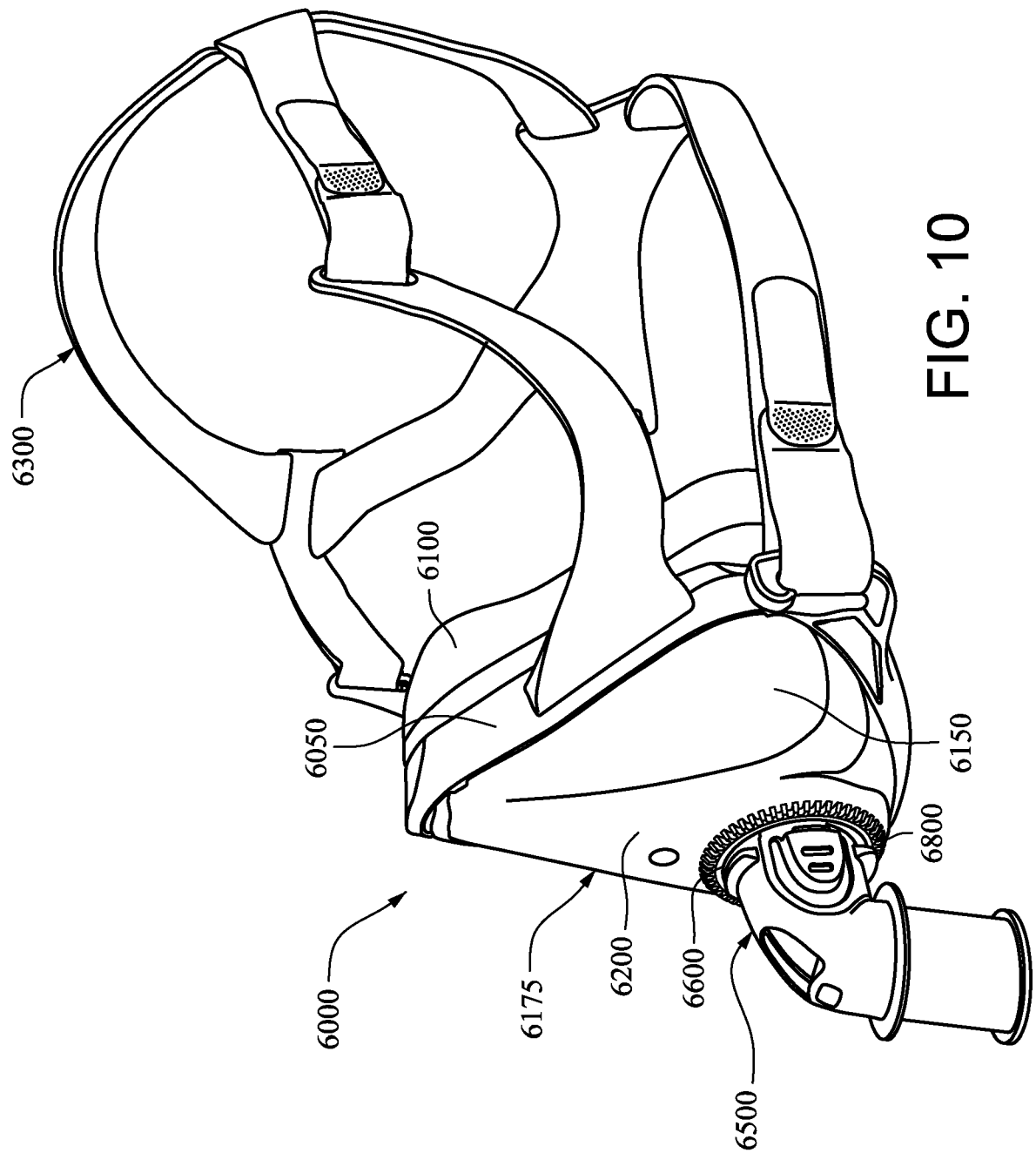

FIG. 10 is a perspective view a patient interface in the form of a full-face mask in accordance with one form of the present technology.

Figure 11:
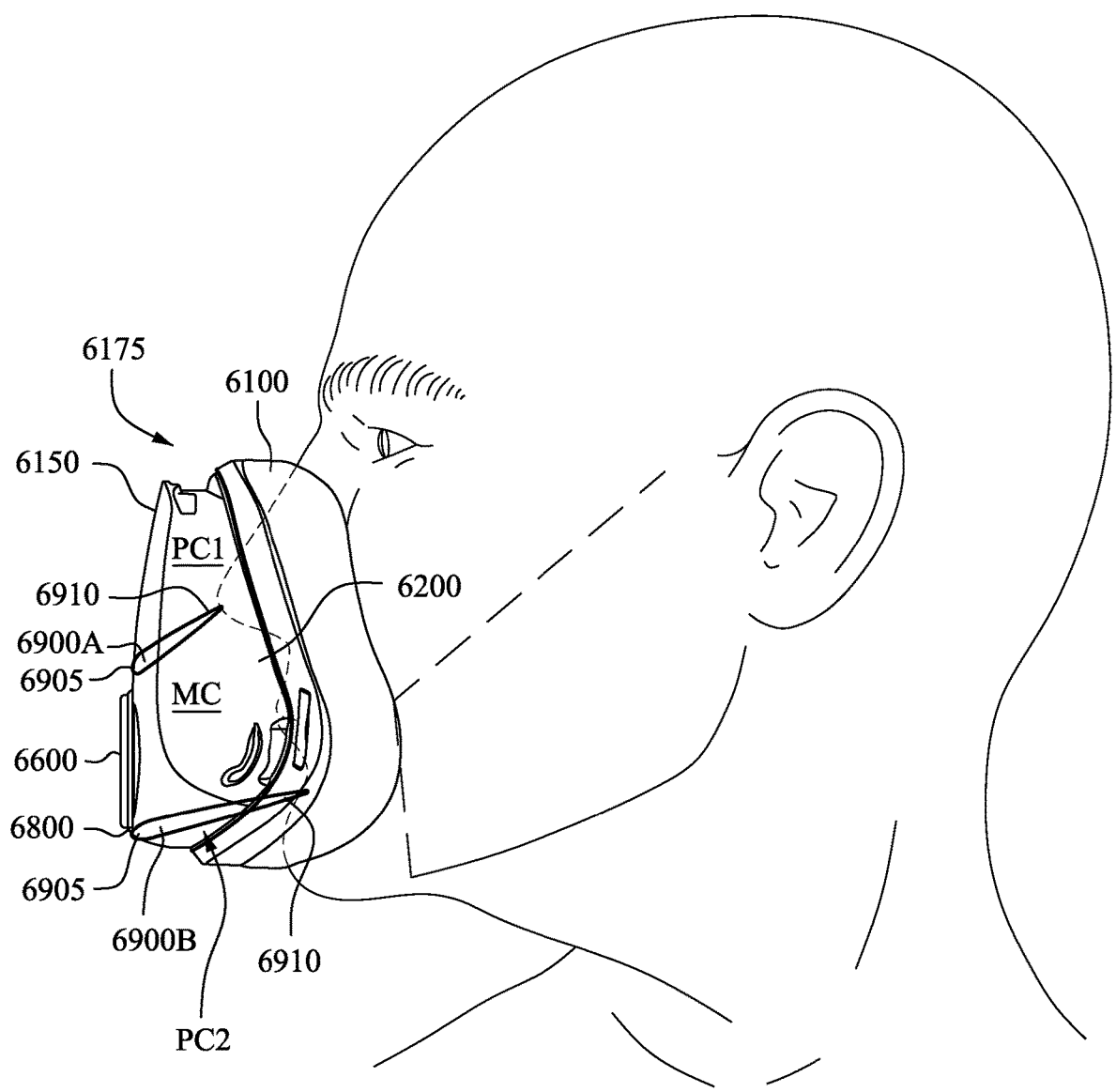

FIG. 11 is a side view showing a cushion assembly including volume reducing members according to an example of the present technology.

Figure 12:
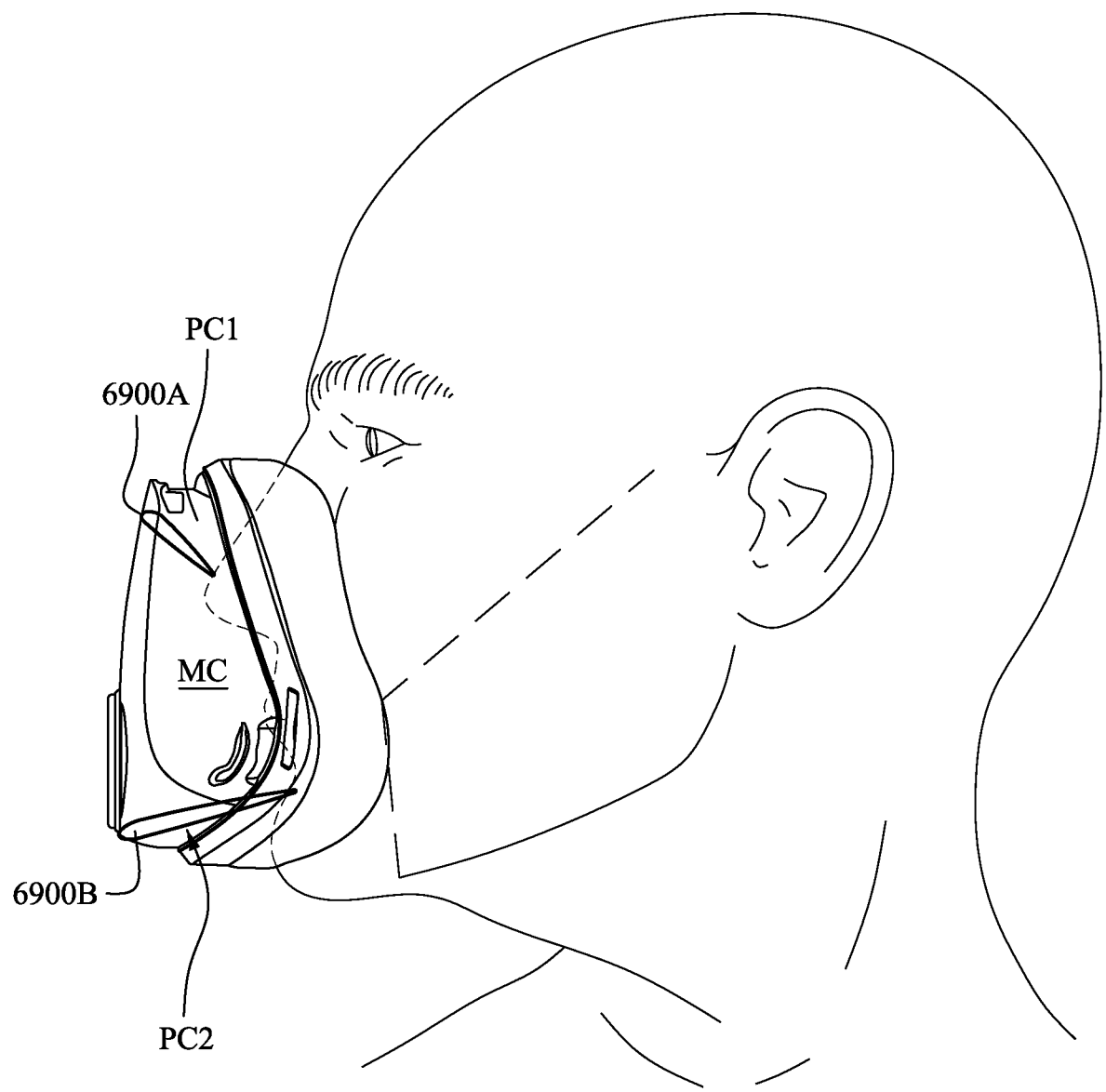

FIG. 12 is a side view showing a cushion assembly including volume reducing members according to another example of the present technology.

Figure 13:
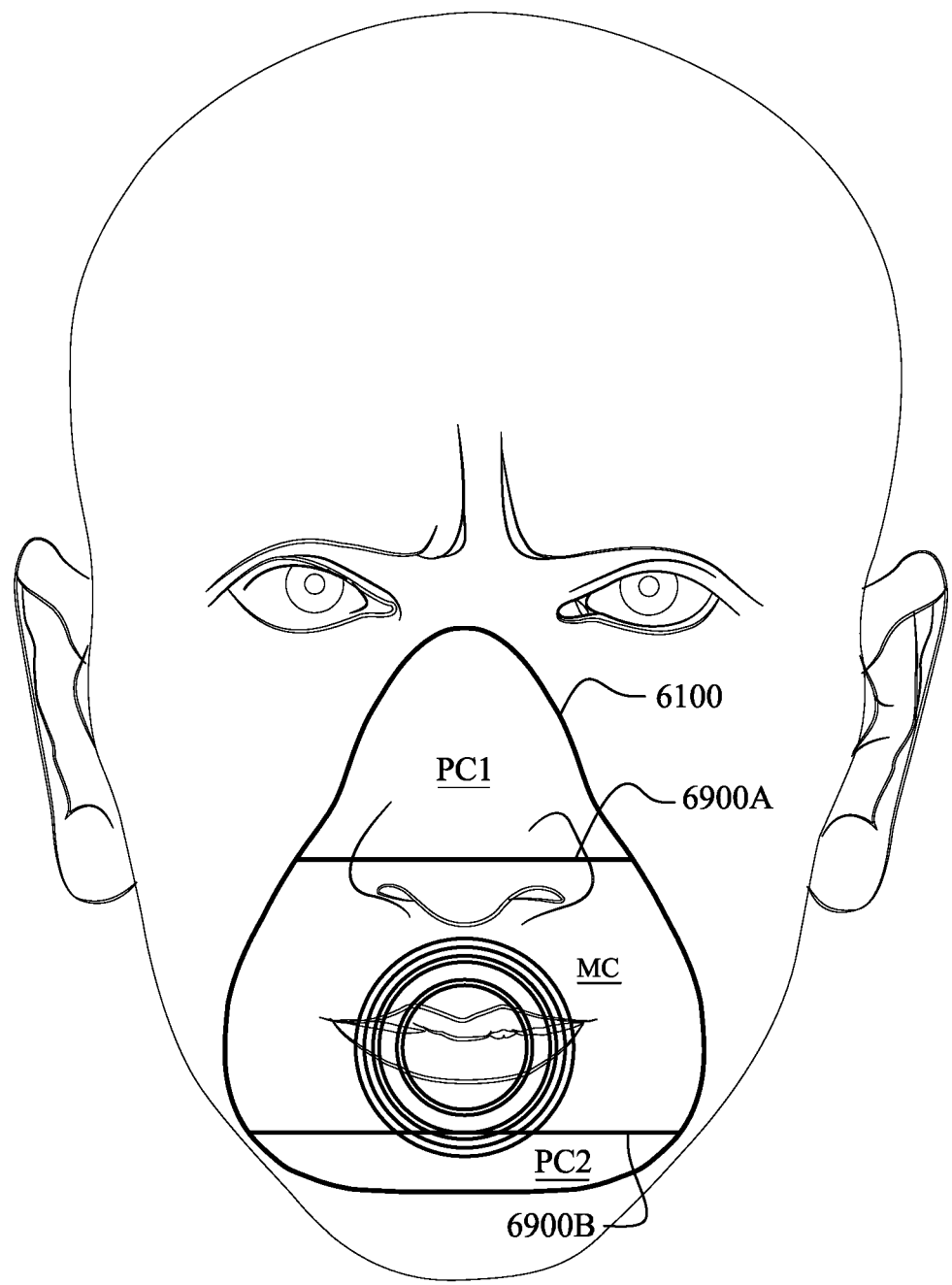

FIG. 13 is a schematic front view showing a cushion assembly including volume reducing members according to an example of the present technology.

Figure 14:
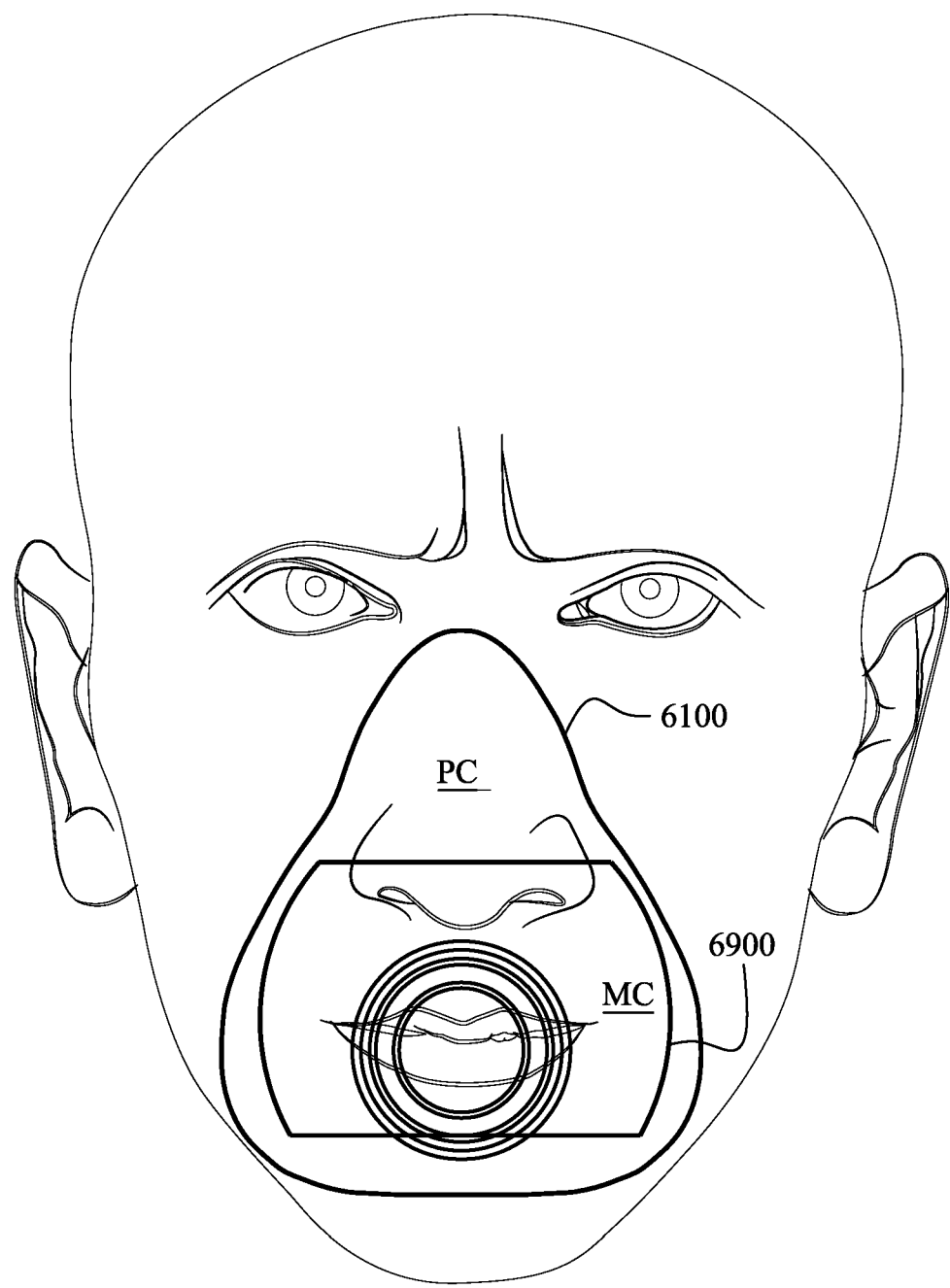

FIG. 14 is a schematic front view showing a cushion assembly including a volume reducing member according to an example of the present technology.

Figure 15:
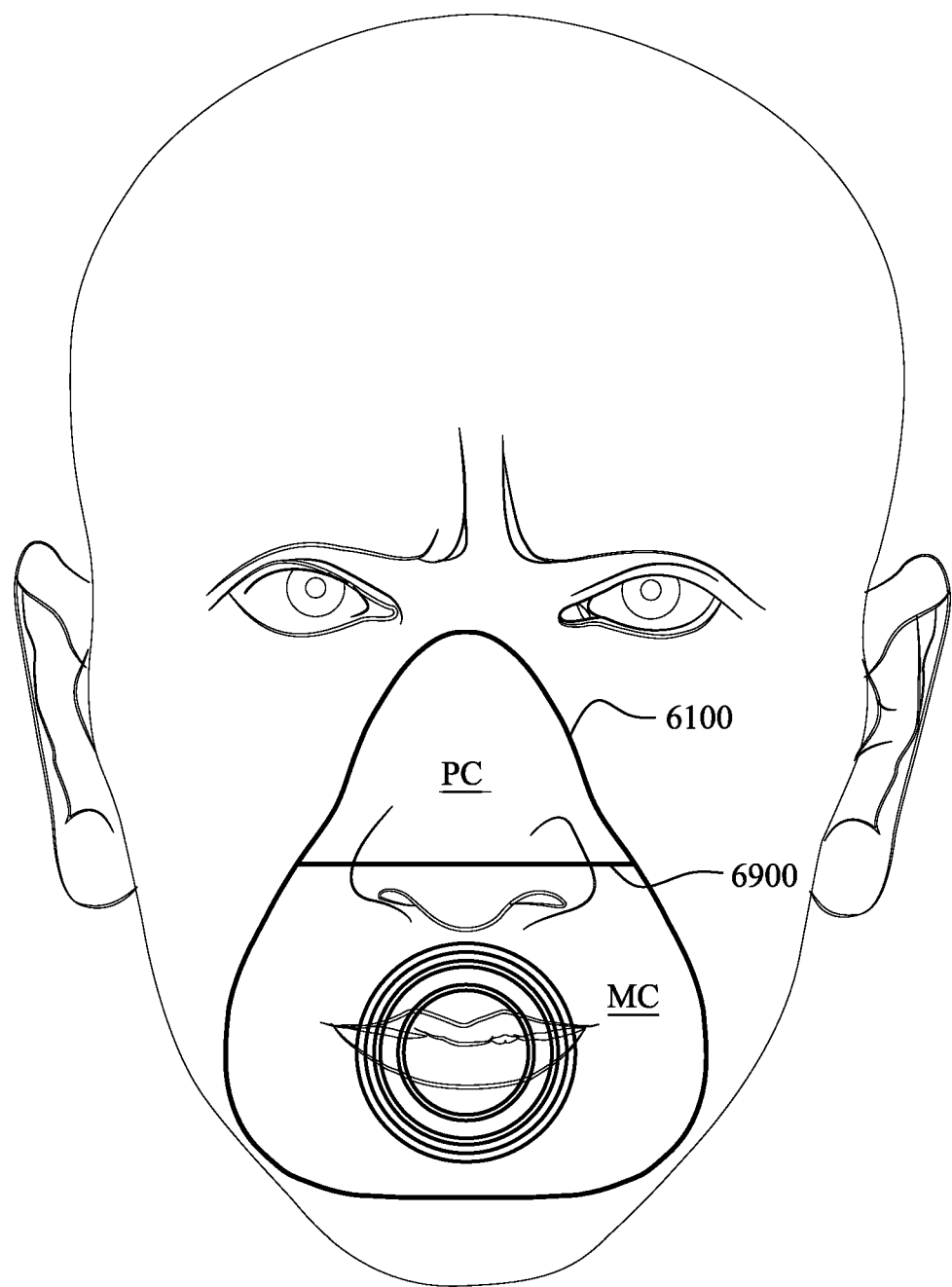

FIG. 15 is a schematic front view showing a cushion assembly including a volume reducing member according to an example of the present technology.

Figure 16:
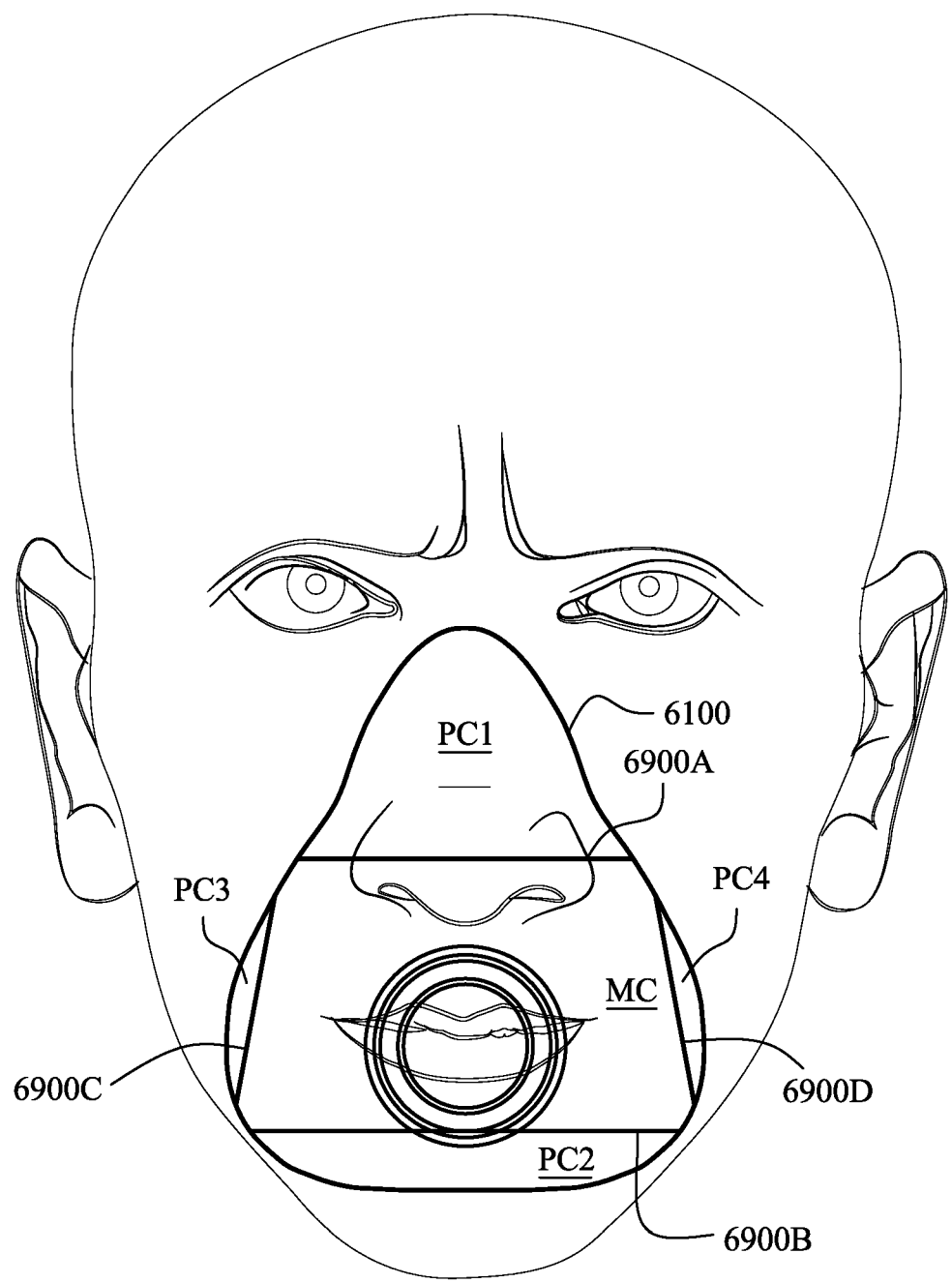

FIG. 16 is a schematic front view showing a cushion assembly including volume reducing members according to an example of the present technology.

Figure 17:
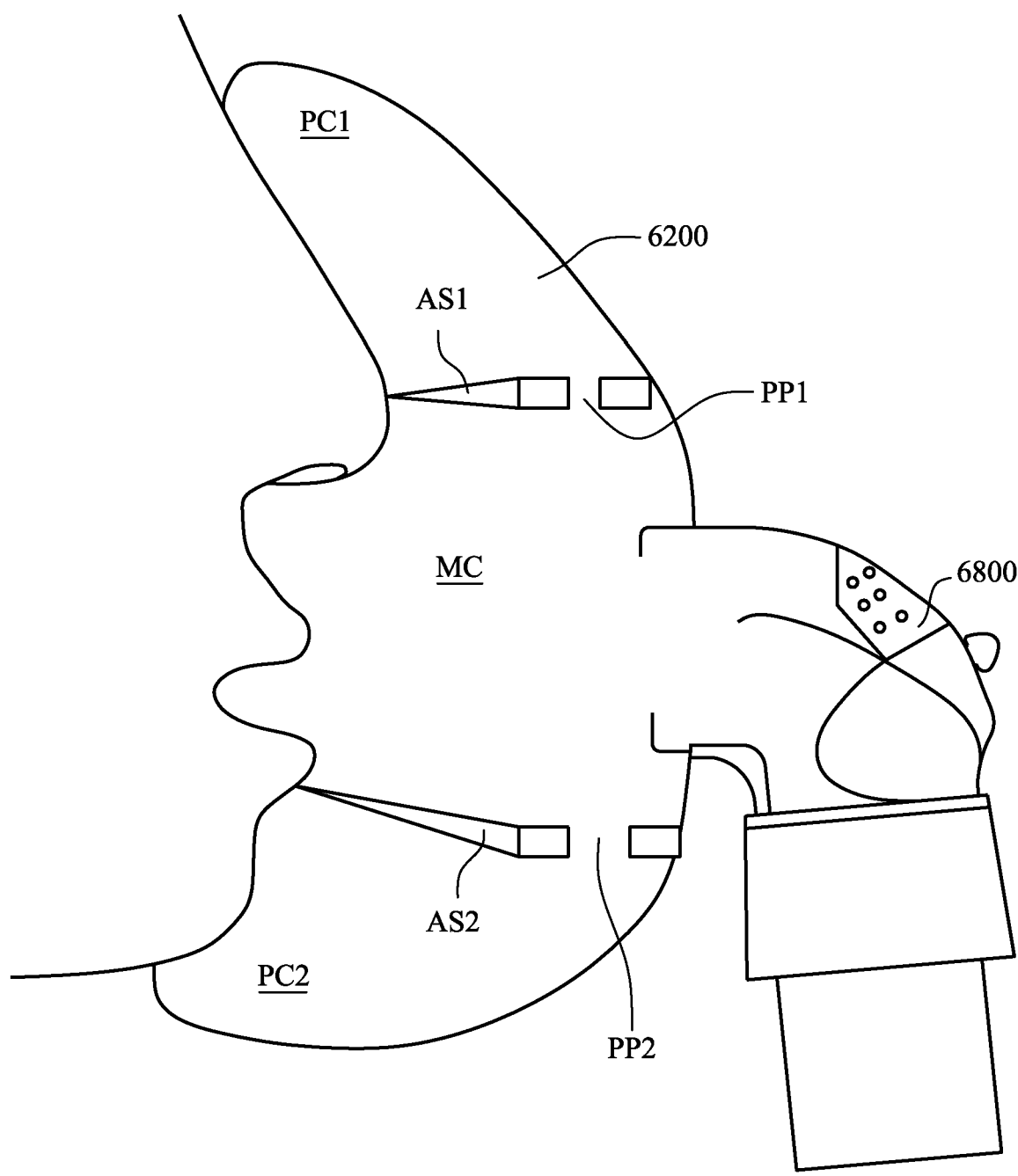

FIG. 17 is a schematic side view of a patient interface including additional seal members and pressurisation ports according to an example of the present technology.

Figure 18:
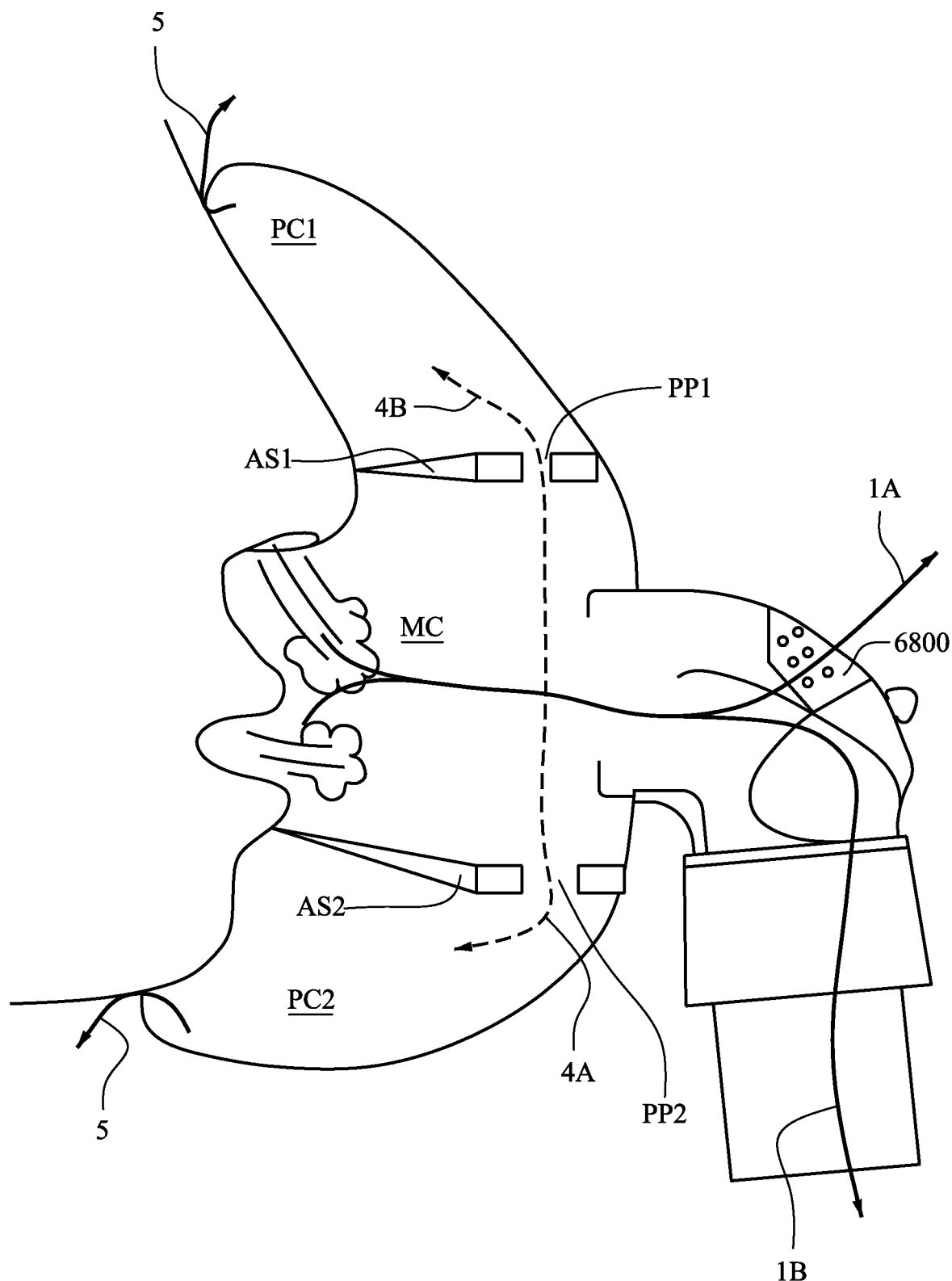

FIG. 18 is a schematic side view of the patient interface of FIG. 17 showing exemplary air flow paths during patient expiration according to an example of the present technology.

Figure 19:
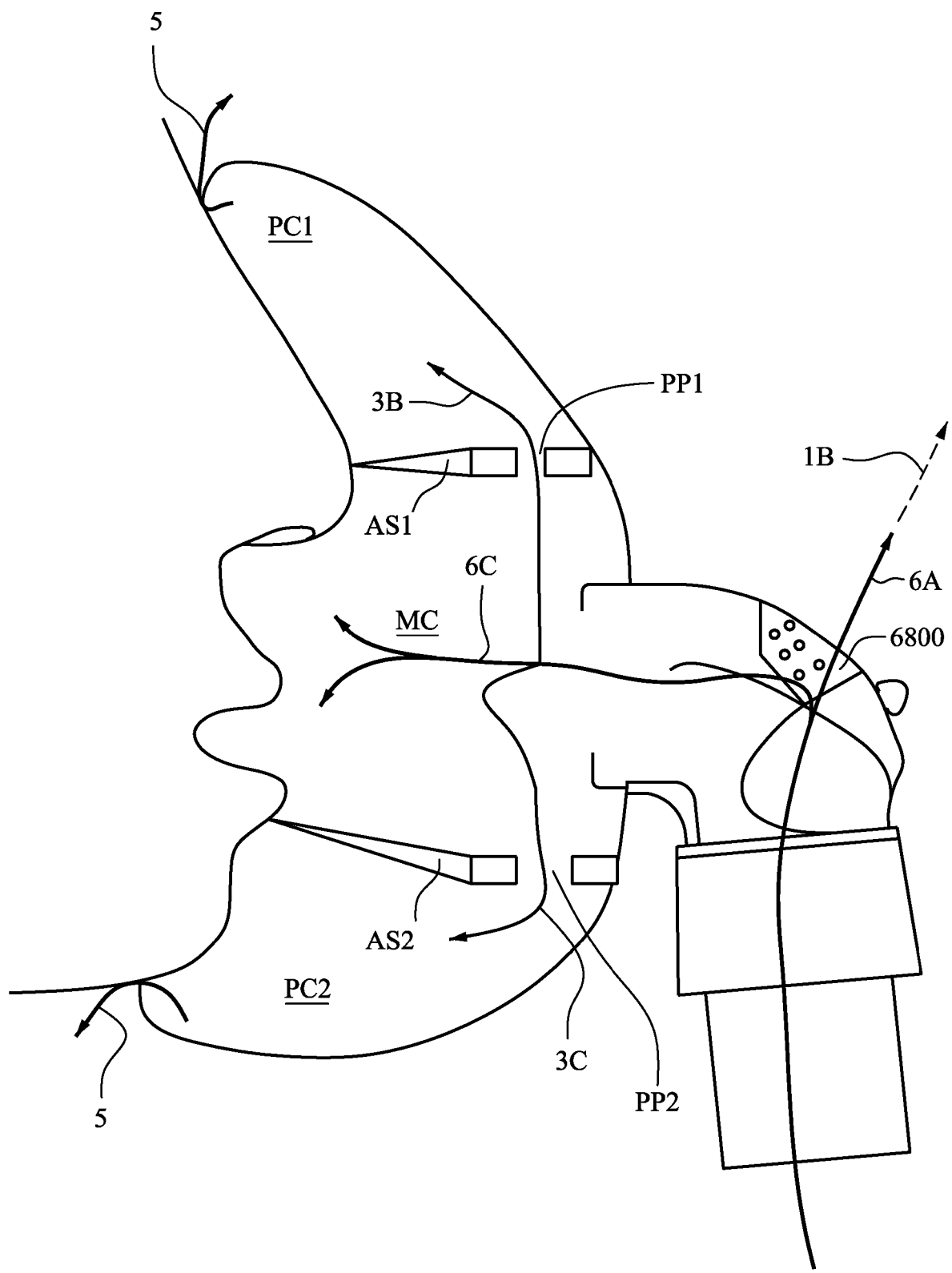

FIG. 19 is a schematic side view of the patient interface of FIG. 17 showing exemplary air flow paths during patient inspiration according to an example of the present technology.

Figure 20:
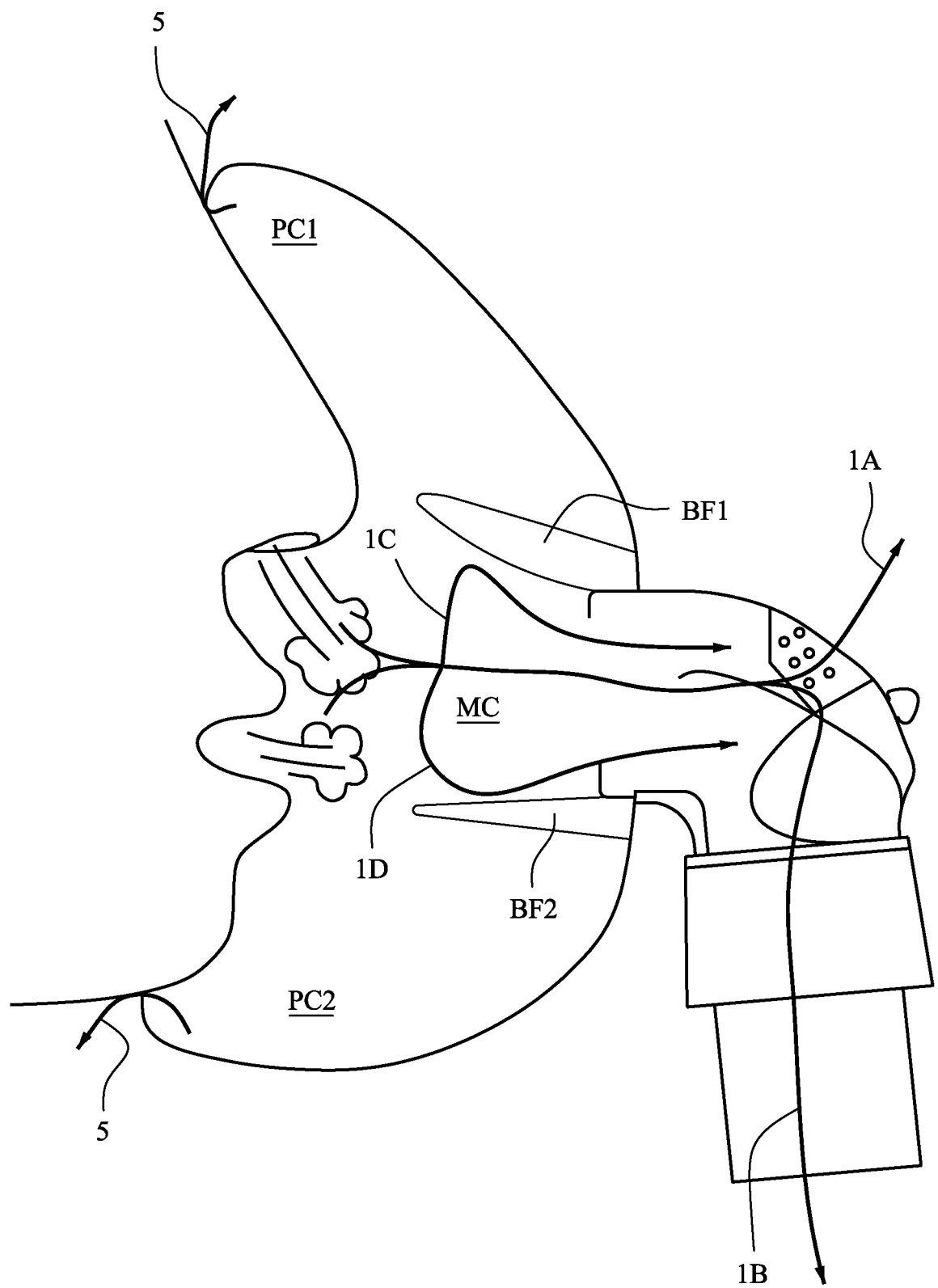

FIG. 20 is a schematic side view of a patient interface including baffle members and showing exemplary air flow paths during patient expiration according to an example of the present technology.

Figure 21:
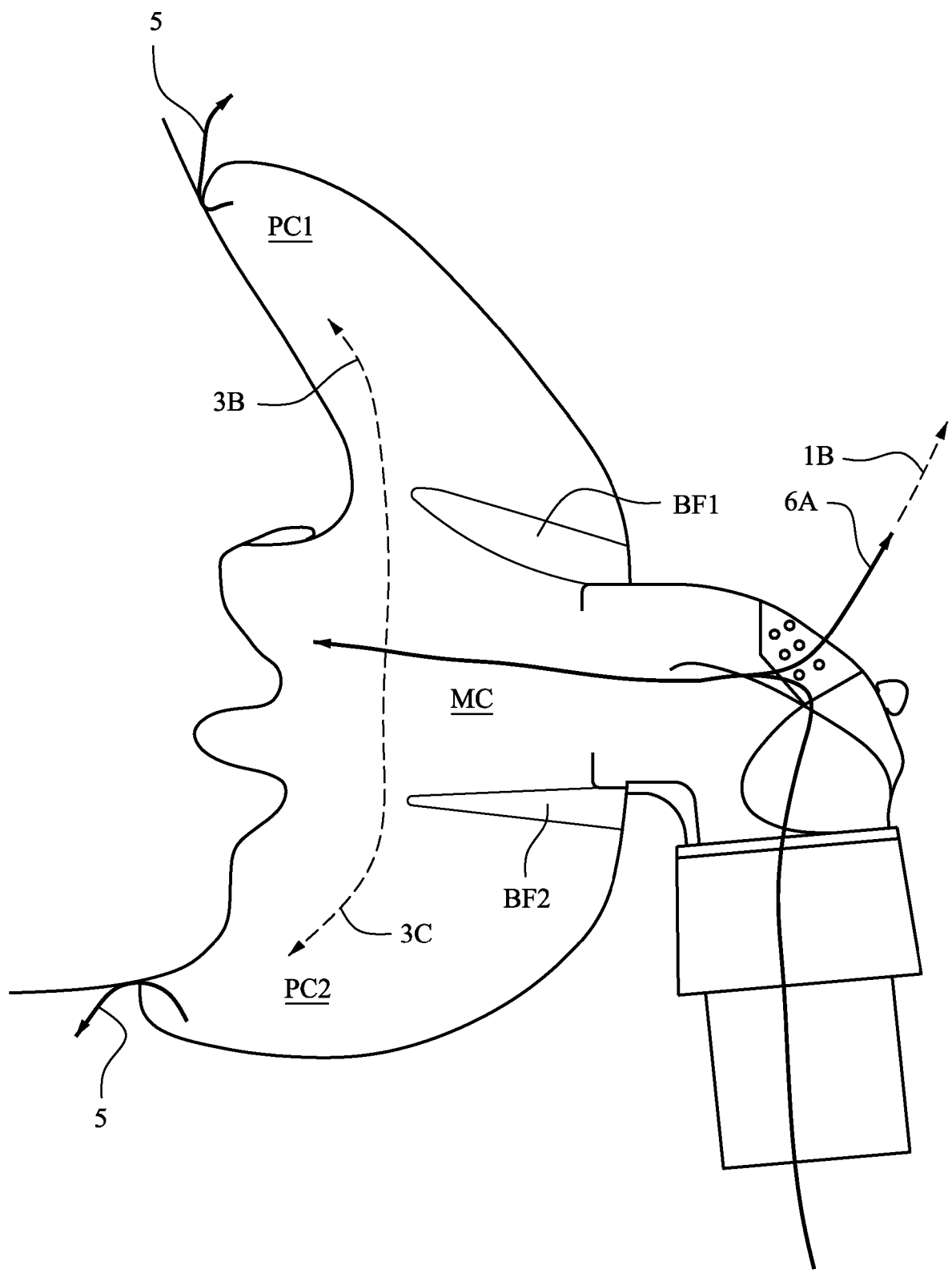

FIG. 21 is a schematic side view of the patient interface of FIG. 20 showing exemplary air flow paths during patient inspiration according to an example of the present technology.

Figure 22:
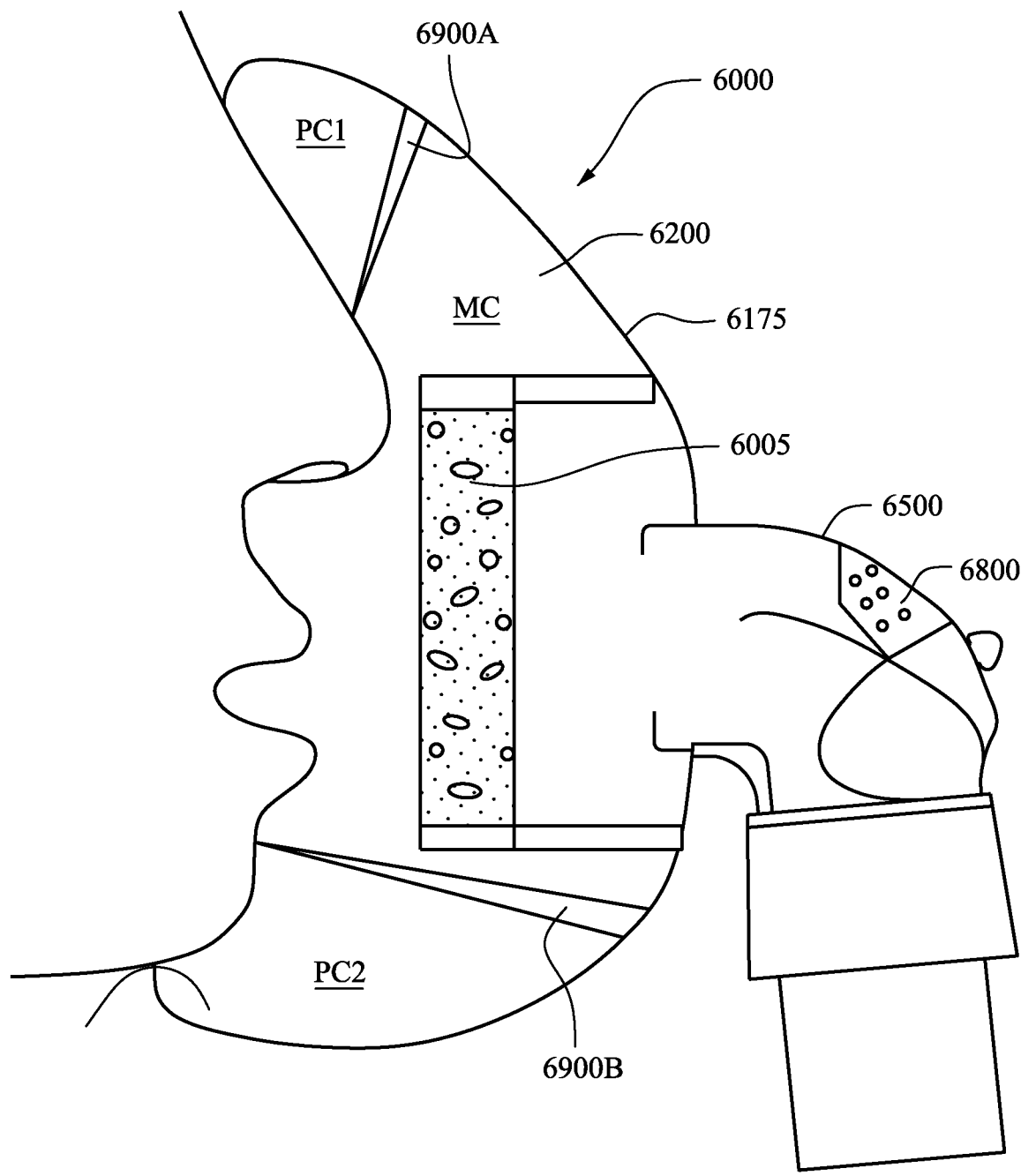

FIG. 22 is a side view showing a cushion assembly including a heat and moisture exchanger and volume reducing members according to an example of the present technology.

Figure 23:
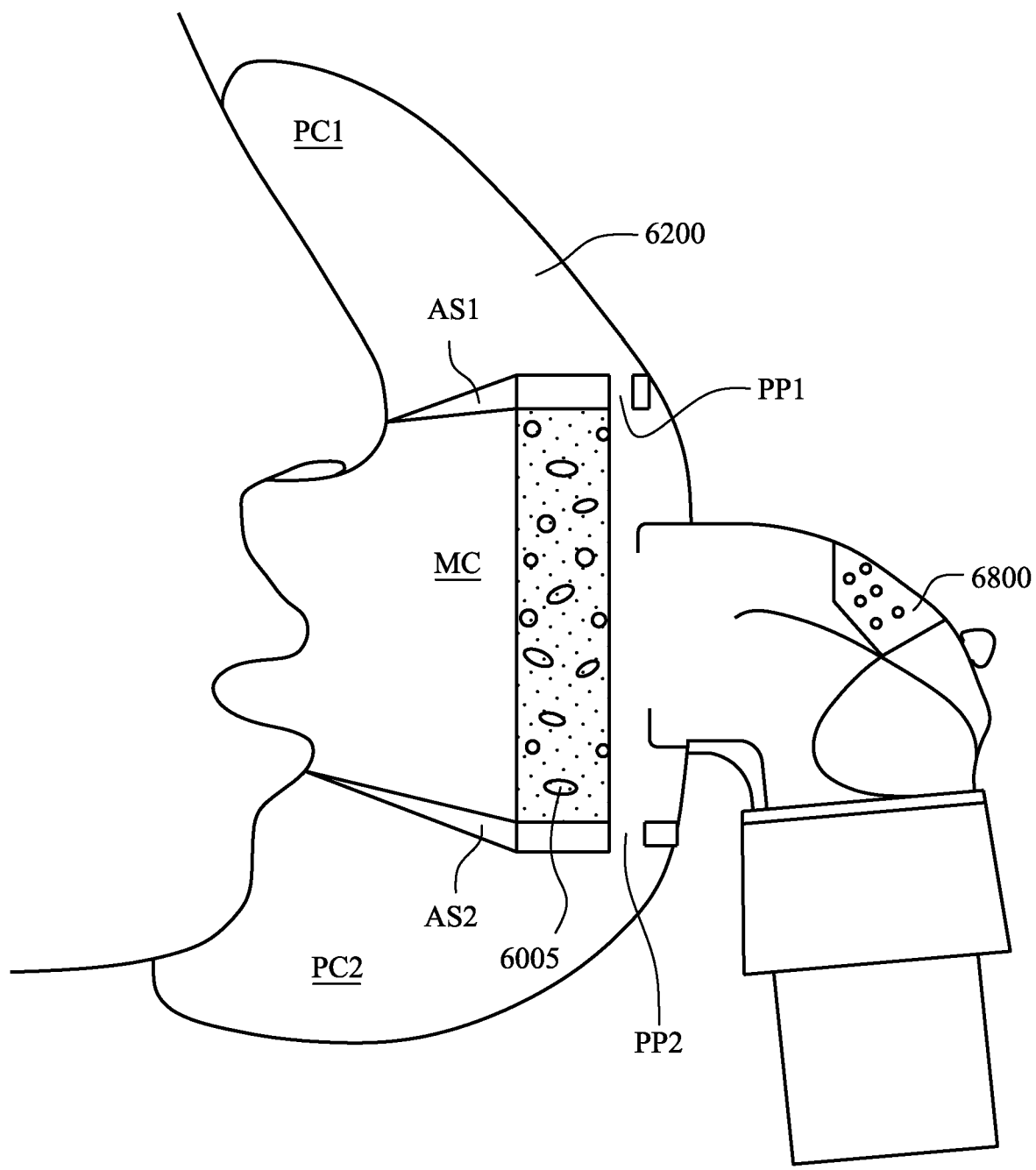

FIG. 23 is a schematic side view of a patient interface with a HME including additional seal members and pressurisation ports according to an example of the present technology.

Figure 24:
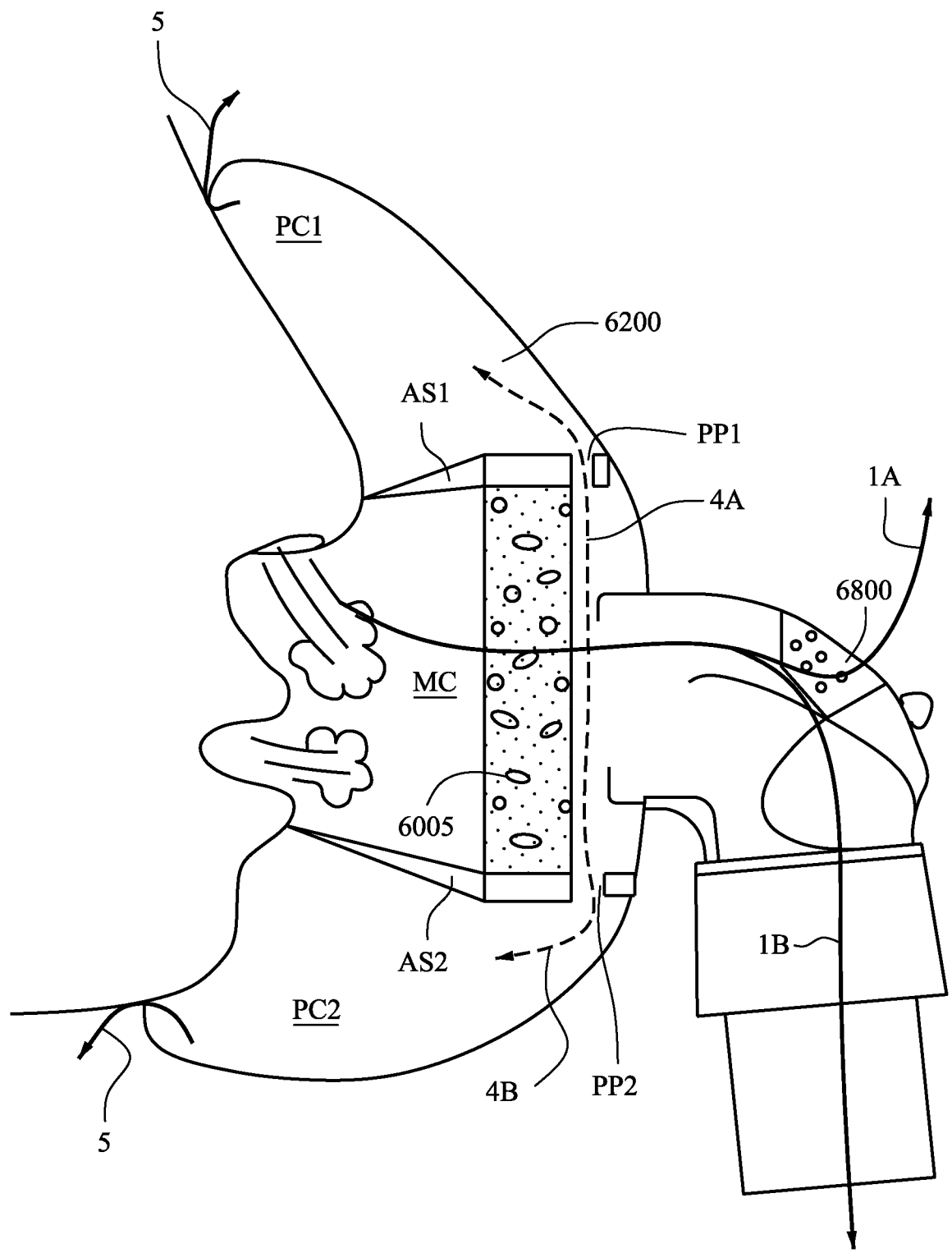

FIG. 24 is a schematic side view of the patient interface of FIG. 23 showing exemplary air flow paths during patient expiration according to an example of the present technology.

Figure 25:
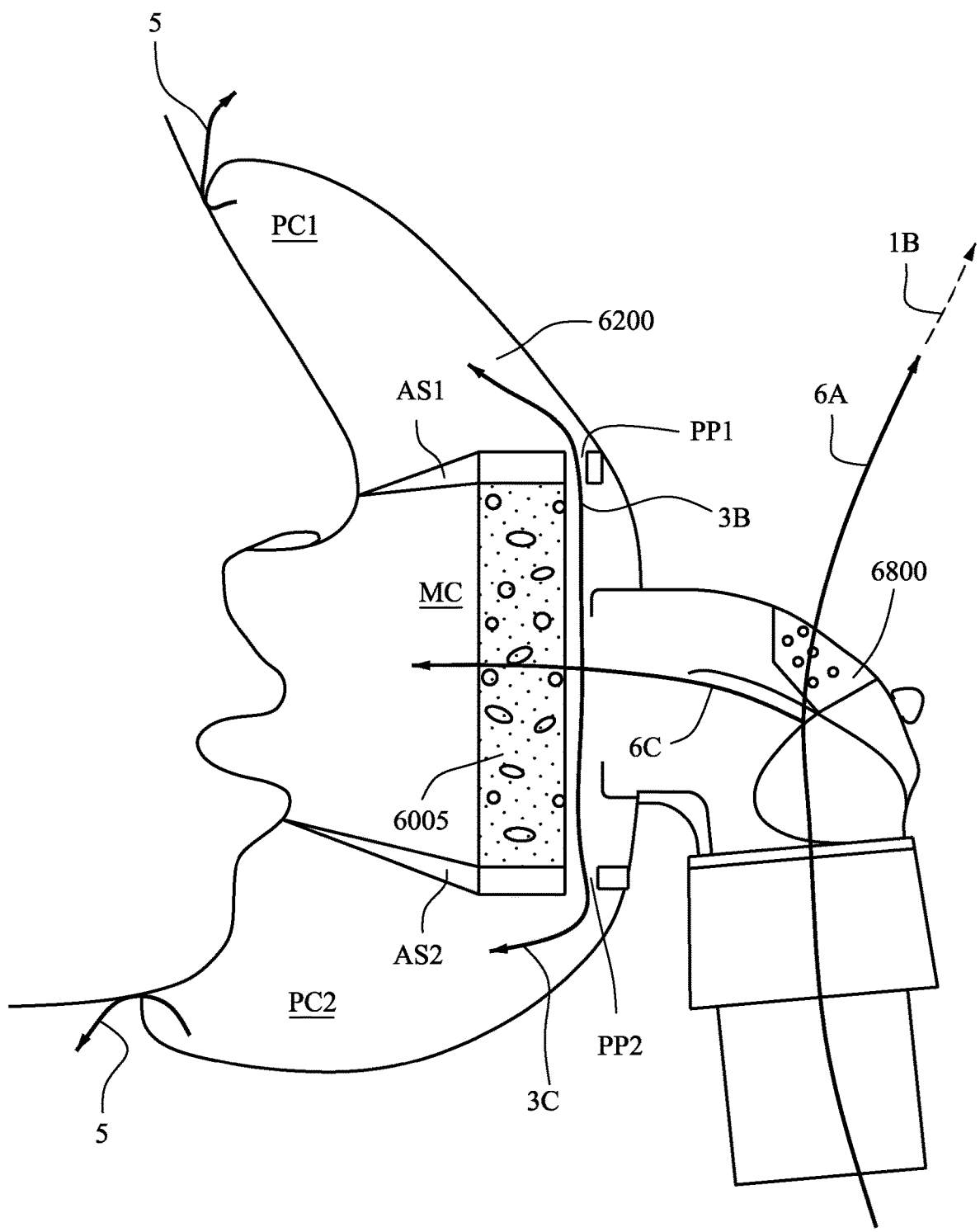

FIG. 25 is a schematic side view of the patient interface of FIG. 23 showing exemplary air flow paths during patient inspiration according to an example of the present technology.

Figure 26:
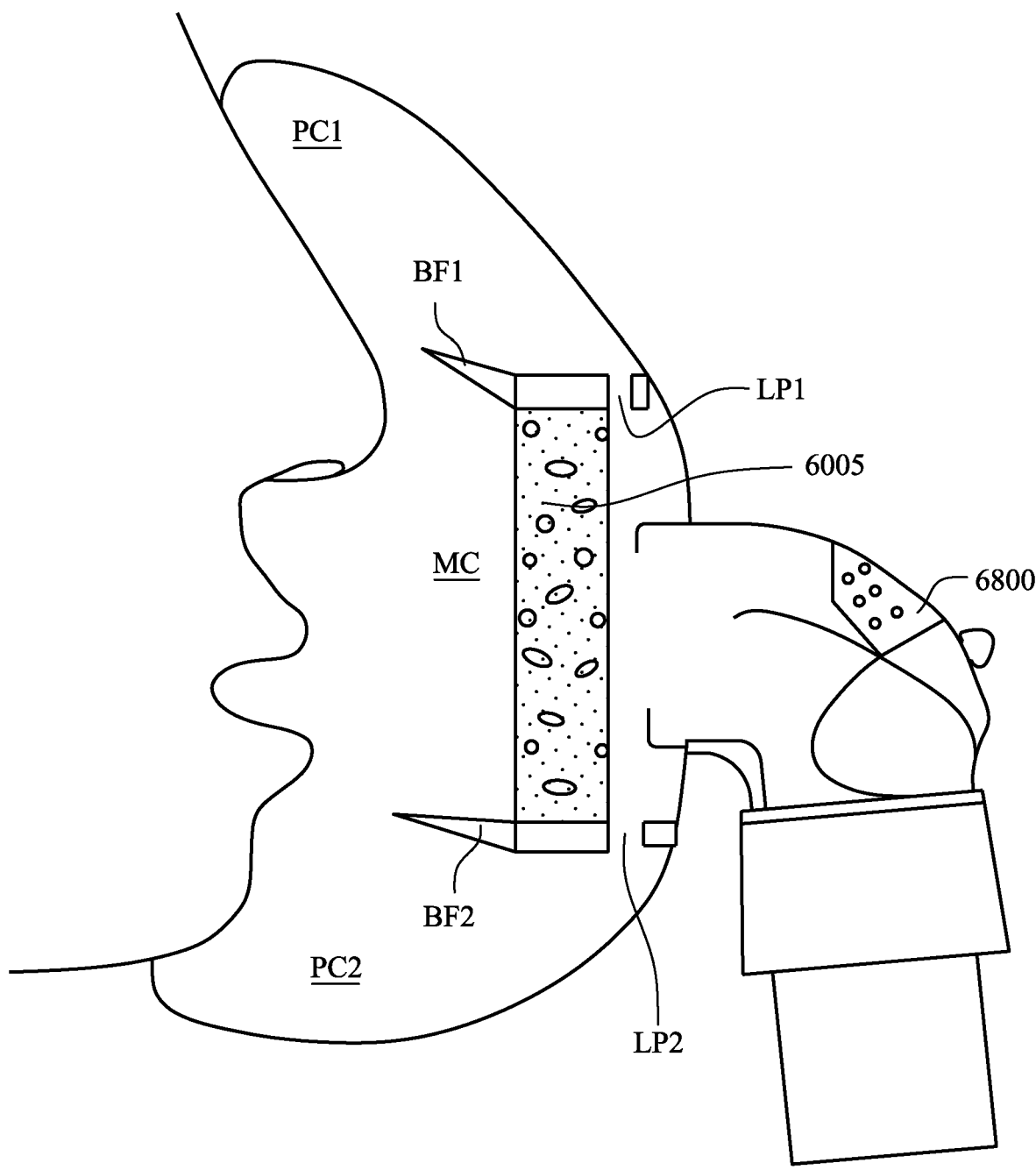

FIG. 26 is a schematic side view of a patient interface with a HME including baffle members and leak ports according to an example of the present technology.

Figure 27:
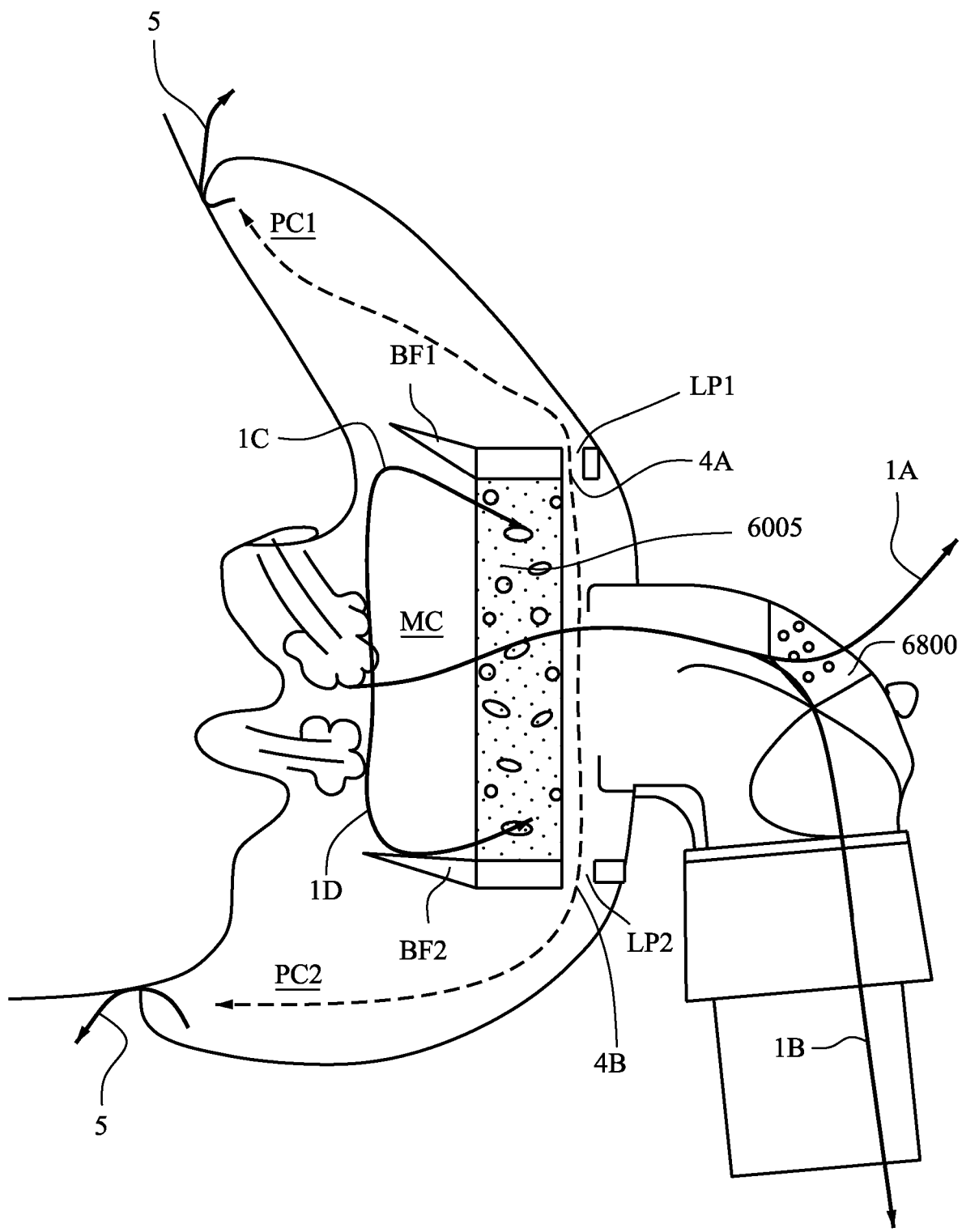

FIG. 27 is a schematic side view of the patient interface of FIG. 26 showing exemplary air flow paths during patient expiration according to an example of the present technology.

Figure 28:
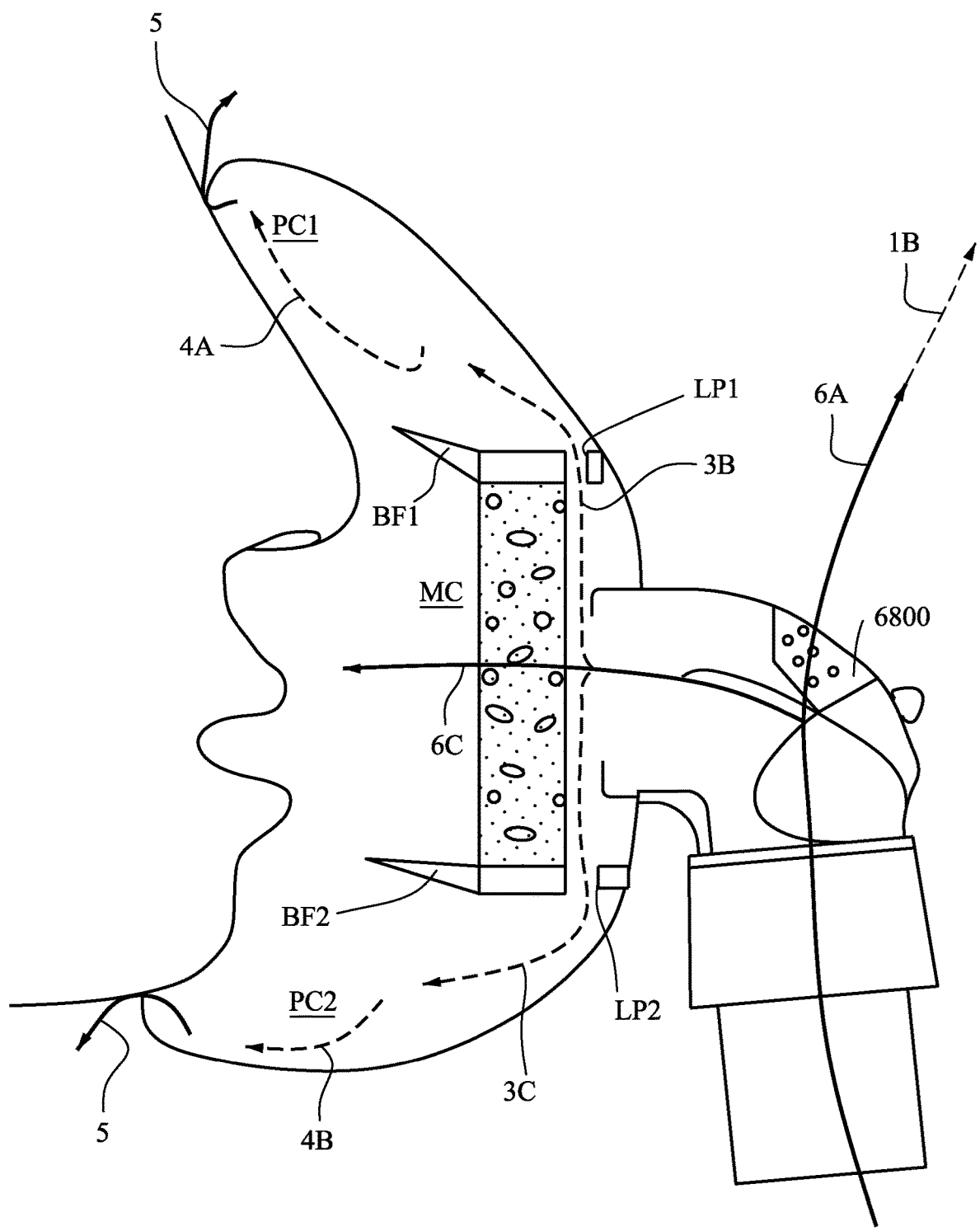

FIG. 28 is a schematic side view of the patient interface of FIG. 26 showing exemplary air flow paths during patient inspiration according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

Figure 1A:
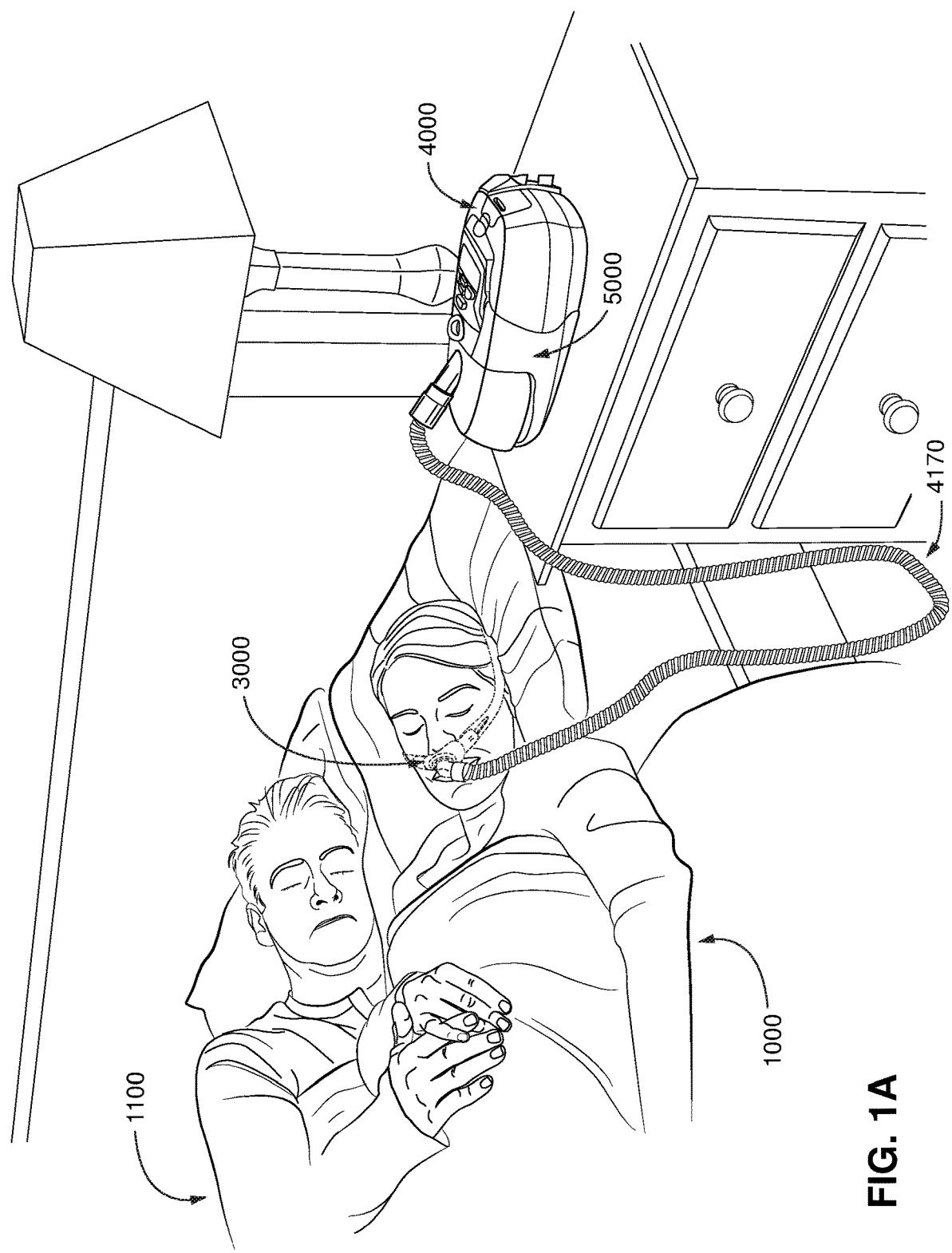
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 1B:
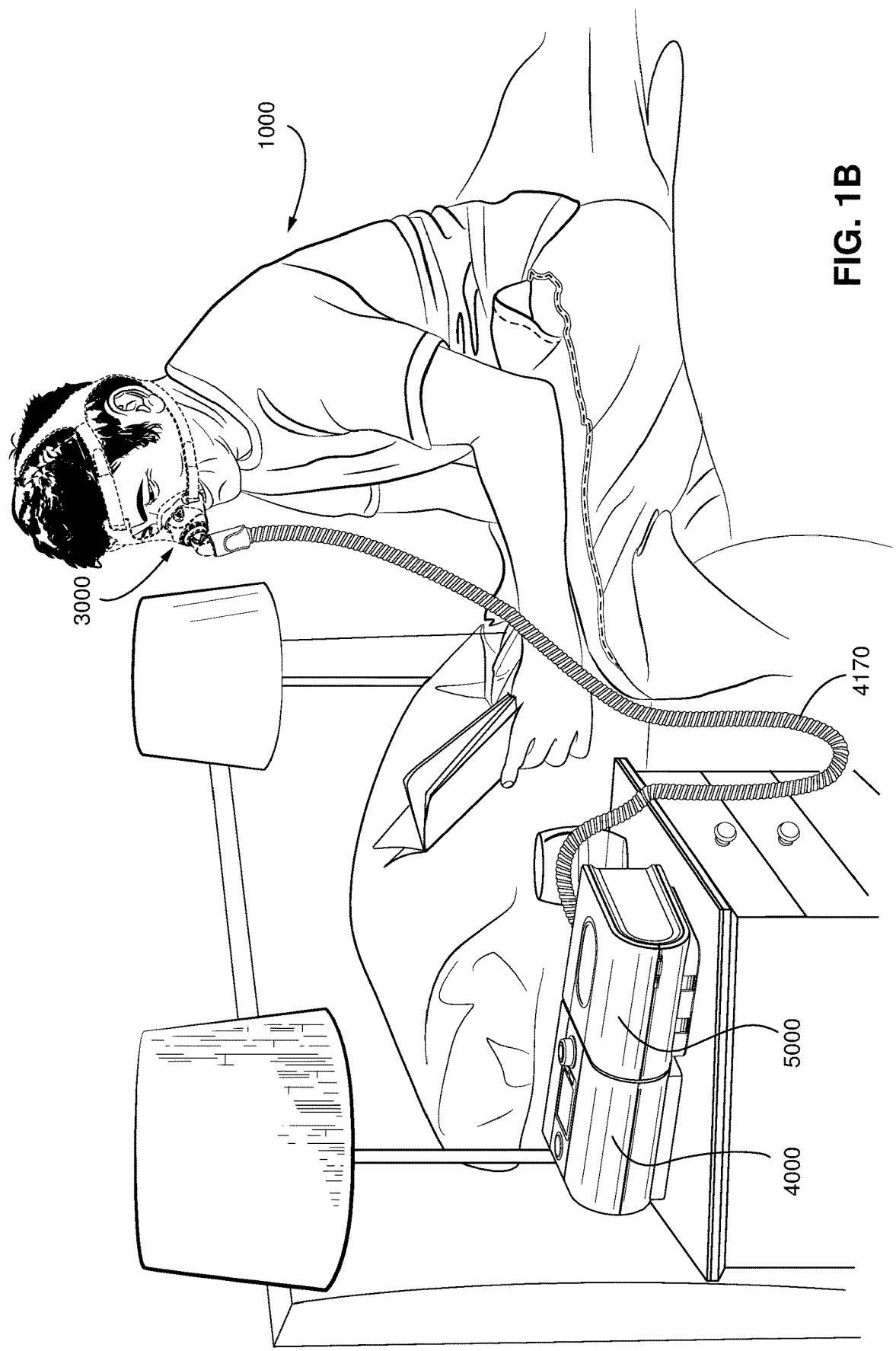
Figure 1C:

In one form, the present technology comprises an apparatus or device for treating a respiratory disorder. The apparatus or device may comprise an RPT device 4000 for supplying pressurised air to the patient 1000 via an air circuit 4170 to a patient interface 3000, e.g., see FIGS. 1A to 1C.

5.3 Patient Interface

As shown in FIG. 3A, a non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.3.1 Seal-Forming Structure

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange and a support flange. The sealing flange comprises a relatively thin member with a thickness of less than about 1 mm, for example about 0.25 mm to about 0.45 mm, that extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a springlike element and functions to support the sealing flange from buckling in use. In use the sealing flange can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

In certain forms of the present technology, a seal-forming structure 3100 is configured to correspond to a particular size of head and/or shape of face. For example one form of a seal-forming structure 3100 is suitable for a large sized head, but not a small sized head. In another example, a form of seal-forming structure 3100 is suitable for a small sized head, but not a large sized head.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200.

As described below, aspects of the present technology have particular application to patient interfaces with larger internal volumes, e.g., full-face masks, to reduce deadspace volume, e.g., to improve $CO_2$ rebreathing and/or increase the efficacy of a heat and moisture exchanger (HME). In illustrated examples, the full-face mask includes a seal forming structure adapted to surround the nose and mouth and form a seal along the nasal bridge region, sides of the nose regions, cheek regions, sides of the mouth regions, and below the lower lip, e.g., chin region. As shown in FIGS. 9, 11, and 12 for example, the seal along the chin region may be provided along a lower lip region (that is, the lip inferior) of the patient's face. In other examples as shown in FIGS. 4-8 and 17-28, the seal along the chin region may be provided along a lower side of the patient's chin. The position of the seal below the lower lip may be selected, e.g., to accommodate the HME and/or one or more volume reducing members.

Exemplary Air Flow Paths During Expiration and Inspiration

FIG. 4 shows a schematic side view of a full-face mask showing exemplary air flow paths during patient expiration. During expiration, a patient expires a volume of $CO_2$ enriched air into the plenum chamber of the mask. The volume of expired air may take a number of flow paths within the plenum chamber of the mask due to the flow dynamics of the mask and the patient. For example, a portion of the expired volume may be vent flow 1A, which is a volume of expired air that flows through the vent 3400 for $CO_2$ washout from the plenum chamber. A portion of the expired volume may be turbulent expiration flow 2A or 2B, which remains within the plenum chamber of the mask. In addition, a portion of the expired volume may be additional expired flow 1B that is a volume of expired air that flows past the vent 3400 and continues further downstream of the air delivery conduit towards the flow generator. The volume of air within the plenum chamber of the mask remains constant and therefore may be filled with a flow of $CO_2$ rich air from expiratory flow.

FIG. 5 shows a schematic side view of a full-face mask showing exemplary air flow paths during patient inspiration.

During inspiration, the flow generator generates an inspiratory flow of air at a positive pressure and delivers the flow via an air delivery conduit into the plenum chamber of the mask. The inspiratory flow delivers a volume of pressurised air that is substantially free of $CO_2$ via an inspiratory flow path 6B. A portion of the inspiratory flow path 6B is lost through inspiratory vent flow 6A and the remaining volume is delivered into the plenum chamber and towards the entrance of the patient's airways via inspiratory mask flow 6C. During inspiratory vent flow 6A, a portion of the volume remaining in the air delivery conduit from the additional expired flow 1B is also displaced through the vent 3400. However, some of the remaining volume of expired air from the additional expired flow 1B is also directed towards the entrance of the patient's airways by the inspiratory mask flow 6C. Moreover, the volume of turbulent expiration flow 2A and 2B may also be redelivered to the entrance of the airways via the inspiratory mask flow 6C. Thus, in this instance, the volume of expired air from the additional expired flow 1B and/or turbulent expiration flow 2A and 2B result in additional $CO_2$ rebreathing by the patient. Some of the $CO_2$ enriched expired air and the volume of inspiratory flow may be lost through leak flow 5 as a perfect seal may not always be achieved by the seal-forming structure (e.g., see FIGS. 4 and 5).

Exemplary Full-Face Mask with Heat and Moisture Exchanger (HME)

FIG. 6 shows a schematic side view of a full-face mask including a HME 15 positioned within the plenum chamber. The HME functions by capturing and retaining the heat and moisture from the volume of air of expired flow during patient exhalation. This heat and moisture is then redelivered to the patient during inspiration. The flow dynamics within the plenum chamber of a full-face mask comprising a HME may cause $CO_2$ rich expired air to remain within the plenum chamber, in use, thereby resulting in rebreathing of the $CO_2$ enriched air.

FIG. 7 shows a schematic side view of a full-face mask including a HME showing exemplary air flow paths during patient expiration. To capture the heat and moisture during exhalation, the expiratory flow must flow through the HME 15. However, the HME comprises a certain level of flow impedance, which impedes the vent flow 1A and additional expired flow 1B such that an increased volume of expired air may remain in the plenum chamber when compared to a full-face mask without the HME as shown in FIGS. 4 and 5. The impeded flow may result in an additional volume of expired air taking the path of turbulent expiration flow 2A and 2B. In addition, a portion of the impeded flow may result in a volume of expired air being lost from the plenum chamber through leak flow 5 via expiration leak flow paths 2C and 2D. The volume of expired air lost via the expiration leak flow paths 2C and 2D will result in a loss of heat and moisture from the expired flow as this volume of expired flow is loss through leak flow 5 prior to flowing through the HME.

FIG. 8 shows a schematic side view of a full-face mask including a HME showing exemplary air flow paths during patient inspiration. As noted above, a portion of the inspiratory flow path 6B is lost through inspiratory vent flow 6A and the remaining volume is delivered into the plenum chamber and towards the entrance of the patient's airways via inspiratory mask flow 6C. Also, the volume of turbulent expiration flow 2A and 2B may be redelivered to the entrance of the airways via the inspiratory mask flow 6C.

Plenum Chamber with One or More Volume Reducing Members

According to an example of the present technology, one or more volume reducing members (also referred to as volume dividing members or flow directing members) may be provided within the plenum chamber to reduce the effective internal volume of the plenum chamber. The one or more volume reducing members or flow directing members separates the plenum chamber into an effective internal volume and a deadspace volume and is structured and arranged to obstruct flow between the effective internal volume and the deadspace volume. Reducing the effective internal volume of the plenum chamber separates the unnecessary deadspace volume from volume required to deliver respiratory pressure therapy, thereby reducing the volume of air that is inhaled by the patient during therapy.

The reduction of volume of the plenum chamber reduces the volume of $CO_2$ that can be rebreathed by the patient, especially patient interfaces with relatively large internal volumes that tend to have additional unnecessary deadspace volumes to accommodate for portions of the patient's face (e.g., full-face masks). For example, FIG. 9 shows an exemplary full-face cushion assembly 6175 for a patient interface defining a plenum chamber 6200. The cushion assembly 6175 includes a multi-hole vent 6800 surrounding a connection port 6600. In such example, an excess deadspace volume DS1 is provided superior the entrance to the patient's nasal passages and an excess deadspace volume DS2 is provided inferior the entrance to the patient's mouth. It should be appreciated that deadspace volume is also provided around the sides of the patient's nose and/or mouth. In a theoretical example, a full-face mask would include two separate chambers sealing around respective nasal passages and a third chamber sealing around the mouth, with the remaining volume around each of the nasal passages the patient's mouth considered deadspace volume. Accordingly, an aspect of the present technology relates to a patient interface including a plenum chamber that provides minimal volume required to effectively deliver pressurized gas to the entrance of the patient's airways, without altering or impacting the seal around the patient's airways.

Generally, $CO_2$ rebreathing increases as the internal volume of the plenum chamber increases. For example, the volume of $CO_2$ that is rebreathed by a patient using a full-face mask is larger when compared to the volume of $CO_2$ that is rebreathed by a patient using a nasal mask which has a smaller plenum chamber. $CO_2$ rebreathing may be further exacerbated by reducing the effective washout of exhaled $CO_2$ out of the internal volume via the vent, e.g., by providing an optional heat and moisture exchanger (HME) within the plenum chamber positioned between the patient's airways and the vent which impedes the direct flow of exhaled $CO_2$ towards the vent. That is, the HME within the plenum chamber results in flow impedance of vent flow which reduces the effectiveness of $CO_2$ washout, thereby increasing the build-up of $CO_2$ within the plenum chamber, and thus resulting in an increase of $CO_2$ rebreathing.

It is not always possible to simply increase the size of the vent to improve $CO_2$ washout as there is a particular vent flow acceptable to allow for respiratory pressure therapy. Also, it is not always possible to simply reduce the volume of the plenum chamber as a minimum volume is required to allow the patient interface to seal around the desired areas of the patient's face. For example, an exemplary full-face mask is adapted to seal along the nasal bridge, sides of the nose, cheeks, sides of the mouth and below the lower lip on the chin to provide an optimal seal.

Another aspect that may impact $CO_2$ washout is the location of the vent. For example, $CO_2$ washout performance may be improved by locating the vent in an optimal position to allow exhaled flow to directly washout through the vent and to the atmosphere. However, there are also limitations to vent locations. For example, the vent may need to be located to direct flow away from the patient and the patient's bed partner. In the example of a patient interface that utilises a HME, the vent may be required to be positioned on an opposing side of the HME relative to the patient, to ensure maximum performance of the HME by minimising moisture loss during venting and prior to patient delivery.

Accordingly, a patient interface according to an example of the present technology is structured to provide sealing around the patient's nose and/or mouth for respiratory pressure therapy while reducing the internal volume of the plenum chamber to reduce $CO_2$ rebreathing.

An example of the present technology will be described in relation to the interface-type shown in FIG. 10, which shows a full-face patient interface 6000 (e.g., full-face mask) comprising a frame member 6050, a cushion assembly (e.g., full-face cushion assembly 6175), a positioning and stabilising structure 6300, and an elbow or swivel elbow 6500 which is connected to the gas delivery tube 4180 for fluid communication with the plenum chamber 6200 of the patient interface. Further details and examples of such interface-type are disclosed in PCT Publication No. WO 2015/006826, which is incorporated herein by reference in its entirety.

The frame member 6050 (e.g., constructed of a relatively hard plastic material such as polycarbonate) provides a connection between the cushion assembly 6175 and the positioning and stabilising structure 6300, e.g., either in a removable fashion or a more permanent fashion, to allow sealing forces to be transferred to the cushion assembly 6175 from the positioning and stabilising structure 6300. The frame member 6050 may also be commonly referred to as a shroud, headgear connection structure, or chassis. As arms for the positioning and stabilising structure 6300 are provided to the frame member 6050, connection structures are not needed or provided to the cushion assembly 6175.

In the illustrated example, the cushion assembly 6175 provides an integral unit including a front wall portion 6150 (e.g., anterior wall portion) that is connected or otherwise provided to the seal-forming structure 6100 to form the plenum chamber 6200. For example, the front wall portion 6150 may be permanently (e.g., molded in one piece, co-molded) or removably (e.g., mechanical interlock) connected to the seal-forming structure 6100. In an example, the seal-forming structure 6100 is constructed of a relatively flexible or pliable material (e.g., elastic material such as silicone) and the front wall portion 6150 is constructed of a relatively rigid material (e.g., polycarbonate, nylon).

The front wall portion 6150 comprises a multi-hole vent 6800 surrounding the connection port 6600, which is connected to the elbow or swivel elbow 6500.

To reduce the volume of $CO_2$ that is rebreathed by the patient, one or more volume reducing members according to an example of the present technology are provided within the plenum chamber 6200 to reduce the unnecessary deadspace volume within the plenum chamber 6200. The one or more volume reducing members are structured to separate, divide, or partition the plenum chamber 6200 into at least two separate and distinct chambers, e.g., a main chamber and at least one peripheral chamber.

In the illustrated example shown in FIG. 11, the volume reducing members are in the form of movable flaps or baffles 6900A, 6900B provided within the plenum chamber 6200 to separate, divide, or partition the plenum chamber 6200 into a main chamber MC and first and second peripheral chambers PC1, PC2.

The main chamber MC established by the movable flaps 6900A, 6900B is in direct fluid communication with the connection port 6600, the patient's airways, and the vent 6800 for $CO_2$ washout. The main chamber MC is necessary to deliver a flow of breathable gas to the entrance of a patient's airways during respiratory pressure therapy.

The first and second peripheral chambers PC1, PC2 established by the movable flaps 6900A, 6900B comprise unnecessary deadspace volumes within the plenum chamber 6200. The first and second peripheral chambers PC1, PC2 are separate and distinct from the main chamber MC (e.g., first and second peripheral chambers are partitioned from the main chamber) such that the overall effective internal volume of the plenum chamber 6200 is reduced to the volume of the main chamber MC. Accordingly, $CO_2$ rebreathing is reduced as the effective volume provided by the main chamber MC reduces the volume of $CO_2$ that is rebreathed.

In the illustrated example, each movable flap 6900A, 6900B includes a first end providing a connecting portion 6905 that is provided or otherwise connected to an interior surface of the front wall portion 6150 of the cushion assembly 6175. Each movable flap 6900A, 6900B also includes a second, free end providing an end portion 6910 configured or structured to be oriented towards the patient's face.

In an example, each movable flap 6900A, 6900B is formed separately from the cushion assembly 6175 (e.g., insertable or retrofittable movable flap) and attached thereto, e.g., adhesive, mechanical interlock. Alternatively, each movable flap 6900A, 6900B may be integral or formed in one piece with the cushion assembly 6175, e.g., one piece mold, co-mold. It should be appreciated that the connecting portion may be provided or otherwise attached to the front wall portion and/or to the seal-forming structure of the cushion assembly.

In an example, the end portion 6910 of each movable flap 6900A, 6900B is configured or structured to be oriented towards the patient's face so that the end portion 6910 forms a gap or space between the end portion 6910 and the patient's face, which provides a baffle or partition to separate the main chamber MC from the first and second peripheral chambers PC1, PC2. The moveable flaps 6900A, 6900B create a flow bias such that all patient inhalation and patient exhalation during respiratory pressure therapy occurs via the main chamber MC. This arrangement provides the vent with a smaller volume of $CO_2$ for washout, thereby reducing the volume of $CO_2$ rebreathed. The peripheral chambers PC1, PC2 are pressurised and provide pneumatic sealing of the seal forming structure 6100 to the patient's face, but remain stagnant. This means that air does not necessarily flow into or out of the peripheral chambers PC1, PC2 during the patient's breathing cycle, and therefore $CO_2$ is not built up in the peripheral chambers PC1, PC2 and then rebreathed during inspiration.

In an example, one or both of the movable flaps 6900A, 6900B may be oriented towards the patient's face so that the end portion 6910 lightly engages the patient's face, but does not completely seal and isolate the main chamber MC from the first and second peripheral chambers PC1, PC2. In an alternative example, one or both of the movable flaps 6900A, 6900B may be configured or structured to engage the patient's face to form a complete airtight seal with the patient's face.

In an example, each movable flap 6900A, 6900B may be relatively flexible (e.g., constructed of elastomeric material such as silicone) to allow the movable flap to deform and/or flex in use. In the illustrated example, each movable flap 6900A, 6900B includes a tapered shape along its length, e.g., thicker connecting portion 6905 that tapers to a thinner end portion 6910. However, it should be appreciated that the movable flap may have other suitable structures to provide a barrier or partition between the main chamber MC and respective peripheral chambers PC1, PC2. In addition, the movable flap may include structure to enhance its flexibility and/or sealing properties, e.g., bellows or gusset along its length, contoured end portion.

For example, the movable flap may be in the form of a thin flexible membrane flap structured to reduce contact pressure, thereby reducing any potential discomfort caused by the movable flap contacting the patient's face. The flexibility may also allow the flexible membrane flap to better conform to the profile of the patient's face. The flap thickness may be tuned, e.g., to provide sufficient rigidity to prevent blow out, maintain sufficient separation between the divided chambers, and/or provide sufficient flexibility to conform to a patient's face.

In the illustrated example, the movable flap 6900A is an upper or superior movable flap arranged to establish the first peripheral chamber PC1 and the movable flap 6900B is a lower or inferior movable flap arranged to establish the second peripheral chamber PC2.

As illustrated in FIG. 11, the upper movable flap 6900A is configured or structured to be oriented towards the patient's face generally along the pronasale region of the patient's nose and along respective sides of the nose to partition the first peripheral chamber PC1 from the main chamber MC. However, it should be appreciated that the upper movable flap 6900A may be configured or structured to be oriented towards other regions of the patient's nose. For example, FIG. 12 shows an example of an upper movable flap 6900A configured or structured to be oriented above the pronasale region, i.e., along the ridge of the patient's nose and along respective sides of the patient's nose. In general, the upper movable flap 6900A should be configured or structured to be oriented towards the patient's face so as to not obstruct or prevent communication of the main chamber MC with the patient's nasal passages.

As illustrated in FIG. 11, the lower movable flap 6900B is configured or structured to be oriented towards the patient's face generally along a region below the patient's lower lip, e.g., along the patient's chin region. In general, the lower movable flap 6900B should be configured or structured to be oriented towards the patient's face so as to not obstruct or prevent communication of the main chamber MC with the patient's mouth.

As illustrated, the upper and lower movable flaps 6900A, 6900B each include a suitable length (e.g., length measured along a path from the connecting portion to the end portion) and orientation (e.g., connection point and orientation angle with respect to the front wall portion 6150) configured or structured to be oriented towards their respective region of the patient's face. It should be appreciated that the upper and lower movable flaps 6900A, 6900B may include other suitable lengths, shapes, connection points with the front wall portion, and/or orientation angles with respect to the front wall portion in order to adjust the desired orientation with the patient's face and/or adjust the chamber volume size and/or adjust the boundary between chambers. Also, the length and/or orientation may vary along the width of flap to conform to the profile of the patient's face.

In the illustrated example, the upper and lower movable flaps 6900A, 6900B define first and second peripheral chambers PC1, PC2 that are separated from the main chamber MC as well as separated from one another, e.g., see FIG. 13.

In an alternative example, as shown in FIG. 14, a single peripheral movable flap 6900 may be provided to establish the main chamber MC and a peripheral chamber PC separated from the main chamber MC. In this example, the movable flap 6900 is adapted to form a peripheral partition and establish a single peripheral chamber PC including upper and lower portions communicated via side portions.

It should be appreciated that one or more movable flaps may be arranged within the plenum chamber in other suitable manners to establish one or more peripheral chambers separated from the main chamber. For example, FIG. 15 shows a movable flap 6900 defining a main chamber MC and a single upper peripheral chamber PC. FIG. 16 shows movable flaps 6900A, 6900B, 6900C, and 6900D defining a main chamber MC and peripheral upper, lower, and side chambers PC1, PC2, PC3, and PC4.

The provision of one or more volume reducing members (e.g., one or more movable flaps 6900) within the plenum chamber 6200 is advantageous as it allows the internal volume of the plenum chamber 6200 to be reduced without altering or changing the seal forming structure 6100. This arrangement avoids any impact on the seal performance while reducing the effective internal volume of the plenum chamber 6200 to reduce $CO_2$ rebreathing. For example, in the case of a full-face mask, the seal forming structure 6100 is adapted to surround the nose and mouth and form a seal along the nasal bridge region, sides of the nose regions, cheek regions, sides of the mouth regions, and below the lower lip on the chin region of the patient's face. In this typical configuration, unnecessary excess or deadspace volume (e.g., see deadspace volumes DS1 and DS2 in FIG. 9) of the plenum chamber 6200 is positioned above the entrance of the nares and below the patient's mouth and is typically unnecessary for delivering a flow of breathable gas to the entrance of the patient's airways. This excess or deadspace volume increases the volume of $CO_2$ gas within the interior of the plenum chamber 6200, which increases the volume of $CO_2$ that is rebreathed. However, this excess or deadspace volume may be necessary to accommodate portions of the patient's face and allow for the seal forming structure to form a seal, e.g., above the entrance of the nares along the nasal bridge and the sides of the nose regions of the patient's face. Sealing on the bony parts of the nose generally allows for sufficient force to be applied to maintain seal without occlusion of the nasal passages. Thus, full-face masks are typically restricted to this configuration of sealing to maintain seal stability and prevent nasal occlusion. Accordingly, the provision of one or more volume reducing members provides a viable solution to reduce the volume of $CO_2$ that is rebreathed that is common in full-face masks.

FIG. 17 shows a patient interface according to another example of the present technology, and FIGS. 18 and 19 show exemplary air flow paths for such patient interface during patient expiration and inspiration respectively. As illustrated, the patient interface includes additional seal members AS1 and AS2 and pressurisation ports PP1 and PP2.

The seal members AS1 and AS2 separate the plenum chamber 6200 into a main chamber MC and first and second peripheral chambers PC1, PC2 so as to reduce the functional deadspace volume of the patient interface. In this example, pressurisation ports PP1 and PP2 allow the pressurisation of peripheral chambers or volumes PC1 and PC2 by flow paths 3B and 3C respectively (see FIG. 19). Pressurisation of these peripheral volumes PC1 and PC2 may be necessary to provide an effective seal on the patient's face. In alternative examples, the plenum chamber may include a single peripheral volume or three or more peripheral volumes each with at least one pressurisation port.

During expiration (see FIG. 18), portions of expiratory flow may flow directly out the gas washout vent 6800 (e.g., flow path 1A). In addition, some of the flow may flow down the air delivery conduit (e.g. flow path 1B). Moreover, if a leak path were to occur via seal leak 5, a pressure differential may drive some of the flow into peripheral volumes PC1 and PC2 via the pressurisation ports PP1 and PP2 (e.g., flow paths 4A and 4B).

During inspiration (FIG. 19), at least a portion of flow 1B will be displaced out of gas washout vent 6800 by inspiratory flow 6A, thereby preventing or at least reducing redelivery of $CO_2$ richer expiratory flow back to the patient for rebreathing. Furthermore, any $CO_2$ richer expiratory flow that remained in peripheral volumes PC1 and PC2 via flow paths 4A and 4B would be prevented from being redelivered back to the entrance of the patient's airways by seal members AS1 and AS2 to prevent rebreathing. In an example, $CO_2$ richer expiratory flow remaining in peripheral volumes PC1 and PC2 may only flow into main chamber MC at levels that would cause breathing discomfort if there was a substantial pressure differential (i.e., a lower relative pressure in main chamber MC), which is prevented during inspiration by inspiratory flow 6C from the flow generator. Thus, seal members AS1 and AS2 work in a number of ways to reduce $CO_2$ rebreathing within the patient interface, e.g., seal members AS1 and AS2 work to reduce the volume between the patient's airways and the vent 6800. Moreover, seal members AS1 and AS2 prevent any $CO_2$ richer expiratory flow that may have remained within the plenum chamber during expiration from subsequently being redelivered and rebreathed by the patient. That is, seal members AS1 and AS2 act as a physical barrier in this example.

FIGS. 20 and 21 show a patient interface according to another example of the present technology including exemplary air flow paths for such patient interface during patient expiration and inspiration respectively. As illustrated, the patient interface includes baffle members BF1 and BF2.

Similar to examples described above, the baffle members BF1 and BF2 are structured and arranged to redirect expiratory flow (e.g., see flow paths 1C and 1D in FIG. 20) away from peripheral volumes PC1 and PC2 and towards the gas washout vent 6800 (e.g., see flow path 1A in FIG. 20). Some expiratory flow may bypass the vent 6800 and flow down the air delivery conduit (e.g., see flow path 1B in FIG. 20).

During inspiration (FIG. 21), most or all of the $CO_2$ richer expiratory flow will be displaced by the inspiratory flow from the flow generator (e.g., see flow path 6A) and directed out the vent 6800 (see e.g. flow paths 6A to 1B). In an example, any seal leak 5 may cause a lower pressure in peripheral volumes PC1 and PC2, which may drive a flow 3B and 3C from the main chamber MC into these peripheral volumes. However, the baffle members BF1 and BF2 are structured and arranged to prevent or at least limit $CO_2$ richer expiratory flow from flowing into these peripheral volumes. In an example where $CO_2$ richer expiratory flow flows into peripheral volumes PC1 and PC2, the baffle members BF1 and BF2 may prevent flow back into main chamber MC for rebreathing by the patient. Moreover, the $CO_2$ richer expiratory flow remaining in peripheral volumes PC1 and PC2 is expected to vent to atmosphere via leak 5.

Thus, baffle members BF1 and BF2 act to reduce $CO_2$ rebreathing by the patient by directing expiratory flow towards the vent and away from additional volumes such as peripheral volumes or chambers PC1 and PC2. Furthermore, baffles members BF1 and BF2 act as a flow barrier to minimize or prevent any rebreathing of $CO_2$ richer expiratory flow that may remain within the plenum chamber during inspiration.

HME and One or More Volume Reducing Members

As mentioned above, the provision of one or more volume reducing members also provides a viable solution to the reduction of $CO_2$ rebreathing when a heat and moisture exchanger (HME) is provided within the plenum chamber. The HME, positioned in the flow path between the patient's airways and the vent, impedes the flow of exhalation exiting via the vent, which can possibly lead to a build-up of $CO_2$ within the plenum chamber. This potential problem is more common in plenum chambers with larger internal volumes, e.g., full-face masks. The provision of one or more volume reducing members according to an example of the present technology can reduce the effective internal volume of the plenum chamber to reduce the volume of $CO_2$ that is rebreathed in patient interfaces with an HME.

For example, FIG. 22 shows a patient interface 6000 structured to house an optional HME 6005, e.g., in the form of a replaceable cartridge, to provide sufficient heat and humidity to the patient during therapy. In an example, the HME 6005 may be integrated or otherwise supported by a front wall portion of the cushion assembly 6175. In the illustrated example, the vent 6800 is provided to the elbow or swivel elbow 6500.

Similar to the above example, upper and lower movable flaps 6900A, 6900B are provided within the plenum chamber 6200 to establish the main chamber MC and peripheral chambers PC1, PC2 separated from the main chamber MC so as to reduce the effective internal volume of the plenum chamber 6200.

In addition to reducing the effective volume of the plenum chamber 6200 to reduce $CO_2$ rebreathing, another benefit of the reduced volume in a system with a HME is the reduced volume of the main chamber MC for which the HME is required to heat and humidify. Thus, the moveable flaps 6900A, 6900B also increase the efficacy of the HME to humidify and heat the volume of gases inhaled by the patient. In addition, the reduction in volume between the patient and the HME will result in more heat and moisture being trapped in said volume upon exhalation.

FIG. 23 shows a patient interface with an HME 6005 according to another example of the present technology, and FIGS. 24 and 25 show exemplary air flow paths for such patient interface during patient expiration and inspiration respectively. As illustrated, the patient interface includes additional seal members AS1 and AS2 and pressurisation ports PP1 and PP2.

In the illustrated example, seal member AS1 may seal superior of the entrance to the nares, while seal member AS2 may seal inferior to the entrance of the mouth. Alternatively, the additional seal member may be a single seal that seals around the mouth and nose but within the plenum chamber of the cushion assembly. In another example, seal member AS1 may seal around the entrance of the nares, while seal member AS2 may seal around the entrance of the mouth. As shown in FIG. 12, seal member AS1 separates the plenum chamber 6200 to form peripheral chamber PC1 while seal member AS2 separates the plenum chamber to form peripheral chamber PC2. Main chamber MC is formed between seal members AS1 and AS2 to include an effective internal volume for delivering a flow of pressurised air to the entrance of the patient's airways. The plenum chamber also comprises a HME 6005 positioned by supporting structures within main chamber MC and in direct fluid communication with the entrance of the patient's airways. The main chamber MC is in fluid communication with peripheral chambers PC1 and PC2 via respective pressurisation ports PP1 and PP2, which are positioned on an anterior side (flow generator side) of the HME 6005. The pressurisation ports PP1 and PP2 allow the pressurisation of the peripheral chambers PC1 and PC2 independently of the main chamber MC. Pressurisation of peripheral chamber PC1 supports sealing by the seal-forming structure in a region superior to the nares. Similarly, the pressurisation of peripheral chamber PC2 supports sealing by the seal-forming structure in a region inferior to the mouth.

During expiration as shown in FIG. 24, seal members AS1 and AS2 ensure that the volume of expired air flows into the main chamber MC and through the HME 6005 without flowing into either of the peripheral chambers PC1 or PC2. This ensures that the moisture and humidity within the expired air is captured within the patient side of the main chamber MC or retained in the HME 6005 for redelivery. As illustrated in FIG. 24, the expired volume of air may still proceed downstream and exit the vent 6800 through the vent flow 1A or proceed down the air delivery conduit via additional expired flow 1B. In this example, seal members AS1 and AS2 ensure that the moisture and heat of vent flow 1A and additional expired flow 1B have been retained in the HME 6005 prior to exiting through vent 6800. In the case where there is leak flow 5 via the seal-forming structure, a pressure differential may form between either of the peripheral chambers PC1 or PC2 in comparison the main chamber MC. That is, pressure may be lost from the peripheral chambers PC1 or PC2 via leak flow 5. In this instance, a pressurisation flow path 4A, 4B may exist through pressurisation ports PP1 or PP2 due to the pressure differential. As shown in FIG. 24, if pressurisation flow paths 4A and 4B were to occur during expiration, the positioning of the pressurisation ports PP1 and PP2 on the anterior side (flow generator side) of the HME 6005 would ensure that the pressurisation flow paths 4A and 4B would occur from a volume of expired air that has already flowed through the HME 6005. Thus, this configuration ensures that volumes of gases lost through leak flow 5 would be limited to volumes where heat and moisture had already been retained by the HME 6005.

During inspiration as shown in FIG. 25, inspiratory mask flow 6C is heated and re-humidified while flowing through the HME 6005 to deliver heated and humidified air at pressure to the entrance of the patient's airways. As noted above, most or all of the $CO_2$ richer expiratory flow will be displaced by the inspiratory flow from the flow generator (e.g., see flow path 6A) and directed out the vent 6800 (see e.g. flow paths 6A to 1B). In the case where leak flow 5 occurs, the peripheral chambers PC1 and PC2 may be pressurised to compensate for pressure losses via respective inspiratory pressurisation flow paths 3B and 3C. This configuration again ensures that the inspiratory pressurisation flow paths 3B and 3C occur from volumes of air that have not been heated or humidified by the HME 6005.

FIG. 26 shows a patient interface with an HME 6005 according to another example of the present technology, and FIGS. 27 and 28 show exemplary air flow paths for such patient interface during patient expiration and inspiration respectively. As illustrated, the patient interface includes baffle members BF1 and BF2 and a HME 6005 with leak ports LP1 and LP2.

During expiration as shown in FIG. 27, the baffles BF1 and BF2 may direct expiratory flow away from the peripheral chambers PC1 and PC2, such that the bulk of expiratory flow is directed through the HME 6005 for heat and moisture capture. That is, the baffles BF1 and BF2 may provide a path of least resistance to vent flow 1A, when compared to flow paths LP1 or LP2. The expired volume of air may still proceed downstream and exit the vent 6800 through the vent flow 1A or proceed down the air delivery conduit via additional expired flow 1B. The baffles BF1 and BF2 act as a flow director to minimise the loss of moisture from expiratory flow through seal leak paths 5. If any leak was to occur through leak paths 5 during expiration, a resulting pressure differential in peripheral chambers PC1 and PC2 would cause the leak to occur via flow paths 4A and 4B rather than from the main chamber MC via flow paths 1C or 1D. That is, the baffles BF1 and BF2 would direct flow such that leak of expiratory flow from the main chamber MC would be limited to flow that has already flowed through the HME 6005 for heat and moisture retention. Thus, moisture loss through leak would be minimised from expiratory flow.

During inspiration as shown in FIG. 28, the baffle members BF1 and BF2 act to direct inspiratory flow 6C that has already flowed through the HME 6005 away from the peripheral chambers PC1 and PC2 and towards the entrance of the patient's airways. Furthermore, the leak ports LP1 and LP2 encourage any flow into the peripheral chambers PC1 and PC2 during inspiration occurs from flow that has not flowed through the HME 6005 (e.g., flow paths 3B and 3C). That is, if seal leak 5 were to occur causing a lower pressure in the peripheral chamber PC1 and PC2 in comparison to the main chamber MC, the positioning of the leak ports LP1 and LP2 on an opposing side of the HME 6005 relative to the patient would allow inspiratory flow to bypass the HME 6005 prior to flowing into the peripheral chambers PC1 and PC2 then eventually to atmosphere. Thus, the leak ports LP1 and LP2 would limit any moisture loss from the HME 6005.

It should be appreciated that one or more volume reducing members according to an example of the present technology may be applied to plenum chambers of patient interfaces of any suitable size and configuration. For example, it should be appreciated that the plenum chamber may be established in various manners and formed of one or more various materials having one or more various material properties, e.g., integral one-piece plenum chamber, one or more separate components attached or otherwise formed to define the plenum chamber. In such alternative examples, the one or more volume reducing members may be provided (e.g., connected) to a front wall portion of the chamber, and/or to a seal forming structure of the chamber.

Also, aspects of the present technology have been described as having particular application to patient interfaces with larger internal volumes, e.g., full-face masks. However, it should be appreciated that one or more aspects of the present technology may be applied to other suitable interface types, e.g., nasal masks, to reduce deadspace volume, e.g., to improve $CO_2$ rebreathing and/or increase the efficacy of a HME.

5.3.3 Positioning and Stabilising Structure

The seal-forming structure 3100 of the patient interface 3000 of the present technology may be held in sealing position in use by the positioning and stabilising structure 3300.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 comprises a strap constructed from a laminate of a fabric patientcontacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilizing structure 3300 provides a retaining force configured to correspond to a particular size of head and/or shape of face. For example one form of positioning and stabilizing structure 3300 provides a retaining force suitable for a large sized head, but not a small sized head. In another example, a form of positioning and stabilizing structure 3300 provides a retaining force suitable for a small sized head, but not a large sized head.

5.3.4 Vent

In one form, the patient interface 3000 includes a vent 3400 constructed and arranged to allow for the washout of exhaled gases, e.g. carbon dioxide.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 Glossary

For the purposes of the present technology disclosure, in certain forms of the present technology, one or more of the following definitions may apply. In other forms of the present technology, alternative definitions may apply.

5.4.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow'.

In the example of patient respiration, a flow rate may be nominally positive for the inspiratory portion of a breathing cycle of a patient, and hence negative for the expiratory portion of the breathing cycle of a patient. Total flow rate, $Qt$, is the flow rate of air leaving the RPT device. Vent flow rate, $Qv$, is the flow rate of air leaving a vent to allow washout of exhaled gases. Leak flow rate, $Ql$, is the flow rate of leak from a patient interface system or elsewhere. Respiratory flow rate, $Qr$, is the flow rate of air that is received into the patient's respiratory system.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory disease.

Pressure: Force per unit area. Pressure may be expressed in a range of units, including $cmH_2O$, g-f/cm$^2$ and hectopascal. 1 $cmH_2O$ is equal to 1 g-f/cm$^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.4.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a typically transparent thermoplastic polymer of Bisphenol-A Carbonate.

5.4.1.2 Mechanical Properties

Resilience: Ability of a material to absorb energy when deformed elastically and to release the energy upon unloading.

'Resilient': Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

'Floppy' structure or component: A structure or component that will change shape, e.g. bend, when caused to support its own weight, within a relatively short period of time such as 1 second.

'Rigid' structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.4.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory airflow rate, as opposed to "true respiratory flow rate" or "true respiratory airflow rate", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.4.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

5.4.4 Anatomy 5.4.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 5.4.4.2 Anatomy of the Skull Frontal bone: The frontal bone includes a large vertical portion, the squama *frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.4.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.4.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.4.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a cushion structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.4.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.4.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical-topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.4.6.3 Space Curves

Space curves: Unlike a plane curve, a space curve does not necessarily lie in any particular plane. A space curve may be considered to be a one-dimensional piece of three-dimensional space. An imaginary person walking on a strand of the DNA helix walks along a space curve. A typical human left ear comprises a left-hand helix, see FIG. 3P. A typical human right ear comprises a right-hand helix, see FIG. 3Q. FIG. 3R shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3O), or alternatively by a left-hand rule (FIG. 3N).

Osculating plane: The plane containing the unit tangent vector and the unit principal normal vector. See FIGS. 3N and 3O.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3R, since T2>T1, the magnitude of the torsion near the top coils of the helix of FIG. 3R is greater than the magnitude of the torsion of the bottom coils of the helix of FIG. 3R With reference to the right-hand rule of FIG. 3O, a space curve turning towards the direction of the right-hand binormal may be considered as having a right-hand positive torsion (e.g. a right-hand helix as shown in FIG. 3R). A space curve turning away from the direction of the right-hand binormal may be considered as having a right-hand negative torsion (e.g. a left-hand helix).

Equivalently, and with reference to a left-hand rule (see FIG. 3N), a space curve turning towards the direction of the left-hand binormal may be considered as having a left-hand positive torsion (e.g. a left-hand helix). Hence left-hand positive is equivalent to right-hand negative. See FIG. 3S.

5.4.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by the plane curve 301D.

A structure may have a two-dimensional hole, e.g. a hole bounded by a surface. For example, an inflatable tyre has a two dimensional hole bounded by the inside surface of the tyre. In another example, a bladder with a cavity for air or gel could have a two-dimensional hole. See for example the cushion of FIG. 3L and the example cross-section there through in FIG. 3M. In a yet another example, a conduit may comprise a one-dimension hole (e.g. at its entrance or at its exit), and a twodimension hole bounded by the inside surface of the conduit. See also the two dimensional hole through the structure shown in FIG. 3K, bounded by surface 302D.

5.5 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 5.6 REFERENCE SIGNS LIST | |
|---|---|
| seal member | AS1, AS2 |
| baffle member | BF1, BF2 |
| deadspace volume | DS1, DS2 |
| leak port | LP1, LP2 |
| main chamber | MC |
| peripheral chamber | PC, PC1, PC2, PC3, PC4 |
| pressurisation port | PP1, PP2 |
| vent flow | 1A |
| additional expired flow | 1B |
| flow path | 1C, 1D |
| expiration flow | 2A, 2B |
| leak flow path | 2C, 2D |
| flow path | 3B, 3C |
| flow path | 4A, 4B |
| leak flow | 5 |
| inspiratory vent flow | 6A |
| inspiratory flow path | 6B |
| inspiratory mask flow | 6C |
| HME | 15 |
| patient | 1000 |
| bed partner | 1100 |
| patient interface | 3000 |
| seal - forming structure | 3100 |
| plenum chamber | 3200 |
| positioning and stabilizing structure | 3300 |
| vent | 3400 |
| connection port | 3600 |
| forehead support | 3700 |
| RPT device | 4000 |
| air circuit | 4170 |
| humidifier | 5000 |
| patient interface | 6000 |
| HME | 6005 |
| frame member | 6050 |
| seal - forming structure | 6100 |
| front wall portion | 6150 |
| cushion assembly | 6175 |
| plenum chamber | 6200 |
| positioning and stabilising structure | 6300 |
| swivel elbow | 6500 |
| connection port | 6600 |
| vent | 6800 |
| movable flap | 6900 |
| movable flap | 6900A |
| movable flap | 6900B |
| movable flap | 6900C |
| movable flap | 6900D |
| connecting portion | 6905 |
| end portion | 6910 |

The invention claimed is:

1. A patient interface for sealed delivery of a flow of air at a continuously positive pressure with respect to ambient air pressure to an entrance to the patient's airways including the entrance of a patient's nares and a patient's mouth, wherein the patient interface is configured to maintain a therapy pressure in a range of 4 cmH$_2$O to 30 cmH$_2$O above the ambient air pressure in use, throughout the patient's respiratory cycle, while the patient is sleeping, to ameliorate sleep disordered breathing;

said patient interface comprising:
a cushion assembly adapted to form a seal around the patient's nose and mouth, the cushion assembly defining a plenum chamber pressurised at the therapy pressure above the ambient air pressure in use,
wherein the cushion assembly includes a seal forming structure adapted to form the seal at least along a portion of the patient's nose,
wherein the seal and the plenum chamber is adapted to only surround the patient's nose and mouth of the patient's face;
a gas washout vent configured to allow a flow of patient exhaled $CO_2$ to an exterior of the patient interface to minimise rebreathing of exhaled $CO_2$ by the patient; and
one or more movable flaps or baffles provided within the plenum chamber to reduce an internal volume of the plenum chamber,
wherein the one or more movable flaps or baffles is configured and arranged to separate a main volume of the plenum chamber for delivery of the therapy pressure from a deadspace volume of the plenum chamber, the main volume adapted to be in direct fluid communication with the entrance of the patient's nares, the entrance of the patient's mouth, and the gas washout vent,
wherein the one or more movable flaps or baffles creates a flow bias such that all patient inhalation and patient exhalation throughout the patient's respiratory cycle occurs via the main volume.

2. The patient interface according to claim 1, wherein the one or more movable flaps or baffles is arranged to reduce a volume of $CO_2$ that is rebreathed by the patient.

3. The patient interface according to claim 1, wherein the one or more movable flaps or baffles is arranged to reduce the internal volume of the plenum chamber without altering the seal.

4. The patient interface according to claim 1, wherein the one or more movable flaps or baffles includes the one or more movable flaps.

5. The patient interface according to claim 4, wherein the one or more movable flaps separate or divide the plenum chamber into a main chamber and at least one peripheral chamber separate and distinct from the main chamber, the main chamber comprising the main volume.

6. The patient interface according to claim 5, wherein the at least one peripheral chamber comprises the deadspace volume within the plenum chamber.

7. The patient interface according to claim 5, wherein the internal volume of the plenum chamber is reduced to the main volume of the main chamber.

8. The patient interface according to claim 5, wherein the one or more movable flaps includes an upper or superior movable flap arranged to establish the at least one peripheral chamber adapted to be positioned above the patient's nares.

9. The patient interface according to claim 5, wherein the one or more movable flaps includes a lower or inferior movable flap arranged to establish the at least one peripheral chamber adapted to be positioned below the patient's lower lip.

10. The patient interface according to claim 4, wherein each of the one or more movable flaps includes a free end portion adapted to be oriented towards the patient's face.

11. The patient interface according to claim 10, wherein each of the one or more movable flaps is flexible and is adapted to allow each of the one or more movable flaps to deform and/or flex to conform to the patient's face.

12. The patient interface according to claim 1, further comprising a heat and moisture exchanger within the plenum chamber.

13. The patient interface according to claim 1, wherein the cushion assembly includes a front wall portion and the seal forming structure.

14. The patient interface according to claim 13, wherein the front wall portion comprises the gas washout vent.

15. The patient interface according to claim 13, wherein the one or more movable flaps or baffles is provided to the front wall portion.

16. The patient interface according to claim 1, wherein the one or more movable flaps or baffles is arranged to separate the main volume from the deadspace volume provided inferior the entrance to the patient's mouth.

17. The patient interface according to claim 1, wherein the one or more movable flaps or baffles is constructed of an elastomeric material.

18. The patient interface according to claim 1, wherein the deadspace volume is pressurised via the flow of air at the continuously positive pressure and provides pneumatic sealing of the cushion assembly.

19. The patient interface according to claim 1, wherein the one or more movable flaps or baffles is structured and arranged to obstruct flow between the main volume and the deadspace volume.

20. The patient interface according to claim 1, wherein the one or more movable flaps or baffles separates or divides the plenum chamber into a main chamber and at least one peripheral chamber separate and distinct from the main chamber, the main chamber comprising the main volume.

21. The patient interface according to claim 20, further comprising one or more pressurisation ports arranged to allow pressurisation via the flow of air at the continuously positive pressure of the at least one peripheral chamber.

22. The patient interface according to claim 21, further comprising a heat and moisture exchanger within the plenum chamber, and the one or more pressurisation ports are positioned on an anterior side of the heat and moisture exchanger.

23. The patient interface according to claim 1, wherein the one or more movable flaps or baffles comprises an end portion adapted to sealingly engage with the patient's face.

24. The patient interface according to claim 1, wherein the seal forming structure is adapted to form the seal along a nasal bridge region of the patient's nose.

25. The patient interface according to claim 24, wherein the seal forming structure is adapted to form the seal along the nasal bridge region, sides of nose regions, cheek regions, side of mouth regions, and a below the lower lip region.

26. The patient interface according to claim 1, wherein the deadspace volume is provided superior the main volume and the entrance to the patient's nares.

27. The patient interface according to claim 1, wherein the flow bias is directed away from the deadspace volume.

* * * * *